US006872574B2

(12) United States Patent
Cravatt et al.

(10) Patent No.: US 6,872,574 B2
(45) Date of Patent: Mar. 29, 2005

(54) PROTEOMIC ANALYSIS

(75) Inventors: Benjamin F. Cravatt, La Jolla, CA (US); Erik Sorensen, San Diego, CA (US); Matthew P. Patricelli, San Diego, CA (US); Martha Lovato, San Diego, CA (US); Gregory Adam, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 154 days.

(21) Appl. No.: 09/836,148

(22) Filed: Apr. 16, 2001

(65) Prior Publication Data

US 2002/0040275 A1 Apr. 4, 2002

Related U.S. Application Data

(63) Continuation of application No. 09/738,954, filed on Dec. 15, 2000.
(60) Provisional application No. 60/195,954, filed on Apr. 10, 2000, provisional application No. 60/212,891, filed on Jun. 20, 2000, and provisional application No. 60/222,532, filed on Aug. 2, 2000.

(51) Int. Cl.[7] .......................... G01N 33/50; C11Q 1/32; C12Q 1/34
(52) U.S. Cl. ..................... 436/119; 436/86; 436/103; 436/149; 436/172; 435/7.1; 435/7.2; 435/18; 435/26
(58) Field of Search .................. 435/4, 7.1, 7.2, 435/7.7, 7.72, 18, 26; 436/86, 103, 119, 149, 172

(56) References Cited

U.S. PATENT DOCUMENTS

| 5,151,164 A | 9/1992 | Blanchard et al. .......... 204/451 |
| 6,197,599 B1 | 3/2001 | Chin et al. ................... 436/518 |
| 6,391,649 B1 * | 5/2002 | Chait et al. .................. 436/173 |

FOREIGN PATENT DOCUMENTS

| WO | WO 00/00823 | 1/2000 |
| WO | WO 00/11208 | 3/2000 |

OTHER PUBLICATIONS

Liu et al., Activity–Based Protein Profiling: The Serine Hydrolases, 1999, PNAS, 96(26):14694–14699.*
Gygi et al., Quantitative Analysis of complex Protein Mixtures Using Isotope–coded Affinity Tags, Oct. 1999, Nature Biotech., 17:994–999.*
Liu et al., Activity–Based Protein Profiling: The Serine Hydrolases, 1999, PNAS, 96(26):14694–14699.*
Albeck et al., "Mechanism of Cysteine Protease Inactivation by Peptidyl Epoxides," *Biochem. J.*, vol. 322, No. 3, 1997, pp. 879–884.
Kam et al., "Biotinylated Isocoumarins, New Inhibitors and Reagents for Detection, Localization, and Isolation of Serine Proteases," *Bioconjugate Chemistry*, vol. 4, No. 6, 1993, pp. 560–567.

Tenorio et al., "An Immunohistochemical Investigation of the Expression of Parathyroid Hormone Receptors in Rat Cementoblasts," *Archives of Oral Biology*, vol. 41, No. 3, 1996, pp. 299–305.
Liu, Yongsheng et al., "Activity–Based Protein Profiling: The Serine Hydrolases," *Proceedings of the National Academy of Sciences of USA*, vol. 96, No. 26, Dec. 21, 1999, pp. 14694–14699.
Bogyo, Matthew et al., "Covalent Modification of the Active Site Threonine of Proteasomal β Subunits and the *Escherichia Coli* Homolog HsIV By a New Class of Inhibitors," *Proc. Natl. Acad. Sci. USA*, vol. 94, Jun. 1997, pp. 6629–6634.
Gygi, Steven P. et al., "Quantitative Analysis of Complex Protein Mixtures Using Isotope–Coded Affinity Tags," *Nature Biotechnology*, vol. 17, Oct. 1999, pp. 994–999.
Adam, G.C., et al., "Profiling the Specific Reactivity of the Proteome with Non–Directed Activity–Based Probes," *Chemistry & Biology*, vol. 8, 2001, pp. 81–95.
Purohit, A., et al., Inactivation of Steroid Sulfatase by an Active Site–Directed Inhibitor, Estrone–3–O–Sulfamate, *Biochemistry*, vol. 34, 1995, pp. 11508–11514.
Moore, A.W., et al., "Rapid Comprehensive Two–Dimensional Separations of Peptides Via RPLC–Optically Gated Capillary Zone Electrophoresis," *Anal Chem*, 1995, vol. 67(19); pp. 3448–3455.
Figeys, D., "Identification of Proteins by Capillary Electrophoresis–Tandem Mass Spectrometry. Evaluation of an On–line Solid–Phase Extraction Device," *J. Chromatogr A*, Feb. 28, 1997, vol. 763(1–2), pp. 295–306.
Wu, S.L., "The Use of Sequential High–Performance Liquid Chromatography and Capillary Zone Electrophoresis to Separate the Glycosylated Peptides from Recombinant Tissue Plasminogen Activator to a Detailed Level of Microheterogeneity," *Anal Biochem*, Nov. 1997, vol. 253(1), pp. 85–97.

(Continued)

*Primary Examiner*—Padmashri Ponnaluri
*Assistant Examiner*—My-Chau T Tran
(74) *Attorney, Agent, or Firm*—Gray Cary Ware & Freidenrich, LLP

(57) ABSTRACT

The present invention provides methods for analyzing proteomes, as cells or lysates. The analysis is based on the use of probes that have specificity to the active form of proteins, particularly enzymes and receptors. The probes can be identified in different ways. In accordance with the present invention, a method is provided for generating and screening compound libraries that are used for the identification of lead molecules, and for the parallel identification of their biological targets. By appending specific functionalities and/or groups to one or more binding moieties, the reactive functionalities gain binding affinity and specificity for particular proteins and classes of proteins. Such libraries of candidate compounds, referred to herein as activity-based probes, or ABPs, are used to screen for one or more desired biological activities or target proteins.

5 Claims, 24 Drawing Sheets

OTHER PUBLICATIONS

Browne, T.R., "Performance of Human Mass Balance/Metabolite Identification Studies Using Stable Isotope (13C, 15N) Labeling and Continuous–Flow Isotope–Ratio Mass Spectrometry as an Alternative to Radioactive Labeling Methods," *J. Clin Pharmacol*, Mar. 1993, vol. 33(3), pp. 246–252.

Wagner, D.S., et al., Ratio Encoding Combinatorial Libraries with Stable Isotopes and their Utility in Pharmaceutical Research, *Comb Chem High Throughput Screen*, Oct. 1998, vol. 1(3), pp. 143–153.

Bogyo et al., Substrate Binding and Sequence Preference of the Proteasome Revealed by Active–Site–Directed Affinity Probes:, Chemistry and Biology, Current Biology, London, GB, Vo. 5, No. 6, pp. 307–320 (1998).

Faleiro et al., "Multiple Species of CPP32 and Mch2 are the Major Active Caspases Present in Apoptotic Cells", EMBO Journal, Oxford University Press, Surrey, GB, Vo. 16, No. 9, pp. 2271–2281, (1997).

Greenbaum et al. "Epoxide Electrophiles as Activity–Dependent Cysteine Protease Profiling and Discovery Tools", Chemistry and Biology, Current Biology, London, GB, vol. 7, No. 8, pp. 569–581, (2000).

Horner et al., "Organophosphorus Compounds 110. Specific Fluorescence Labeling of Serine Enzymes", Liebigs Annalen Der Chemie, No. 1 pp. 1–21 (1985).

Kay et al., "The Synthesis Kinetic Characterization and Application of Biotinylated Aminoacylchloromethanes for the Detection of Chymotrypsin and Trypsin–like Proteinases", Biochemical Journal, Portland Press, London, GB, vol. 283, pp. 455–459 (1992).

Martins et al. "Activation of Multiple Interluekin–1β Converting Enzymes Homologues in Cytosol and Nuclei of HL–60 Cells during Etoposide–induced Apoptosis" Journal of Biological Chemistry, vol. 272, No. 11, Issue of Mar. 14, pp. 7421–7430 (1997).

Thornberry et al., "Inactivation of Interluekin–1β Converting Enzyme by Peptide (Acyloxy) methyl Ketones", Biochemistry, American Chemical Society, Easton, PA, US, vol. 33, No. 13, pp. 3934–3940 (1994).

* cited by examiner

A

B

C

D

A

B

PROTEOMIC ANALYSIS

CROSS-REFERENCE TO RELATED APPLICATIONS

This application is a Continuation of Ser. No. 09/738,954, filed Dec. 15, 2000, which claims priority under 35 U.S.C. §119(e)(1) to U.S. provisional applications Ser. Nos. 60/195,954, filed Apr. 10, 2000; 60/212,891, filed Jun. 20, 2000; and 60/222,532, filed Aug. 2, 2000, all of which are herein incorporated by reference in their entirety.

This invention was made with Government support under Contract No. MH58542 and CA87660, awarded by the National Institutes of Health. The government may have certain rights in the invention.

FIELD OF THE INVENTION

The field of this invention is analyzing portions of a proteome.

BACKGROUND OF THE INVENTION

Determination of the genomic sequence of higher organisms, including humans, is now an attainable goal. However, this analysis represents only one aspect of the information encoded by the genome. Genes are expressed in an ordered and timely manner, and are also exhibit a precise spatial and temporal expression pattern. Consequently, knowing the sequence of the genome is insufficient to explain biology and to understand disease. More significantly, genes are transcribed to messenger RNA, which is then translated to protein. It is the protein, or gene product, that exhibits activity, and carries out the work of the cell. With the post-genome era rapidly approaching, new strategies for the analysis of proteins are being developed. Most conventional approaches focus on recording variations in protein level. These approaches are commonly referred to as "proteomics". In general, proteomics seeks to measure the abundance of broad profiles of proteins from complex biological mixtures. In the most common embodiments, proteomics involves separating the proteins within a sample by two-dimensional SDS-PAGE. Then, the individual protein spots patterns of these gels can be compared to get indications as to the relative abundance of a particular protein in two comparative samples. The approach can even be extended to determine the molecular identity of the individual protein spots by excising the spots and subjecting them to peptide mass fingerprinting. More recently, methods have been described for eliminating the electrophoresis steps and performing proteomics by directly analyzing the complex mixture by mass spectrometry. For example, methods currently described in the art provide chemically reactive probes that can be reacted with a protein mixture to label many proteins in that mixture in a non-specific, or non-directed, manner providing only a quantitative analysis of proteins (see Aebersold, PCT/US99/19415). Such methods teach that there are many chemically reactive amino acid residues within a protein which are individually reactive and which can be conjugated to chemical probes, whereby protein conjugates can be subsequently quantified to yield an indication of protein abundance. Similarly, Wells et al. (PCT/US99/14267; PCT/US98/21759) describe methods for identifying small organic molecule ligands that bind to biological target molecules without the requirement that the ligand bind to an active site on a target molecule. These methods do not describe selectively detecting active versus inactive proteins within a sample.

The need to devise methods of measuring protein activity, as opposed to abundance are best illustrated by an important subset of proteins called enzymes. Many classes of enzymes are encoded by the genome. Enzymes are key to almost every biologic process, including blood coagulation, inflammation, angiogenesis, neural plasticity, peptide hormone processing and T-lymphocyte-mediated cytotoxicity. Several human diseases are associated with dysfunctions in enzymes. These include, but are not limited to, hemorrhagic disorders, emphysema, arthritis and even to cancer.

Although current proteomic approaches, such as those described above, could theoretically provide information on the abundance of an enzyme, these methods fail to report on enzyme activity. This is a key limitation because the activity of enzymes, and even other proteins, is often regulated by post-translational modification. Importantly, the active site represents only a small portion of the entire surface of the protein. The chemical nature and reactivity of this active site is governed by the local environment of the site, which is conferred by its amino acid compositions and its three dimensional structure. The shape and/or exposure of the active site of an enzyme can be modulated by any number of biological events. In many cases, the active site of an enzyme can be masked by natural inhibitors. Alternatively, the shape of the active site can be made more favorable for activity by the action of allosteric cofactors.

In many cases a library of compounds is screened to identify those compounds with desired biological effect. Once such compounds ("leads") are identified, an iterative process is undertaken to refine their chemical and biochemical properties so that they can be used as drugs. A key step in this iterative process is the identification of the biological target molecule that is inhibited by the lead compound. Knowing the identity of the biological target molecule allows one to streamline the development process by devising simplified, high-throughput assays to test additional compounds based on the structure of the lead compound for enhanced potency. In addition, it is vital to know the identity of the biological target so that one can interpret studies aimed at testing such compounds for effect in animals and in human trials.

One of the inherent difficulties with the entire development process is that it is often difficult to identify the biological target molecule for lead compounds. For example, one might establish a screen to identify leads that block cell division. If successful, such a screen might identify a number of leads, all with varying ability to block cell division. Cell division is a complex process involving numerous biochemical pathways and hundreds of proteins. The lead compounds might therefore, bind to and inhibit any one of these proteins.

There is no simple way of determining what the biological target molecule is for lead compounds identified from such screens. Nor, is there a way of knowing if multiple lead compounds interact with the same, or with different, biological target molecules. Consequently, the identification of the biological target molecule relies on conventional fractionation and purification strategies, which are cumbersome, time consuming and expensive. Moreover, without knowledge of the identity of the biological target molecule, and an understanding of its precise biochemical activity, one may be unable to devise assays to track its purification during these steps. Consequently, the identity of such biological target molecules is often impossible to determine using current approaches.

SUMMARY OF THE INVENTION

Systems are provided for identifying portions of proteomes, where the proteome activity is determined for a plurality of active proteins and the effect of agents on the activity of such proteome portion. The system includes methods for identifying probes useful for reacting with active proteins, probes for reacting with active proteins and methods for identifying the proteins with which the probes have reacted. The probes comprise a reactive moiety that as part of the probe is limited in its reactivity to the target active proteins, a ligand for sequestering the conjugate of the probe and the target protein and optionally an identifier that can be released and analyzed, and will be referred to as "activity based probes" ("ABPs").

The system includes identifying groups having specific affinities for a protein conformation, identifying target proteins in a proteome of biological interest related to the status of a biological system, producing probes for binding to groups of target proteins, assaying proteomic profiles for groups of proteins and analyzing the resulting data. The systems can also be used for screening for bioactivity profiles of candidate compounds.

DETAILED DESCRIPTION OF THE INVENTION

Figure 1:
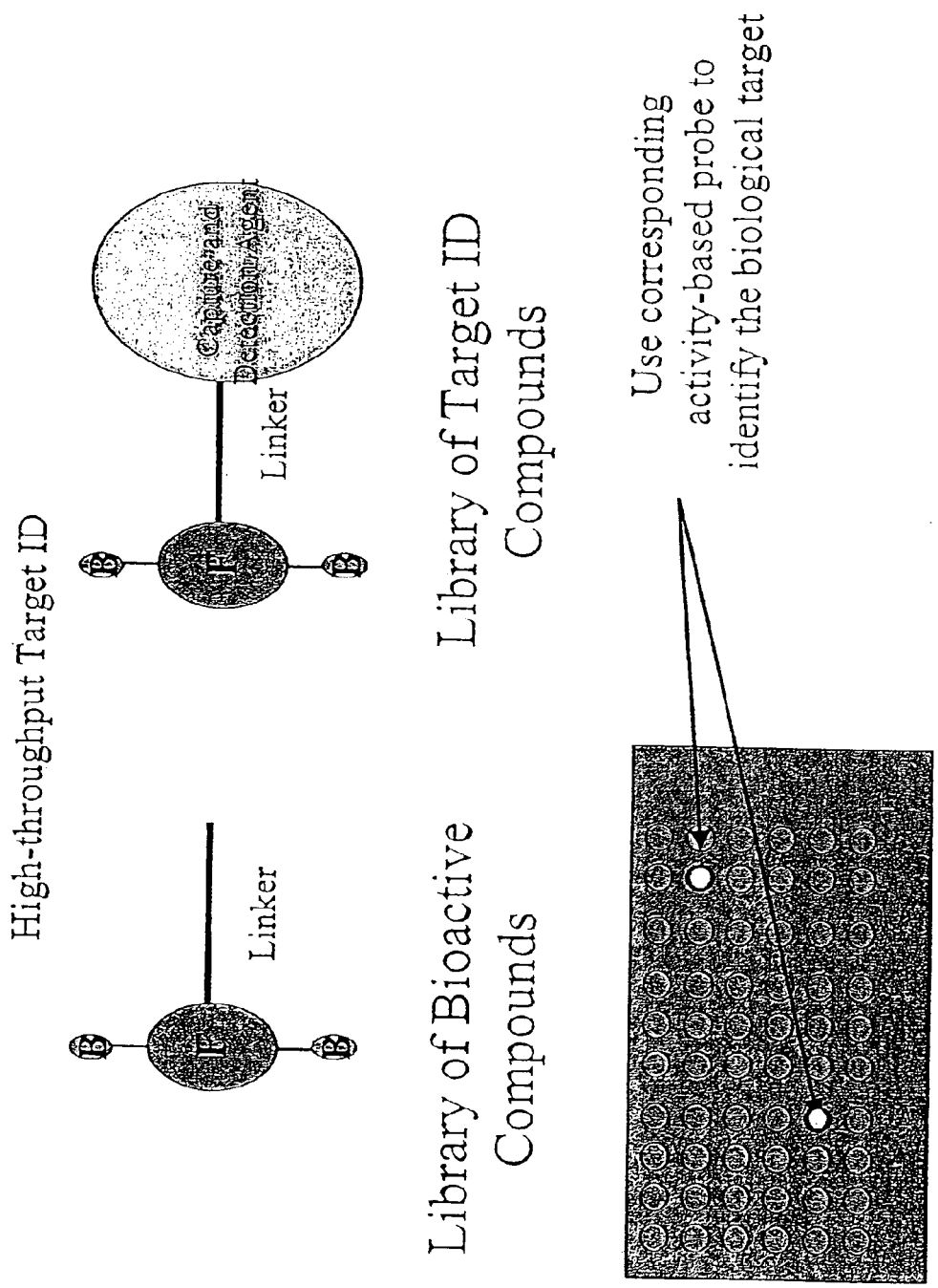
FIG. 1 is a schematic diagram of integrated cell-based screening for bioactive compounds (i.e., the non-labeled or untagged library) with target identification (i.e., using the corresponding labeled or tagged library).

In accordance with the subject invention systems are provided for assaying proteomes as to a specific protein or group of related proteins and to determine the effects of agents on such proteins in a proteome. The systems include methods for identifying probes for use in the assay, the probes, the methods of reacting the probes with the proteomic mixture, and methods for analyzing the data from the assay for at least semi-quantitatively determining the target members of the proteome and the effect of the agents on the activity of a portion of the proteome. Kits are also provided of combinatorial libraries for screening proteomes to identify members having specific affinities and for screening proteomes, where the kits comprise different probes for different proteins or related groups of proteins. As part of the system for discovering probes for any related group of proteins, combinatorial libraries are employed having a common reactive functionality as part of a functional group and usually a common linker, linking the functional group to a ligand for which a receptor is available or a chemically reactive functionality reacting with a reciprocal functionality for adding a ligand. The results with an active proteome are repeated with an inactive proteome to determine the degree of activity of the total target protein as compared to active protein. Depending on the nature of the functional group, part of linker or part of the functional group may comprise the variable component.

The system uses probes specific for a specific or group of related proteins and combines one or a mixture of probes, depending on the specificity of the probes and the variety in the group or groups of related proteins to be assayed. The reaction mixture provides conditions under which the probes react substantially preferentially with active target proteins. By "active" is intended that the protein is in its native conformation and is able to interact with an entity that it normally interacts with, e.g. enzyme with substrate and cofactor, receptor with ligand, etc. Using the ligand, target conjugated probes are sequestered by means of the ligand and different protocols may be employed to determine the amount of the target proteins present in the medium as a group or individually. Optionally the sequestered proteins may be further assayed to identify the specific proteins to which the probes bound.

The combinatorial aspect of the present invention will be described first. There are provided combinatorial chemical libraries containing a plurality of activity-based probes (ABPs), where the individual members may be correspondingly tagged or labeled. The methods of the invention employ ABP-containing libraries for identifying bioactive compounds and for identifying target proteins in a mixture of proteins. It will be appreciated that the ABPs of the invention are class-selective and activity based. Therefore, the present invention allows for rapid target identification and isolation. (see U.S. Ser. Nos. 60/195,954, filed Apr. 10, 2000 and 60/212,891, filed Jun. 20, 2000, both of which are incorporated by reference in their entirety herein).

The combinatorial chemical libraries of the present invention are useful as screening tools for discovering new lead structures through evaluation of the compounds in the library across an array of biological assays, including the discovery of selective inhibition patterns across isozymes and related enzymes, where the enzymes share a common functionality at the active site, allelic proteins, binding to a family of ligands, etc. Thus, the library is useful as a tool for drug discovery, i.e., it is a means to discover novel lead compounds by screening the library against a variety of biological targets, and also as a tool for the development of structure-activity relationships in large families of related compounds. The combinatorial libraries after reacting with a proteome provide compositions of conjugates between members of the library and target proteins. Such compositions are useful for producing antibodies for sequestering the target proteins from the proteomic mixture, digestion and identification of the target protein using mass spectrometric analysis and data banks, as standards for measuring the amount of conjugate formed in other analyses with the same or different probes, and the like.

The inventive methods employ affinity-labeled or target protein directed protein reactive reagents, ABPs that allow for the selective detection and subsequent isolation of active proteins from complex mixtures. The isolated proteins are characteristic of the presence of a protein function, e.g., an enzymatic activity, protein complex formation, protein-nucleic acid interactions, etc., in those mixtures. Isolated proteins are optionally characterized by mass spectrometric (MS) techniques. In particular, the sequence of isolated proteins can be determined using tandem MS (MS") techniques, and by application of sequence database searching techniques, the protein from which a sequenced peptide originated can be identified. The ABPs also provide for differential labeling, e.g. isotopic or atomic (different atomic weight elements), of the isolated proteins, which facilitates quantitative determination by mass spectrometry of the relative amounts of active proteins in different samples.

A "combinatorial library" is a collection of compounds in which the compounds comprising the collection are composed of one or more types of sub-units. The library will have at least 2 members, rarely less than about 5 members, usually at least about 10 members, frequently will have about 50 members or more, usually fewer than about 1,000 members, more usually fewer than about 500 members. The sub-units may be selected from natural or unnatural moieties, including a variety of chemical moieties, such as synthetic compounds, naturally occurring compounds, e.g. amino acids, nucleotides, sugars, lipids, and carbohydrates, and synthetic analogs thereof, which are readily available commercially in a large variety of compounds. The compounds of the combinatorial library differ in one or more ways with respect to the number, order, type or types of or modifications made to one or more of the sub-units comprising the compounds. Alternatively, a combinatorial library may refer to a collection of "core molecular organization" which vary as to the conformation, size and charge distribution as a result of the presence of other moieties or differences in the way the core molecular organization is organized. The collection of compounds is generated in a systematic way. Any method of systematically generating a collection of sub-units differing from each other in one or more of the ways set forth above is a combinatorial library.

For understanding of the terms used in the subject application, a number of the generic terms is illustrated with examples coming within the genus.

A "chemical group" is an atom or assemblage of atoms and organic chemical groups include but are not limited to alkyl, alkenyl, alkynyl, alkoxy, aryl, alkylaryl, heterocycle including heteroaryl, amide, thioamide, ester, amine, ether, thioether, halo, imine, cyano, nitro, carboxy, keto, aldehydo, and combinations thereof.

"Alkyl" is intended to include aliphatically saturated linear or branched, hydrocarbon structures and combinations thereof "Lower alkyl" means alkyl groups of from 1 to 8 carbon atoms. Examples of lower alkyl groups include methyl, ethyl, propyl, isopropyl, butyl, s- and t-butyl, pentyl, hexyl, octyl, and the like. Preferred alkyl groups are those of $C_{20}$ or below, particularly $C_{10}$ or below.

"Cycloalkyl" includes cyclic hydrocarbon groups of from 3 to 8 carbon atoms. Examples of lower cycloalkyl groups include c-propyl, c-butyl, c-pentyl, norbornyl, decalin, and the like, and may be aliphatically saturated or unsaturated.

"Alkenyl" includes C2–C8 unsaturated hydrocarbons of a linear or branched configuration and combinations thereof. Examples of alkenyl groups include vinyl, allyl, isopropenyl, pentenyl, hexenyl, 1-propenyl, 2-butenyl, 2-methyl-2-butenyl, 2,4-hexadienyl and the like.

"Alkynyl" includes C2–C8 hydrocarbons of a linear or branched configuration and combinations thereof containing at least one carbon-carbon triple bond. Examples of alkynyl groups include ethyne, propyne, butyne, pentyne, 3-methyl-1-butyne, 3,3-dimethyl-1-butyne and the like.

"Alkoxy" refers to groups of from 1 to 8 carbon atoms of a straight, branched, cyclic configuration and combinations thereof. Examples include methoxy, ethoxy, propoxy, isopropoxy, cyclopropyloxy, cyclohexyloxy and the like.

"Acylamino" refers to acylamino groups of from 1 to 8 carbon atoms of a straight, branched or cyclic configuration and combinations thereof. Examples include acetylamino, butyrylamino, cyclohexylanoylamino, and the like.

"Hydrocarbylamino" refers to a moiety consisting of hydrogen and carbon bonded to nitrogen and of from about 1 to 8 carbon atoms for each hydrocarbyl group, there being up to 4, usually 3, hydrocarbyl groups. By "hydrocarbyl is intended any molecule or core of a molecule composed solely of hydrogen and carbon.

"Halogen" includes F, Cl, Br, and I.

"Halophenyl" means phenyl substituted with 1–5 halogen atoms. Examples include pentachlorophenyl, pentafluorophenyl and 2,4,6-trichlorophenyl.

"Aryl" and "heteroaryl" mean a 5- or 6-membered aromatic or heteroaromatic ring containing 0–3 heteroatoms selected from O, N, or S; a bicyclic 9- or 10-membered aromatic or heteroaromatic ring system containing 0–3 heteroatoms selected from O, N, or S; or a tricyclic 13- or 14-membered aromatic or heteroaromatic ring system containing 0–3 heteroatoms selected from O, N, or S; each of which rings is optionally substituted with 1–3 lower alkyl, substituted alkyl, substituted alkynyl, =O, —NO$_2$, halogen, hydroxy, alkoxy, OCH(COOH)$_2$, cyano, —NZZ, acylamino, phenyl, benzyl, phenoxy, benzyloxy, heteroaryl, or heteroaryloxy; each of said phenyl, benzyl, phenoxy, benzyloxy, heteroaryl, and heteroaryloxy is optionally substituted with 1–3 substituents selected from lower alkyl, alkenyl, alkynyl, halogen, hydroxy, alkoxy, cyano, phenyl, benzyl, benzyloxy, carboxamido, heteroaryl, heteroaryloxy, —NO$_2$ or —NZZ (wherein Z is independently H, lower alkyl or cycloalkyl, and -ZZ may be fused to form a cyclic ring with nitrogen).

The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

"Arylalkyl" means an alkyl residue attached to an aryl ring. Examples are benzyl, phenethyl and the like.

"Heteroarylalkyl" means an alkyl residue attached to a heteroaryl ring. Examples include, e.g., pyridinylmethyl, pyrimidinylethyl and the like.

"Heterocycloalkyl" means a cycloalkyl where one to two of the methylene (CH$_1$) groups is replaced by a heteroatom such as O, NZ' (wherein Z is H or alkyl), S or the like; with the proviso that except for nitrogen when two heteroatoms are present, they must be separated by at least one carbon atom. Examples of heterocycloalkyl include tetrahydrofuranyl, piperidine, dioxanyl and the like.

"Alkylcarbonyl" means —C(O)R", wherein R" is alkyl.

"Substituted" alkyl, alkenyl, alkynyl, cycloalkyl, or heterocycloalkyl means alkyl, alkenyl, alkynyl, cycloalkyl, or heterocycloalkyl wherein up to three H atoms on each C atom therein are replaced with halogen, hydroxy, loweralkoxy, carboxy, carboalkoxy, carboxamido, cyano, carbonyl, —NO$_2$, —NZZ; alkylthio, sulfoxide, sulfone, acylamino, amidino, phenyl, benzyl, heteroaryl, phenoxy, benzyloxy, heteroaryloxy, or substituted phenyl, benzyl, heteroaryl, phenoxy, benzyloxy, or heteroaryloxy.

"Aa" represents an amino acid, naturally occurring or synthetic, and is intended to include the racemates and all optical isomers thereof. The amino acid side chains of Aa include, e.g., methyl (alanine), hydroxymethyl (serine), phenylmethyl (phenylalanine), thiomethyl (cysteine), carboxyethyl (glutamic acid), etc. Primary and secondary amino acids are intended to include alanine, asparagine, N-.beta.-trityl-asparagine, aspartic acid, aspartic acid-beta-t-butyl ester, arginine, N$^g$-Mtr-arginine, cysteine, S-trityl-cysteine, glutamic acid, glutamic acid-.gamma.-t-butyl ester, glutamine, N$^γ$-trityl-glutamine, glycine, histidine, N$^{im}$-trityl-histidine, isoleucine, leucine, lysine, N$^ε$-Boc-lysine, methionine, phenylalanine, proline, serine, O-t-butyl-serine, threonine, tryptophan, N$^{in}$-Boc-tryptophan, tyrosine, valine, sarcosine, L-alanine, chloro-L-alanine, 2-aminoisobutyric acid, 2-(methylamino)isobutyric acid, D,L-3-aminoisobutyric acid, (R)-(-)-2 aminoisobutyric acid, (S)-(+)-2-aminoisobutyric acid, D-leucine, L-leucine, D-norvaline, L-norvaline, L-2-amino-4-pentenoic acid, D-isoleucine, L-isoleucine, D-norleucine, 2,3-diaminopropionic acid, L-norleucine, D,L-2-aminocaprylic acid, .beta.-alanine, D,L-3-aminobutyric acid, 4-aminobutyric acid, 4-(methylamino)butyric acid, 5-aminovaleric acid, 5-aminocaproic acid, 7-aminoheptanoic acid, 8-aminocaprylic acid, 11-aminodecanoic acid, 12-aminododecanoic acid, carboxymethoxylamine, D-serine, D-homoserine, L-homoserine, D-allothreonine, L-allothreonine, D-threonine, L-threonine, D,L-4-amino-3-hydroxybutyric acid, D-,L-3-hydroxynorvaline, (3S,4S)-(-)-statine, 5-hydroxy-D,L-lysine, 1-amino-1-cyclopropanecarboxylic acid, 1-amino-1-cyclopentanecarboxylic acid, 1-amino-1-cyclohexanecarboxylic acid, 5-amino-1,3-cyclohexadiene-1-carboxylic acid, 2-amino-2-norbomanecarboxylic acid, (S)-(-)-2-azetidinecarboxylic acid, cis-4-hydroxy-D-proline, cis-4-hydroxy-L-proline, trans-4-hydroxy-L-proline, 3,4-dehydro-D,L-proline, 3,4-dehydro-L-proline, D-pipecolinic acid, L-pipecolinic acid, nipecotic acid, isonipecotic acid, mimosine, 2,3-diaminopropionic acid, D,L-2,4-diaminobutyric acid, (S)-(+)-diaminobutyric acid, D-ornithine, L-ornithine, 2-methylornithine, N-.epsilon.-methyl-L-lysine, N-methyl-D-aspartic acid, D,L-2-methylglutamic acid, D,L-2-aminoadipic acid, D-2-aminoadipic acid, L-2-aminoadipic acid, (+/−)-3-aminoadipic acid, D-cysteine, D-penicillamine, L-penicillamine, D,L-homocysteine, S-methyl-L-cysteine, L-methionine, D-ethionine, L-ethionine, S-carboxymethyl-L-cysteine, (S)-(+)-2-phenylglycine, (R)-(-)-2-phenylglycine, N-phenylglycine, N-(4-hydroxyphenyl)glycine, D-phenylalanine, (S)-(-)indoline-2-carboxylic acid, α-methyl,D,L-phenylalanine, α-methyl-D,L-phenylalanine, D-homophenylalanine, L-homophenylalanine, D,L-2-fluorophenylglycine, D,L-2-fluorophenylalanine, D,L-3-fluorophenylalanine, D,L-4- fluorophenylalanine, D,L-4-chlorophenylalanine, L-4-chlorophenylalanine, 4-bromo-D,L-phenylalanine, 4-iodo-D-phenylalanine, 3,3',5-triiodo-L-thyronine, (+)-3,3',5-triiodo-L-thyronine, D-thyronine, L-thyronine, D,L-tyrosine, D-4-hydroxyphenylglycine, D-tyrosine, L-tyrosine, O-methyl-L-tyrosine, 3-fluoro-D,L-tyrosine, 3-iodo-L-tyrosine, 3-nitro-L-tyrosine, 3,5-diiodo-L-tyrosine, D,L-dopa, L-dopa, 2,4,5-trihydroxyphenyl-D,L-alanine, 3-amino-L-tyrosine, 4-amino-D-phenylalanine, 4-amino-L-phenylalnine, 4-amino-D,L-phenylalanine, 4-nitro-L-phenylalanine, 4-nitro-D,L-phenylalanine, 3,5-dinitro-L-tyrosine, D,L-.alpha.-methyltyrosine, L-.alpha.-methyltyrosine, (−)-3-(3,4-dihydroxyphenyl)-2-methyl-L-alanine, D,L-threo-3-phenylserine, trans-4-minomethyl) cyclohexane carboxylic acid, 4-(aminomethyl)benzoic acid, D,L-3-aminobutyric acid, 3-aminocyclohexane carboxylic acid, cis-2-amino-1-cyclohexane carboxylic acid, gamma-amino-beta-(p-chlorophenyl)butyric acid (Baclofen), D,L-3-aminophenylpropionic acid, 3-amino-3-(4-chlorophenyl) propionic acid, 3-amino-3-(2-nitrophenyl)propionic acid, and 3-amino-4,4,4-trifluorobutyric acid.

An "alkylaryl group" refers to an alkyl (as described above), covalently joined to an aryl group (as described above).

"Carbocyclic aryl groups" are groups wherein the ring atoms on the aromatic ring are all carbon atoms. The carbon atoms are optionally substituted.

"Heterocyclic aryl groups" are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted.

An "amide" refers to an —C(O)—NH—, where Z is either alkyl, aryl, alklyaryl or hydrogen.

A "thioamide" refers to —C(S)—NH—Z, where Z is either alkyl, aryl, alklyaryl or hydrogen.

An "ester" refers to an —C(O)—OZ', where Z' is either alkyl, aryl, or alklyaryl.

An "amine" refers to a —N(Z'')Z''', where Z'' and Z''', is independently either hydrogen, alkyl, aryl, or alklyaryl, provided that Z'' and Z''' are not both hydrogen.

An "ether" refers to Z—O—Z, where Z is either alkyl, aryl, or alkylaryl.

A "thioether" refers to Z-S-Z, where Z is either alkyl, aryl, or alkylaryl.

A "cyclic molecule" is a molecule which has at least one chemical moiety which forms a ring. The ring may contain three atoms or more. The molecule may contain more than one cyclic moiety, the cyclic moieties may be the same or different.

A "linear molecule" does not contain a ring structure. However, the molecule may be straight or branched.

An "active site" of a protein refers to the specific area on the surface of a protein, e.g., an enzyme molecule or surface membrane receptor, to which a binding molecule, e.g. substrate or reciprocal ligand. is bound and results in a change in the ligand, e.g. substrate or complex formation with the protein as a result of ligand binding. For a receptor, the conformation may change, the protein may become susceptible to phosphorylation or dephosphorylation or other processing. For the most part, the active site will be the site(s) of an enzyme where the substrate and/or a cofactor bind, where the substrate and cofactor undergo a catalytic reaction, where two proteins form a complex, e.g. the site at which a G protein binds to a surface membrane receptor, two kringle structures bind, sites at which transcription factors bind to other proteins, sites at which proteins bind to specific nucleic acid sequences, etc. In the case of a membrane receptor, the active site will be the external site to a membrane, where the ligand binds and causes transduction of a signal.

The "activity-based probes" or "ABP"s of the invention are chemical reagents that are polyfunctional molecules for non-competitive or substantially irreversible binding to a target protein and inhibiting the action of the target protein. The ABPs will comprise at least a reactive functionality and a ligand and have an affinity for a related group of proteins, whereby the ABP will bind to the target protein and substantially inactivate the protein, and the ligand will permit detection and/or isolation.

In referring to affinity for an ABP to a target protein, one is concerned with the on-rate of the ABP with the target protein, since there is no off-rate, where the ABP covalently bonds to the target protein. One can determine relative on-rates between ABPs by having less than a stoichiometric amount of the target protein as compared to the total amount of a plurality of ABPs and then measuring the relative amounts of the conjugates for each of the ABPs. In this way one can obtain a measure of the relative activity of each of the ABPs toward the target protein, which for the purposes of this invention may be considered the affinity, if not the binding affinity, of the ABP for the target protein.

Exemplary protein targets described herein include enzymes, included in the groups oxidoreductases, hydrolases, ligases, isomerases, transferases, and lyases and include such enzymes or enzyme groups as serine hydrolases, metallo-hydrolases, dehydrogenases, e.g. alcohol and aldehyde dehydrogenases, and nucleotide triphosphate (NT)-dependent enzymes, although, the invention envisions ABPs which recognize any protein, e.g., enzyme, family. Other proteins include proteins that bind to each other or to nucleic acids, such as transcription factors, kringle structure containing proteins, nucleic acid binding proteins, G-protein binding receptors, cAMP binding proteins, etc. The structure of ABPs of the invention is described more fully below.

An "active protein" of the invention refers to a protein, e.g., enzyme, in its normal wild-type conformation, e.g. a catalytically active state, as opposed to an inactive state. The active state allows the protein, to function normally. An inactive state may be as a result of denaturation, inhibitor binding, either covalently or non-covalently, mutation, secondary processing, e.g. phosphorylation or dephosphorylation, etc. Functional states of proteins or enzymes as described herein may be distinct from the level of abundance of the same proteins or enzymes. An active site is an available wild-type conformation at a site that has biological activity, such as the catalytic site of an enzyme, a cofactor-binding site, the binding site of a receptor for its ligand, and the binding site for protein complexes, for example. In many instances, one is interested in knowing the level of availability of such sites. Targets of interest will be particularly enzymes, other proteins include receptors, transcription factors, G-proteins, and the like.

The subject systems are useful for, among other things, developing new drugs and identifying new drug targets. One embodiment of the subject invention is especially useful for rapidly generating and developing large numbers of drug candidate molecules. The invention is useful for systematically synthesizing a large number of molecules that may vary greatly in their chemical structure or composition, or that may vary in minor aspects of their chemical structure or composition. The invention is also useful for randomly generating a large number of drug candidates, and later optimizing those candidates that show the most medicinal promise. The combinatorial libraries of the present invention may also be screened for diagnostically useful compounds. By diagnostically useful is meant that the compound can be used to indicate the presence of a particular disease in a human or animal.

The combinatorial libraries of the present invention may be screened for pharmacologically active compounds, including analogs, that is compounds that can affect the biological status of a biological system, usually a cellular system. The biological system will depend on the use of a biological source that will include cells and/or viruses. By pharmacologically active is meant that a compound may effect the function of a protein, e.g, an enzyme, including physiological process such as signal transduction by a cellular receptor, initiation, cessation or modulation of an immune response, modulation of heart function, nervous system function, or any other organ or organ system. A pharmacologically active compound may also stimulate or inhibit the activity of a bacteria, virus, fungus, or other infectious agent. A pharmacologically active compound may modulate the effects of a disease, that is prevent or decrease the severity of or cure a disease such as cancer, diabetes, atherosclerosis, high blood pressure, Parkinson's disease and other disease states. Screening for pharmacological activity may be performed by assays as would be known in the art, depending on the function or activity to be assessed. Compounds which have been shown to be pharmacologically active compounds may be formulated for therapeutic administration by methods known in the art. Methods have been reported in the literature by which individual members of combinatorial libraries may be encoded by "tagging molecules" ("tags" or "labels"). See, for example, U.S. Pat. Nos. 5,721,099 and 6,001,579. Thus, a single molecular structure synthesized on a resin bead, for instance, is uniquely defined by a series of other, readily detectable molecules also bound to a bead. Individual beads are treated to release their library member, by a process which does not displace the tag, and following identification of this compound as an "active" in a biological screen, the tags are released and analyzed to deduce the identity of the "hit". To allow for maximum diversity in a library it is critical that the chemistry used to introduce the tags is tolerated by a wide range of functionality. Thereby, introduction of the tagging molecule does not lead to undesired elaboration of the library structure, or alternatively, place limits upon the chemistry used to construct the library. Similarly, if the tag is removed prior to the library member, the conditions for removal of the tag does not destroy or react in some manner with the designed molecule.

The material upon which the combinatorial syntheses of the present invention are performed are referred to as solid supports, beads or resins. These terms are intended to include beads, pellets, disks, fibers, gels, or particles such as cellulose beads, pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, poly-acrylamide beads, latex beads, dimethylacrylamide beads optionally cross-linked with N,N'-bis-acryloyl ethylene diamine, glass particles coated with hydrophobic polymer, and the like, e.g., material having a rigid or semi-rigid surface; and soluble supports such as low molecular weight non-cross-linked polystyrene.

By "biological status" is intended to include mRNA profile, protein profile, total and/or active, spatial distribution profile of the proteins and mRNA, maturity of cells, population of surface membrane proteins, amount and spatial distribution of complexes, amount of ligands present, bound and unbound, lipid population, processing of proteins, such as glycosylation, methylation, acylation, phosphorylation, ubiquination, farnesylation, etc., those differences that distinguish cellular populations.

Some of the compounds described herein contain one or more asymmetric centers and may thus give rise to enantiomers, diastereomers, and other stereoisometric forms that may be defined, in terms of absolute stereochemistry, as (R)- or (S)- or, as (D)- or (L)- for amino acids. The present invention is meant to include all such possible diastereomers, as well as, their racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers. Likewise, all tautomeric forms are also intended to be included.

Activity-based probes (ABPs) are provided for specific reaction with the active site of one or more target proteins, where the target protein is a member of a class of proteins, particularly enzymes, for detection of the presence and quantitation of one or more active members. The ABPs have a common electrophile whose environment is changed in each of the ABPs to provide a different reactivity with different target proteins. The probes may be divided into four general regions: (1) a functional group (F) that specifically and covalently bonds to the active site of a protein; (2) a label or ligand (hereinafter collectively referred to as "ligand") for sequestering and detecting the conjugate of the ABP and the active protein (X) 3) a linker L, between the F and the L; and 4) binding moiety or affinity label, that may be associated with or part of the linker region and/or the functional group (R). A linker is a bond or chemical group used to link one moiety to another, serving as a divalent bridge, where it provides a group between two other chemical moieties. Binding or affinity moiety refers to a chemical group, which may be a single atom, that is conjugated to the reactive functional group or associated with the linker, as a side chain or in the chain of the linker, and provides enhanced binding affinity for protein targets. A ligand refers to a molecule that can be used to detect and/or capture the ABP in combination with any other moieties that are bound strongly to the ligand so as to be retained in the process of the reaction of the functional group with the target active protein. The ABP may include a chemically reactive functionality, not found in proteins, that will react with a reciprocal functionality, e.g. vic.-diols with boronic acid, aldehydes and ketones, etc. These reactive functionalities may be used to bind to a ligand after reaction with the target protein. In some embodiments described herein, the ABP may be truncated and lack the ligand, but will always have a functional group, F, a linker, L and an R group (binding moiety), but no ligand, X (see FIG. 1).

The ABP will have an affinity for an active site, which may be specific for a particular active site or generally shared by a plurality of related proteins. The affinity may result from the functional group, the linker, or the binding moiety or combination thereof. For drug discovery, one may be interested in specificity for a single target, while for proteome analysis, one will usually be interested in binding to a plurality of targets that are related.

Exemplary Fs as used in an ABP of the invention include an alkylating agent, acylating agent, ketone, aldehyde, sulphonate or a phosphorylating agent. Examples of particular Fs include, but are not limited to fluorophosphonyl, fluorophosphoryl, fluorosulfonyl, alpha-haloketones or aldehydes or their ketals or acetals, respectively, alpha-haloacyls, nitriles, sulfonated alkyl or aryl thiols, iodoacetylamide group, maleimides, sulfonyl halides and esters, isocyanates, isothiocyanantes, tetrafluorophenyl esters, N-hydroxysuccinimidyl esters, acid halides, acid anhydrides, unsaturated carbonyls, alkynes, hydroxamates, alpha-halomethylhydroxamates, aziridines, epoxides, or arsenates and their oxides. Sulfonyl groups may include sulfonates, sulfates, sulfinates, sulfamates, etc., in effect, any reactive functionality having a sulfur group bonded to two oxygen atoms. Epoxides may include aliphatic, aralkyl, cycloaliphatic and spiro epoxides, the latter exemplified by fumagillin, which is specific for metalloproteases.

Figure 2:
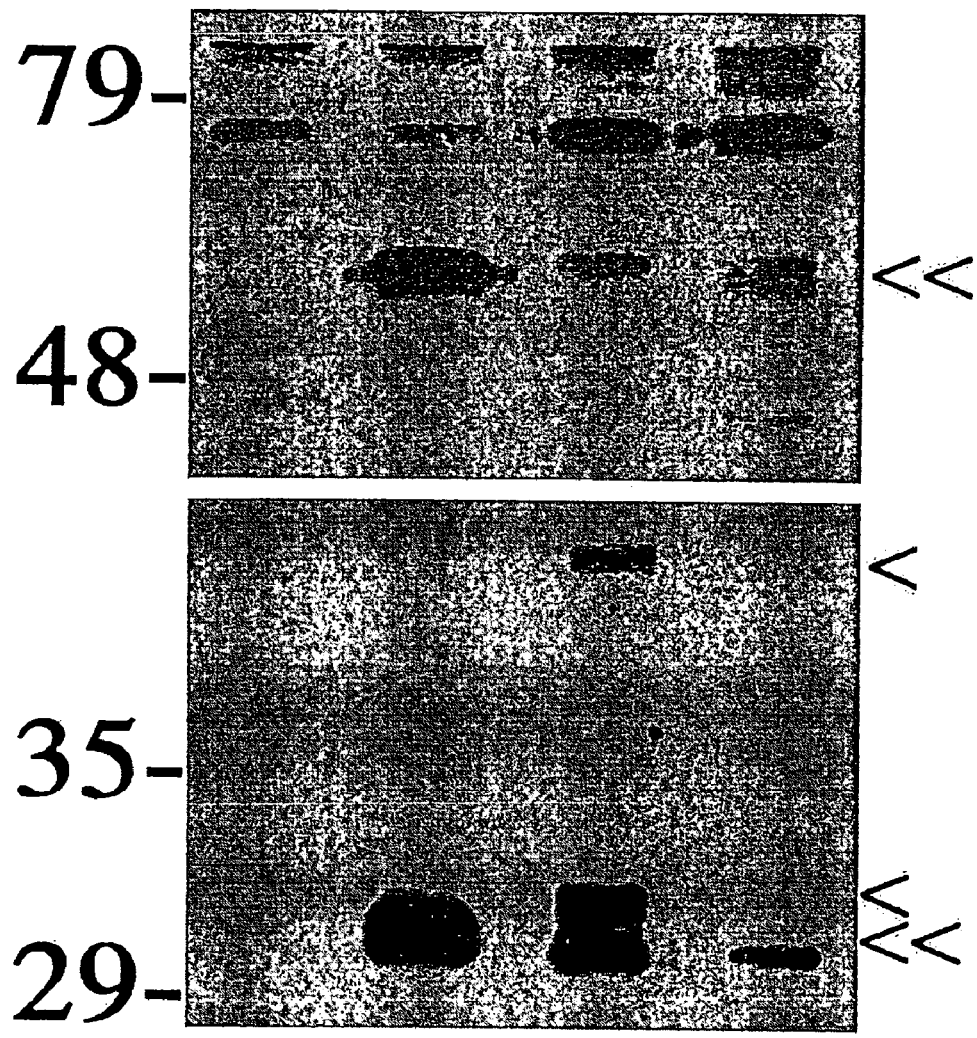
FIG. 2 shows a protein profile from a testis extract on a reducing SDS-PAGE with a pyridyl sulfonate ABP, with (−) and without heating, and a methyl sulfonate ABP, with (−) and without heating.

The ABPs of the subject invention may be illustrated by the following formula:

where the symbols are as defined previously and the asterisk intends that R may be included in F or L and X is bonded to L, more specifically:
wherein:
X is a ligand present prior to formation of said product or added to a reactive functionality to provide said ligand, said ligand having the same chemical structure for each of said members of said library;
L is a bond or linking group, which is the same in each of the members of said library;
F is a functional group reactive at an active site of a protein member, which functional group comprises the same reactive functionality in each of the members of said library; and
R is a group of less than 1 kDal, that is different in each of the members of the library;
the * intends that R is a part of F or L; and
wherein members of said library have different on rates with said protein member. For example, when X is biotin or any ligand, L is any linker of varied composition and length, F is a sulfonate and R is a pyridyl group, a distinct protein profile is observed as compared with the same ABP wherein the R group is methyl (FIG. 2). Thus by varying R when bonded to a sulfonyl group, different binding profiles will be obtained, so that one can look for specificity, which may lead to designing a drug based on the structure of R or look for binding to related target proteins for proteome analysis.

Figure 3:
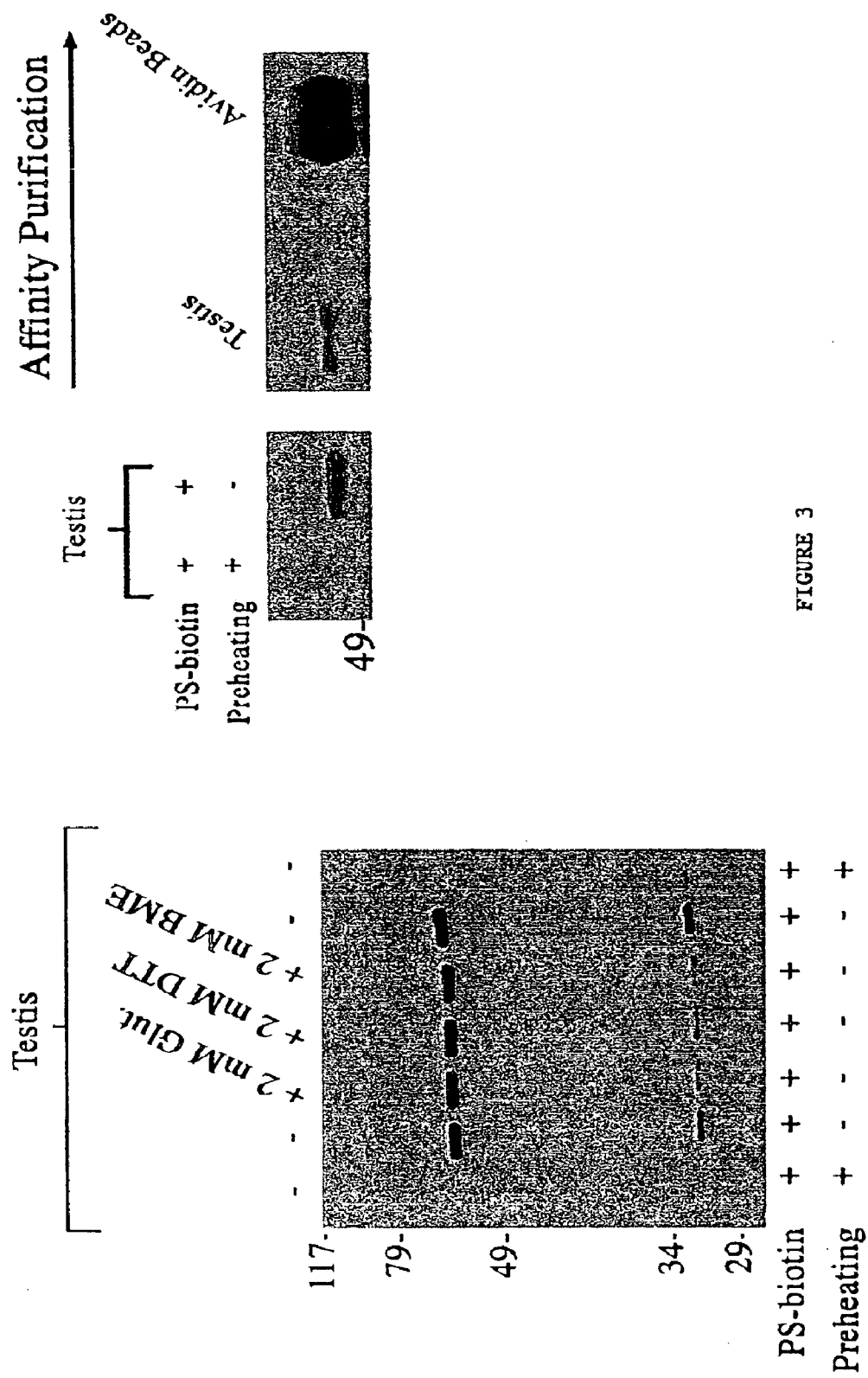
FIG. 3 shows the results of a non-directed tagged library of sulfonates (aryl) as ABPs for the identification of a novel ADH enzyme.
Figure 7:
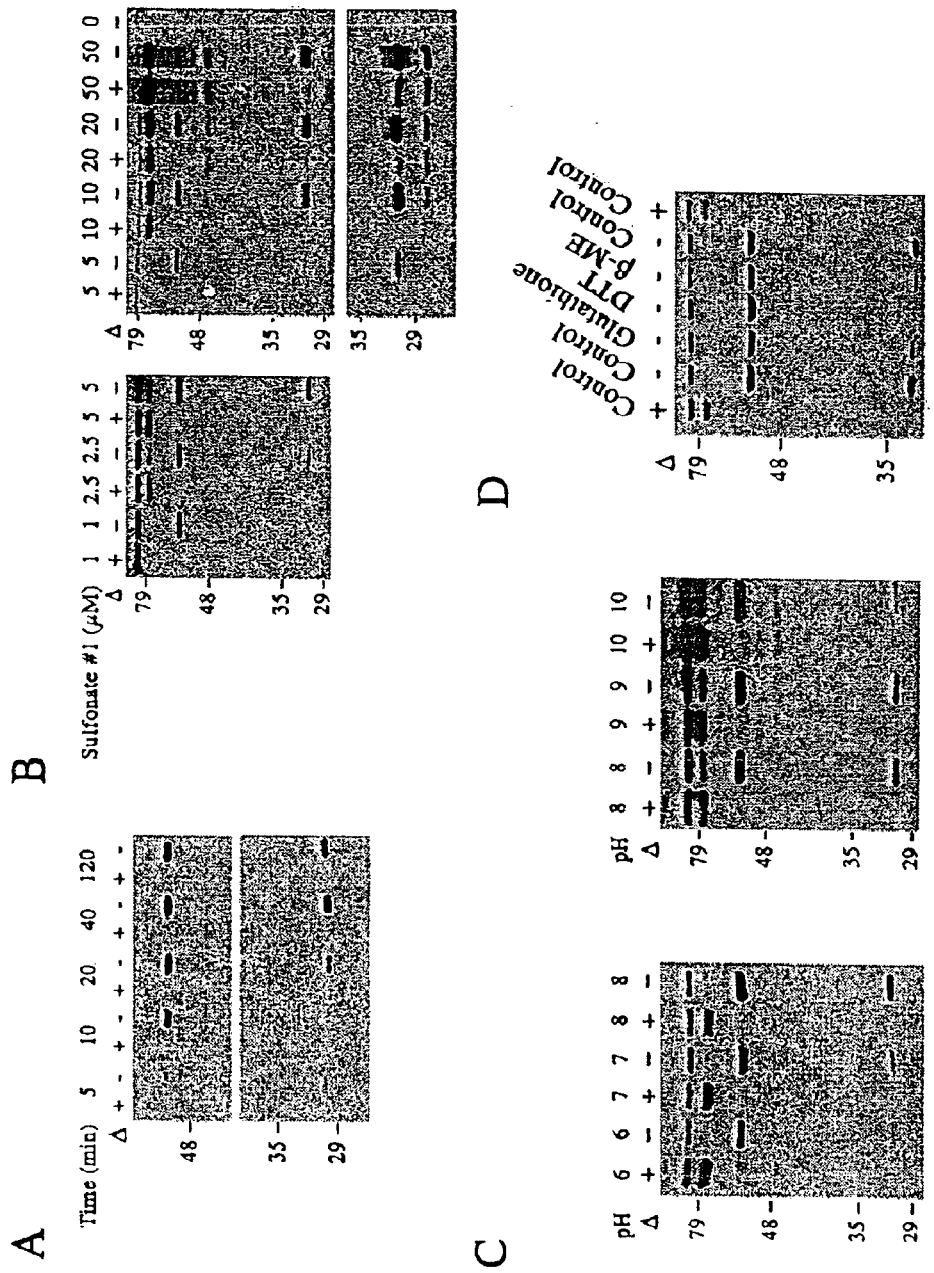
FIG. 7 shows parameters that affect the proteome reactivity of pyridylsulfonate 1. Time-dependence of 1-proteome reaction (5 μM of 1, 0.5 μg/μL protein, 50 mM Tris.HCl, pH 8.0). B, Concentration-dependence of 1-proteome reaction. Left panel, 1, 2.5, and 5 μM concentrations of 1 were reacted with the testis proteome (0.5 μg/μL protein, 50 mM Tris.HCl, pH 8.0, 30 min reaction). Right panel, 5, 10, 20, and 50 μM concentrations of 1 were reacted with the testis proteome (0.5 μg/μL protein, 50 mM Tris.HCl, pH 8.0, 30 min reaction). Short (upper right panel) and long (lower right panel) film exposures of these reactions are shown. Note the presence of an endogenous 80 kDa avidin-reactive protein in the lane containing an untreated testis proteome. C, pH-dependence of 1-proteome reaction (5 μM of 1, 0.5 μg/μL protein, 30 min reaction). Left panel, reactions conducted from pH 6.0–8.0. Right panel, reactions conducted from pH 8.0–10.0. D, Thiol-dependence of 1-proteome reaction. Control reactions were conducted under standard conditions. Each thiol (2 mM) was added to the proteome prior to the addition of 1.

Illustrative of the method is the use of a reactive functionality having a leaving group that is varied to provide the combinatorial library for identifying a chemical compound which affects the activity of a protein. The method includes contacting a combinatorial chemical library with a biological sample, where the library comprises a plurality of differing functional groups (F—R) reactive with an active protein, wherein, for example, a sulfonate ester can have R as any group, such as alkyl, heterocyclic, such as pyridyl, substituted pyridyl, imidazole, pyrrole, thiophene, furan, azole, oxazole, aziridine, etc., aryl, substituted aryl, amino acid or peptidyl, oligonucleotide or carbohydrate group; and detecting an effect on a biological activity in a biological sample (e.g., inhibition of cell proliferation or inhibition of an enzyme activity). One can take an ABP identified by screening the libraries as described herein and confirm the specificity of the ABP for the protein. For example, as exemplified in FIG. 3, one can take an individual ABP identified from a library of sulfonates and identify through MALDI mapping, a target enzyme, as shown in the Experimental section, aldehyde dehydrogenase (ADH). An ABP lacking X, or a label (e.g., biotin) is utilized to confirm the inhibition of ADH activity by the specific ABP identified. To further characterize the bond between the sulfonate ABP and the ADH, for example, one can include modifying agents in an assay for detection of inhibition of ADH activity. For example, in FIG. 7, addition of a variety of free thiols, including glutathione (GSH or glut), dithiothreitol (DTT), or α-mercaptoethanol (BME), did not quench the bonding of the ABP/ADH, and provides further information as to the bond between the ABP and newly identified ADH. Other protein effectors, thiols, metals, chelators (e.g., EDTA), ATP, calcium and the like can be added to reactions between an ABP and protein target to provide further characterization.

The ligand portion permits capture of the conjugate of the target protein and the probe. The ligand may be displaced from the capture reagent by addition of a displacing ligand, which may be free ligand or a derivative of the ligand, or by changing solvent (e.g., solvent type or pH) or temperature conditions or the linker may be cleaved chemically, enzymatically, thermally or photochemically to release the isolated materials (see discussion of the linker moiety, below).

Examples of ligands (including labels), X, include, but are not limited to, biotin, deiminobiotin, dethiobiotin, vicinal diols, such as 1,2-dihydroxyethane, 1,2-dihydroxycyclohexane, etc., digoxigenin, maltose, oligohistidine, glutathione, 2,4-dintrobenzene, phenylarsenate, ssDNA, dsDNA, a peptide of polypeptide, a metal chelate, a saccharide, rhodamine or fluorescein, or any hapten to which an antibody can be generated. Examples of ligands and their capture reagents include but are not limited to: dethiobiotin or structurally modified biotin-based reagents, including deiminobiotin, which bind to proteins of the avidin/streptavidin family, which may, for example, be used in the forms of strepavidin-Agarose, oligomeric-avidin-Agarose, or monomeric-avidin-Agarose; any 1,2-diol, such as 1,2-dihydroxyethane (HO—$CH_2$—$CH_2$—OH), and other 1,2-dihyroxyalkanes including those of cyclic alkanes, e.g., 1,2-dihydroxycyclohexane which bind to an alkyl or aryl boronic acid or boronic acid esters, such as phenyl-B(OH)$_2$ or hexyl-B(OEthyl)$_2$ which may be attached via the alkyl or aryl group to a solid support material, such as Agarose; maltose which binds to maltose binding protein (as well as any other sugar/sugar binding protein pair or more generally to any ligand/ligand binding protein pairs that has properties discussed above); a hapten, such as the dinitrophenyl group, for any antibody where the hapten binds to an anti-hapten antibody that recognizes the hapten, for example the dinitrophenyl group will bind to an anti-dinitrophenyl-lgG; a ligand which binds to a transition metal, for example, an oligomeric histidine will bind to Ni(II), the transition metal capture reagent may be used in the form of a resin bound chelated transition metal, such as nitrilotriacetic acid-chelated Ni(II) or iminodiacetic acid-chelated Ni(II); glutathione which binds to glutathione-S-transferase.

In general, any affinity label-capture reagent commonly used for affinity enrichment which meets the suitability criteria discussed above can be used in the method of the invention. Biotin and biotin-based affinity tags are particularly illustrated herein. Of particular interest are structurally modified biotins, such as deiminobiotin or dethiobiotin, which will elute from avidin or streptavidin (strept/avidin) columns with biotin or under solvent conditions compatible with ESI-MS analysis, such as dilute acids containing 10–20% organic solvent. It is expected that deiminobiotin tagged compounds will elute in solvents below about pH 4.

Figure 6:
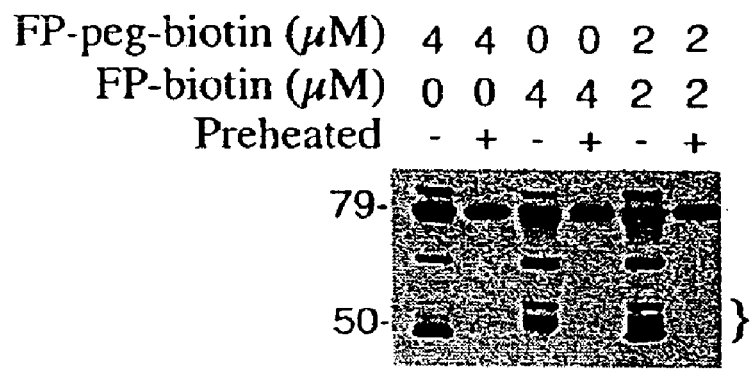
FIG. 6 shows protein profiles for FP-PEG-biotin compared with protein profiles for FP-biotin.
Figure 6:
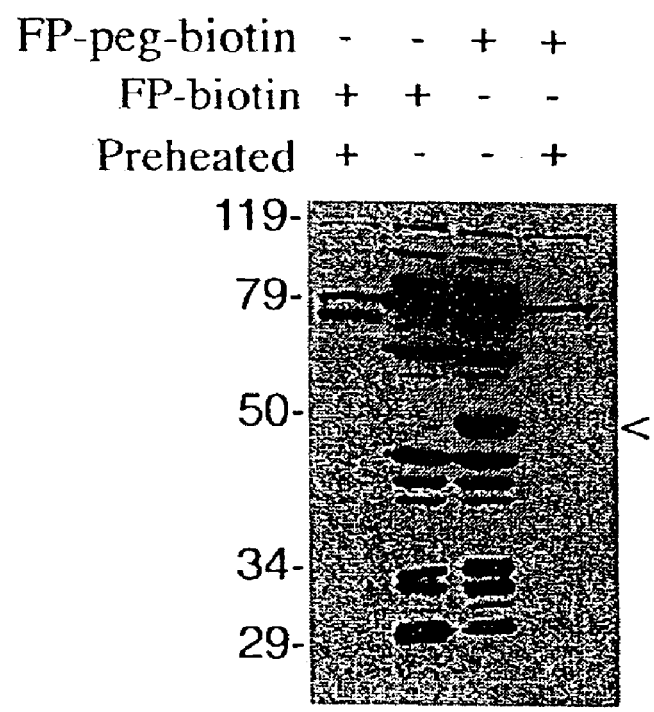

The linker group, while potentially can be a bond, is preferred to be other than a bond. The linker can be a cleavable linker that is cleaved, for example, by thermal, chemical or photochemical reaction. The choice of linker for the label and the functional group will be part of the synthetic strategy, since depending on the synthetic strategy, the linking group can result in a residual functionality on the product upon release from the support. It will usually be difficult, but feasible, to further modify the product after detachment from the bead. In designing the synthetic strategy, one can use a functionality to be retained in the product as the point of attachment for the linking group. Alternatively, when permitted by the nature of the product, one could use a cleavage or detachment method which removes the linking functionality, e.g., an arylthioether or silyl with a metal hydride or acid. Since in many cases, the synthetic strategy will be able to include a functionalized site for linking, the functionality can be taken advantage of in choosing the linking group. In some instances it may be desirable to have different functionalities at the site of linking the product to the support, which may necessitate using different modes of linking, which modes must accommodate either the same detachment method or different detachment methods which may be carried out concurrently or consecutively, e.g., irradiation with light and acid hydrolysis. The choice of linker, as with the choice of an R group, has been shown to alter the specificity of an ABP. For example, a linker for FP biotin, described in the Examples herein (see also FIG. 1), and a linker comprising PEG, have distinct specificities and provide distinct protein profiles (see FIG. 6). Thus, one of skill in the art can select the linker portion of the ABP in order to provide additional specificity of the ABP for a particular protein or protein class.

Photocleavable groups in the linker may include the 1-(2-nitrophenyl)ethyl group. Thermally labile linkers may include a double-stranded duplex formed from two complementary strands of nucleic acid, a strand of a nucleic acid with a complementary strand of a peptide nucleic acid, or two complementary peptide nucleic acid strands which will dissociate upon heating. Cleavable linkers also include those that have disulfide bonds, acid or base labile groups, including diarylmethyl or trimethylarylmethyl groups, silyl ethers, carbamates, oxyesters, thioesters, thionoesters and alpha-fluorinated amides and esters. Enzymatically cleavable linkers can contain protease-sensitive amides or esters, beta-lactamase-sensitive beta-lactam analogs and linkers that are nuclease-cleavable or glycosidase cleavable.

Linker groups include among others, ethers, polyethers, diamines, ether diamines, polyether diamines, amides, polyamides, polythioethers, disulfides, silyl ethers, alkyl or alkenyl chains (straight chain or branched and portions of which may be cyclic) aryl, diaryl or alkyl-aryl groups. While normally amino acids and oligopeptides are not preferred, when used they will normally employ amino acids of from 2–3 carbon atoms, i.e. glycine and alanine. Aryl groups in linkers can contain one or more heteroatoms (e.g., N, O or S atoms). Linkages also include substituted benzyl ethers, esters, acetals or ketals, diols, and the like (See, U.S. Pat. No. 5,789,172 for a list of useful functionalities and manner of cleavage, herein incorporated by reference). The linkers, when other than a bond, will have from about 1 to 60 atoms, usually 1 to 30 atoms, where the atoms include C, N, O, S, P, etc., particularly C, N and O, and will generally have from about 1 to 12 carbon atoms and from about 0 to 8, usually 0 to 6 heteroatoms. The atoms are exclusive of hydrogen in referring to the number of atoms in a group, unless indicated otherwise.

The linker and/or the ligand may be isotopically labeled, for example by substitution of one or more atoms in the linker with a stable isotope. For example, $^1$H can be substituted with $^2$H or $^{12}$C can be substituted with $^{13}$C. Alternatively one may substitute one atom for another, such as H with F, use unsaturation to provide a different mass, or other known means. While ligands or linking groups may have different isotopic distributions, for the purposes of this invention they will be considered to be of the same chemical composition, where the atomic numbers of the atoms and their organization in the ligands or linking groups is the same. Therefore, in one aspect, the method of the invention provides for labeling of the ligand and/or linker to facilitate quantitative analysis by mass spectrometry of the amounts of proteins in different samples or in samples subjected to different conditions (e.g., in the presence and absence of a drug). Further, the label or linker can be non-radioisotopically labeled, e.g, with a fluorophore. In one aspect, the label produces an electromagnetic signal.

The process and compositions described in WO00/11208, which is specifically incorporated by reference herein, may be used with the subject invention. In the application, one uses an affinity tagged, substantially chemically identical and differentially isotopically labeled probe, where the conjugates or fragments thereof are identified by mass spectrometry. The ratio of the different isotopic probes for each of the proteins with which the probes have reacted provides for the relative quantities of the individual proteins.

Linkers may be varied widely depending on their function, including alkyleneoxy and polyalkyleneoxy groups, where alkylene is of from 2–3 carbon atoms, methylene and polymethylene, polyamide, polyester, and the like, where individual monomers will generally be of from 1 to 6, more usually 1 to 4 carbon atoms. The oligomers will generally have from about 1 to 10, more usually 1 to 8 monomeric units. The monomeric units may be amino acids, both naturally occurring and synthetic, oligonucleotides, both naturally occurring and synthetic, condensation polymer monomeric units and combinations thereof. Alteration in the linker region has been shown to alter the specificity of the ABP for a target protein or class of proteins (e.g., enzymes).

Since the combinatorial production of probes is intended to find probes specific for target proteins and/or probes that provide information about the active site of a protein, these probes will usually be modified so as to be identifiable. Also, there can be a cleavable site between the target protein and at least a portion of the probe, where the identifiable moiety of the probe can be released from the target protein. Once the probe has been identified, for example, by mass spectrometry, fluorometry, electrochemically, etc., or combination thereof, the single probe may then be used with the same proteome mixture. At this stage, the protein target(s) can then be determined by conventional ways, using immunoassays, if available, sequencing, mass spectrometry and the like. The affinity label will then provide a basis for the design of a drug specific for the target protein.

With the ABP compounds described herein, screening assays such as FACS sorting and cell lawn assays may be used. When ligand, X, is detached prior to evaluation, its relationship to its solid support can be maintained, e.g., by location within the grid of a standard 96-well plate or by location of activity on a lawn of cells. Whether the compounds are tested attached to or detached from, the solid supports, the tags attached to the solid support associated with bioactivity may then be decoded to reveal the structural or synthetic history of the active compound (see for example, Ohlmeyer et al., Proc. Natl. Acad. Sci. USA, 90, 10922–10926, 1993). The usefulness of such libraries as screening tools is demonstrated by Burbaum et al., (Proc. Natl. Acad. Sci. USA, 92, 6027–6031, 1995), who describe the assaying of encoded combinatorial libraries for, e.g., carbonic anhydrase inhibition. Even when none of the compounds in a particular assay are found to be active for a given screen, such lack of activity often, however, provides useful structure-activity information.

In one embodiment, the invention employs two different compositions, intact ABPs and truncated ABPs lacking the ligand. See FIG. 1. In most cases, the combination will employ combinatorial libraries that are being screened for bioactivity. For most intact ABPs containing ligands, it is difficult to obtain entry into an intact cell. Using electroporation, permeabilizing agents, or the like will change the status of the cell and could interfere with the assay. To use convenient ligands, such as biotin, one prepares two libraries, intact ABPs and truncated ABPs lacking the ligand. One then introduces the truncated ABPs under conditions that allow the truncated ABPs to enter the cell without significant disruption of the cell membrane. Any change in phenotype may be determined, such as apoptosis, proliferation, change in surface membrane proteins, inability to respond to ligands for cellular receptors, etc. If the change in phenotype is of interest, the cells may then be lysed and the lysate treated with the intact ABPs. In addition, one would use an inactivated lysate, to compare and select only those proteins that were conjugated in the active lysate and not conjugated in the inactivated lysate. The proteins to which the ABPs are conjugated can then be characterized in manners discussed in the specification and in the Experimental section. Alternatively, one may establish conditions for transport of the ABP into the cell without modifying the cell to change its response or choose lipophilic ligands or provide conditions where the ABPs will be entrained with another compound that provides permeability. In this way, one can determine conditions that will allow the screening of libraries where the ABPs will enter the cells without an undesirable change in the character of the cell. These approaches allow for the determination of ABPs that can serve as precursors in the design of drugs for specific binding to target proteins, while at the same time determining the effect on the phenotype of modifying the activity of the target protein. Of course, depending on the nature and size of the combinatorial library, one or more libraries may be used.

The above described method may also find application in determining whether the cellular environment affects the reaction of the ABP with a protein. One can use a radioactive label with the truncated ABP to identify whether the protein that reacted in the lysate also reacted in the cell. Alternatively, one may prepare monoclonal antibodies to the protein-ABP conjugates obtained in the lysate and use them to fish out the analogous protein from a cell that has been treated with the truncated ABP. By establishing that the truncated ABP bound to the same protein as the analogous ABP, one would establish that the specific affinity of the ABP provided the same intracellular activity or affinity as observed in the lysate.

Finally, one of skill in the art can identify the biological target in more detail by standard methods including SDS-PAGE or Western Blot analysis. As an illustrative example, the following protocol can be used to identify biological targets in a sample. After incubation of protein sample (0.5–2.5 mL, 0.5–1.0 mg/mL) with the ABPs, the sample is diluted to 2.5 mL in Tris or phosphate buffer and passed over a PD-10 size exclusion column to remove excess unreacted ABP. The protein is collected from the column in 3.5 mL of buffer, treated with SDS (final concentration of 0.5%), and heated for 10 min at 80° C. The sample is then diluted 2.5× and incubated with 100 $\mu$L of avidin agarose beads (Sigma) for 1–4 hours at room temp. The beads are then washed with several volumes of buffer to remove unbound protein and the ABP-labeled proteins are eluted with 100 $\mu$L of standard SDS-PAGE loading buffer by heating at 90° C. for 5 minutes. The eluted proteins are run on an SDS-PAGE gel and ABP-labeled proteins identified by staining and/or avidin blotting, excised from the gel, digested with trypsin, and the resulting peptide mixture characterized by MALDI and/or electrospray mass spectrometry. The mass spectrometric information is used in database searches to identify the ABP-labeled proteins.

Once one has established a probe, by combinatorial or other means, generally the probe may then be used to analyze a proteome for active protein(s). The probe may be specific for a single protein or more usually a related group of proteins. By related group of proteins is intended proteins that perform the same activity, as with enzymes that belong to the same group and catalyze the same reaction, e.g. hydrolysis, phosphorylation, oxidation, etc., and usually having one or more of the following characteristics: the same functionality at the active site; the same spatial orientation of functional groups that bind to the ligand; similar spatial structure and conformation; similar molecular weight; the same or similar cofactors or complexing proteins; and similar function. To enhance the distinction between active proteins and inactive proteins, special chemically reactive groups are employed.

A "chemically reactive group" is a moiety including a reactive functionality that does not react efficiently with the generally available functional groups of proteins, e.g. amino, hydroxy, carboxy, and thiol, but will react with a functionality present in a particular conformation on a surface. In some situations the reactive functionality will serve to distinguish between an active and an inactive protein. In other situations, the conformation of the chemically reactive group will bind to the specific conformation of the target protein(s), whereby with a slowly reactive functionality or one that requires activation, the predominant reaction will be at the active site. For example a photoactivatable group may be used such as a diazoketone, arylazide, psoralen, arylketone, arylmethylhalide, etc. any of which can bind non-selectively to the target protein, while the probe is bound to the active site. Olefins and acetylenes to which are attached electron withdrawing groups such as a sulfone, carbonyl, or nitro group may be used to couple to sulfhydryl groups.

A detectable label is a group that is detectable at low concentrations, usually less than micromolar, preferably less than nanomolar, that can be readily distinguished from other analogous molecules, due to differences in molecular weight, redox potential, electromagnetic properties, binding properties, and the like. The detectable label may be a hapten, such as biotin, or a fluorescer, or an oligonucleotide, capable of non-covalent binding to a complementary receptor other than the active protein; a mass tag comprising a stable isotope; a radioisotope; a metal chelate or other group having a heteroatom not usually found in biological samples; a fluorescent or chemiluminescent group preferably having a quantum yield greater than 0.1; an electroactive group having a lower oxidation or reduction potential than groups commonly present in proteins; a catalyst such as a coenzyme, organometallic catalyst, photosensitizer, or electron transfer agent; a group that affects catalytic activity such as an enzyme activator or inhibitor or a coenzyme.

Detectable labels may be detected directly by mass spectroscopy, detection of electromagnetic radiation, measurement of catalytic activity, potentiometric titration, cyclic voltametry, and the like. Alternatively labels may be detected by their ability to bind to a receptor thereby causing the conjugate to bind to the receptor. Binding of the conjugate to a receptor can be detected by any standard method such as ellipsometry, acoustic wave spectroscopy, surface plasmon resonance, evanescent wave spectroscopy, etc. when binding is to a surface, or by an immunoassay such as ELISA, FRET, SPA, RIA, in which the receptor may carry a label and an antibody to the active protein can be employed which may optionally carry a second label. Detectable labels may also be detected by use of separation methods such as HPLC, capillary or gel electrophoresis, chromatography, immunosorption, etc. In these methods the conjugate can be caused to bind to a member of an array of specific binding substances such as an array of antibodies where each member is an antibody for a specific active protein.

One aspect of the method of the invention is subjecting a portion of the sample to conditions that inactivate proteins in the sample. Significantly, information from studies with ABPs is preferable if one compares the level of protein conjugates in a portion of the sample that has been treated with inactivating conditions to a portion of the sample that contains active, wild-type or untreated proteins. Active wild-type proteins intend proteins with their natural conformation that are capable of carrying out binding and other functions, as appropriate. Other functions include enzymatic activity, ability to be modified, e.g. phosphorylation or dephosphorylation, acylation, etc., binding to cofactors or other proteins, functions that are necessary for biological activity. Differences between the protein profile in each of the active and the inactive portion are detected in order to identify active proteins, e.g. enzymes, in the sample. Inactivating conditions include chemical or physical means for inactivating, normally by denaturing the protein. For example, chemical means include denaturants such as organic solvents, harsh detergents, e.g. SDS, chaotropic.agents, e.g. urea, guanidinium chloride or isocyanate, etc., and other denaturing agents. Physical means include heat, freezing, electromagnetic radiation, shearing, drying, electrical discharge and the like. Inactivating agents that bind to the active site or an allosteric site affecting activity may bind covalently or non-covalently, with non-covalent binding being preferable. In a preferred embodiment, proteins in a sample are inactivated by heating, although other agents will be preferred if heating results in precipitation of the protein making it unavailable for reaction with an ABP.

Samples that can be analyzed by methods of the invention include biological samples, such as cell lysates, microsomal fractions, cell fractions, tissues, organelles, etc., and biological fluids including urine, sputum, saliva, blood, cerebrospinal fluid, tears, ejaculate, serum, pleural fluid, ascites fluid, stool, or a biopsy sample.

If the sample is impure (e.g., plasma, serum, stool, ejaculate, sputum, saliva, cerebrospinal fluid, or blood or a sample embedded in paraffin), it may be treated prior to employing a method of the invention, frequently to remove contaminants of the components of interest. Procedures include, for example, filtration, extraction, centrifugation, affinity sequestering, etc. Where the probes do not readily pass through a cellular membrane, intact or permeabilized, or where a lysate is desirable, the cells are treated with a reagent effective for lysing the cells contained in the fluids, tissues, or animal cell membranes of the sample, and for exposing the proteins contained therein and, as appropriate, partially separating the proteins from other aggregates or molecules such as microsomes, lipids, carbohydrates and nucleic acids in the sample. Methods for purifying or partially purifying proteins from a sample are well known in the art (e.g., Sambrook et al., Molecular Cloning: A Laboratory Manual, Cold Spring Harbor Press, 1989, herein incorporated by reference).

The samples may come from different sources and be used for different purposes. In many instances, the ABPs will be used to analyze a protein sample for active enzyme. This may include a relatively pure sample of the enzyme to determine the activity in relation to total protein of the sample. The sample may be a single cell or a mixture of cells, a neoplastic sample or other biopsy or tissue comprising a single cell type or a mixture of cell types, such as tissue from an organ, e.g. heart, lung, esophagus, kidney, brain, blood, etc., diseased tissue or healthy tissue, etc. The cells may be prokaryotic or eukaryotic, vertebrate or nonvertebrate, particularly mammalian and more particularly human. The cells or tissues, or lysates thereof may be prepared in a variety of ways, including fractionation, using chromatography, centrifugation, fluorescence activated cell sorting, dilution, dialysis, concentration, etc. The sample will usually be treated so as to preserve the activity of the target enzyme(s), so that the manner of treatment will be mild, ambient or lower temperatures will be used, particularly below 37° C., and other denaturing conditions will be avoided, such as organic solvents, or high salts.

Usually, a proteome will be analyzed. By a proteome is intended at least about 20% of total protein coming from a biological sample source, usually at least about 40%, more usually at least about 75%, and generally 90% or more, up to and including all of the protein obtainable from the source. Thus the proteome may be present in an intact cell, a lysate, a microsomal fraction, an organelle, a partially extracted lysate, biological fluid, and the like. The proteome will be a mixture of proteins, generally having at least about 20 different proteins, usually at least about 50 different proteins and in most cases 100 different proteins or more. In effect, the proteome is a complex mixture of proteins from a natural source and will usually involve having the potential of having 10, usually 20, or more proteins that are target proteins for the ABPs that are used to analyze the proteome profile. The sample will be representative of the target proteins of interest.

Generally, the sample will have at least about 0.05 mg of protein, usually at least about 1 mg of protein and may have 10 mg of protein or more, conveniently at a concentration in the range of about 0.1–10 mg/ml. The sample may be adjusted to the appropriate buffer concentration and pH, if desired. One or more ABPs may then be added, each at a concentration in the range of about 0.001 mM to 20 mM. After incubating the reaction, generally for a time for the reaction to go substantially to completion, generally for about 1–60 min, at a temperature in the range of about 20–40° C., the reaction may be quenched. The sample may now be assayed in different ways, depending upon the reagents to be used.

In one aspect of the invention, the method provides for quantitative measurement of specific active proteins in biological fluids, cells or tissues. Target identification can be applied to determine the global protein activity profiles in different cells and tissues. The same general strategy can be broadened to achieve the proteome-wide, qualitative and quantitative analysis of the state of activity of proteins, by employing ABPs or libraries of ABPs with differing specificity for reaction with proteins. The method and reagents of this invention can be used to identify active proteins of low abundance, active in complex mixtures and can be used to selectively analyze specific groups or classes of proteins, such as membrane or cell surface proteins, or proteins contained with organelles, sub-cellular fractions, or biochemical fractions such as immunoprecipitates. Further, these methods can be applied to analyze differences in expressed proteins in different cell states. For example, the methods and reagents herein can be employed in diagnostic assays for the detection of the presence or the absence of one or more active proteins indicative of a disease state, such as cancer, particularly profiles. The ABPs may be a single ABP that usually binds to at least 5, more usually at least about 10, different target proteins or may be a mixture of ABPs that bind to the same number or fewer proteins and may bind to related or unrelated proteins. Usually the mixture will have from about 2–20, more usually 2–15 different ABPs, where the profile will include a multiplicity of target proteins, encompassing individual or groups of related proteins. Usually, there will be the capability of binding to at least 10 different proteins, more usually at least about 15 different proteins and the number of proteins may be 20 or more, one at least one ABP will be capable of bonding to at least about 5 different target proteins.

The ABPs of the invention may be used to isolate and identify members of a class from the same or different species. With a neutral ABP (does not significantly discriminate between more than half of the members of the class of a single species, where the class has at least about 15 members, more usually at least about 20 members, usually being able to bind to at least 10 members or more), one can determine the available binding activity in a physiological sample of the members that bind, one can isolate new members, and one can inhibit the activity of members of the class, where such inhibition is of interest. In the case of affinity labels, one can determine the available activity in a protein composition of the target proteins, one can differentiate the activity between the target protein and other members of the class on the properties of the protein composition, e.g. cell(s) or lysate, one can obtain a protein activity profile for tissue, cells or lysate in response to various stimuli and one can screen compounds for their binding affinity to the target protein, e.g. drug screening. (It should be understood that enzymes are particularly exemplary of the target proteins and classes of enzymes will be the primary targets. To that extent, enzymes are paradigmatic of the class of target proteins and will be referred to in the future as exemplary and not limiting of the targets).

In this way the probes can be used in research, isolation and identification of proteins of a target class, diagnosis and developing therapies, and with combinatorial libraries designing target compounds having affinity for the target site of the target protein. For enzymes, because of their roles in regulation, cellular activity, response to external stimuli, and the like, there is a particular interest in being able to determine the enzyme activity in a composition, e.g. cell, as distinct from total enzyme, which could include enzyme that is not active, and how the enzyme activity varies in relation to external stimuli and/or changes in the status of the cell. For reacting with the active form of the enzyme or other protein, it is desirable that one employs a functionality that is at least relatively specific for the target enzyme genus. By relatively specific is intended that less than 20%, usually less than 10%, of the proteins other than the target enzymes in the genus will react with the functionality. Equally important is that the functionality optimally does not react, desirably less than 25%, at other than the wild-type active site, particularly with the inactive protein. Methods as those described in this application are employed to distinguish this non-active site labeling from activity-dependent labeling of the active site.

For many of the enzyme genera, functionalities are known that do not significantly react with enzymes of other genera, particularly non-enzymatic proteins and enzymes that have different reactive sites. It is also desirable that the functionality does not react with inactive target enzyme. Examples of inactive states include: 1) proenzymes, e.g. requiring cleavage of the protein; 2) enzymes bound by endogenous inhibitors (either covalent or non-covalent); 3) enzymes in an inactive conformation (e.g. enzymes that require the bindng of another protein, a conformational change, covalent modification by phosphorylation/reduction/oxidation/ methylation/acylation (e.g. formic or acetic acid) for conversion to an active state; 4) denatured enzymes; 5) mutant enzymes; 6) enzymes bound by either reversible or irreversible exogenous inhibitors; and 7) enzymes requiring a cofactor for activity. The enzymes of interest will usually have at least one of serine, threonine, cysteine, histidine, lysine, arginine, aspartate or glutamate as a member of the active site involved in the catalysis of the enzyme reaction. One or more of the functionalities of these amino acids may be the target of the ABP. The manner in which the inactive enzyme is inactivated is chosen to emphasize the differences in bonding of the ABP between the active and inactive state. However, if through the course of implementing the subject methodology, an exogenous inactivator is added to the protein sample and the effects of this treatment on the target protein activity profile of the sample relative to a control (absence of the exogenous inactivator in the sample) are determined, knowledge will be gained as to the form, quantity, and identity of the targeted protein (i.e. inactivated) by this inhibitor.

Enzymes typically fall within six main classes including oxidoreductases, transferases, hydrolases, lyases, isomerases and ligases. In a particular embodiment illustrated herein, an enzyme group of interest includes the class of hydrolases. One genus of the class is serine hydrolases, which includes sub-genera such as proteases, e.g. trypsins, chymotrypsins, esterases, such as acetylcholinesterases, thioesterases, amidases, such as FAAH, and acylpeptide hydrolases, lipases, transacylases, such as lecithin:cholesterol acyltransferase. Another sub-genus is cysteine hydrolases, such as caspases, cathepsins, and palmitoyl acyltransferases. Another sub-genus is metallohydrolases, including matrix metalloproteinases ("MMPs"), e.g. MMP1–13, membrane type metalloproteinases, aminopeptidases, and ADAMalysins. In addition, are phosphatases, such as alkaline phosphatases, acid phosphatases, protein tyrosine phosphatases, and serine/ threonine phosphatases. Further included are the GTPases and ATPases. Besides hydrolases are kinases, which include enzymes such as tyrosine kinases, e.g. src, abl, and lck, serine/threonine kinases, e.g. MAP kinases, MAPK kinases, CAM kinases, protein kinase C, and casein kinases. Also of interest are oxidoreductases, such as cytochrome P450s, amine oxidases, alcohol dehydrogenases, aldehyde dehydrogenases, such as ALDH1, ALDH2, ALDH3, desaturases, etc. Other proteins that are of interest include receptors, such as HLA antigens, hormone receptors, G-proteins coupled receptors, ion channels, transcription factors, protein inhibitors and the like.

The enzymes and/or the sites to which the ABPs bind may be identified in a variety of conventional ways, such as isolating the enzyme, e.g. using an affinity matrix, and characterizing it by mass spectrometry, isolating and sequencing the enzyme or proteolytically fragmenting the enzyme and determining the fractions as a profile for a specific enzyme, electrophoretic separation and Western blotting, or immunoassays employing labeled antibodies specific for the enzyme. The conditions under which the binding is determined will generally be mild conditions, conveniently ambient, using a buffer solution, where the buffer concentration will generally be in the range of about 50–200 mM and the concentration of each active enzyme will generally be about 0.01 pg (picograms)/ml to 0.1 mg (milligrams)/ml. After sufficient time for enzyme binding, non-specifically bound enzyme may be washed away. One may wish to use conditions of increasing stringency, by increasing salt concentration, organic solvent, temperature, etc., to determine levels of binding affinity. By comparison of the sequences at different levels of affinity, one may readily optimize the affinity sequence. In this way one or more libraries of affinity moieties are developed and can be used in conjunction with the other members of the ABP. By having a repertoire of affinity moieties, a specific affinity moiety can be selected that provides the least amount of background in a particular environment. For example, one affinity moiety may be preferred for a target enzyme in a particular background of other enzymes of the same genus.

The conjugates between ABPs and active proteins can be detected and analyzed by a number of different methods. For Western blotting analysis, conventional conditions are employed; quenching can be performed with conventional quenching media, e.g. 2× SDS-PAGE loading buffer (reducing), heated for 5–10 min at 80° C. and then run on an SDS-PAGE gel (8–14% acrylamide). After transferring the protein from the gel to a nitrocellulose paper by electroblotting, the blot is: 1) blocked for 15–60 min with 3% non-fat dry milk in TBS-Tween; 2) incubated with avidin-enzyme conjugate, e.g. horse radish peroxidase (where biotin has been employed as the ligand or other receptor-enzyme conjugate for a different ligand) for sufficient time for complex formation (1–2 hrs); 3) washed with TBS-Tween to remove non-specifically bound receptor-enzyme conjugate; 4) treated with an appropriate enzyme substrate for production of a detectable signal; and 5) detecting the site on the blot of the ABP bound to target. Quantification of differentially expressed enzyme activities among different protein samples is conducted by film densitometry using an AlphaImager 2000 (AlphaInnotech). Alternatively, one may analyze blots using a chemiluminescence detection system, such as the Lumi-Imager (Roche).

Other analytical techniques include binding of the conjugate to a surface by means of the ligand. Conjugated monoclonal antibodies conjugated with a label and specific for one or group of enzymes are added, with the antibodies binding to any target enzyme that is bound to the surface. The presence and amount of the enzyme may then be determined by the label, where the label may be a fluorescent label or an enzyme label, where the enzyme product provides a detectable signal, e.g. fluorescence. Other techniques include releasing the conjugate from the receptor, adding fluorescent receptor and using capillary electrophoresis to quantitate the enzyme.

One may also determine minimal or partial activity. One can do this by comparing the biotin (or other compound binding to a receptor) signals of protein activities found in crude samples to those produced by a fully biotinylated protein standard. For example, take a purified active serine hydrolase and conjugate it to completion with an appropriate ABP, so that there is no further enzyme activity. Then use this conjugated enzyme to generate a standard curve of signals on a gel blot that also contains crude proteomes conjugated with the same ABP. A protein activity in the crude proteome whose signal intensity matches the signal intensity of, for example 10 ng, of the standard enzyme would be considered to represent minimally 10 ng of the active enzyme in the proteome. By performing kinetics and probe concentration dependence assays, one can further determine the average partial activity, where the enzyme is only partially active.

For two samples in which the active proteins of a given family present in these samples are to be quantitatively compared, the following method can be used. A portion of each sample is treated so that the active proteins in the one portion are inactivated. Protein portions of the active and inactive samples are then treated with isotopic variants of the same ABP (e.g., one variant contains 5–10 hydrogens (light probe) and is applied to the inactive portions, the second variant has these 5–10 hydrogens substituted with deuteriums (heavy probe) and is applied to the active portions). After sufficient reaction time, the inactive and active portions of each sample are then separated from their respective ABPs (e.g., by gel filtration chromatography), combined to form a mixed sample, and this mixed sample is digested with a protease (e.g., trypsin) to create a mixture of peptides. These peptides are then treated with an affinity support to selectively isolate peptides covalently tagged with an ABP (e.g., avidin is the affinity support if the probe's tag is biotin). The isolated peptides are then optionally separated by a liquid chromatography step (e.g. HPLC) and characterized by mass spectrometry. ABP-tagged peptides representing active proteins are defined as those found in significantly greater excess (e.g., at least three-fold greater in mass ion abundance) bonded to the heavy probe than to the light probe. The molecular sequence of these peptides can be determined by Tandem Mass Spectrometry to provide the identity of the active proteins from which the ABP-labeled peptides are derived. This first procedure will thereby determine the members of a given protein family that are both present and active in the sample. Two protein portions of the active sample are then treated with the heavy and light probes and processed as described above. The levels of active protein activities will be quantitatively compared across the two samples by ratioing the mass ion abundances corresponding to heavy and light probe-bonded versions of individual peptides. Only those peptides that were determined in the first procedure to represent active proteins will be compared in this manner. To analyze simultaneously more than two samples, the same method may be followed, but an additional, unique isotopic variant of the activity-based probe will be required for each additional sample.

Of particular interest as ABPs are labeled fluorophosphonates, such as biotin-linked fluorophosphonates.

For the most part, the compounds come within the following formula:

wherein:

F, P and O have their normal meaning of fluoro, phospho and oxy;

X is a ligand (including detectable label);

L is a linking group;

R is an aliphatic group of at least 2 carbon atoms, usually at least 4 carbon atoms and not more than about 16 carbon atoms, usually not more than about 12 carbon atoms, usually being straight chain alkylene or alkyleneoxy (wherein the alkylene groups are of from 2–3 carbon atoms), saturated or unsaturated, usually having not more than 2 sites of unsaturation;

m is 0 or 1; and

T is alkyl of from 1 to 6, usually 1 to 3 carbon atoms.

For the most part the ligand will be biotin or derivative thereof, e.g. deiminobiotin or dethiobiotin, and the detectable label may be a fluorescent compound, e.g. fluorescein, rhodamine, Texas red, etc.

Also of interest are compounds come within the following formula:

wherein:

X is a ligand (including detectable label);

L is a linking group;

R is an aryl or heterocyclic group of from 5 to 12 carbon atoms having from 1–2 nitrogen atoms, which may be substituted or unsubstituted, where substituents may be halo, nitro, cyano, oxy, thio, amino, etc. In some instances, alkyl and substituted alkyl of from 1 to 20, usually 1–12 carbon atoms can find use.

Of particular interest are compounds where the linking group includes a dicarboxamido-α,α-alkylene, particularly where biotin (including derivatives thereof) is used which includes a carboxyl group naturally. The alkylene will generally be of about 2–6 carbon atoms, the length will be desirably related to not interfering with the binding of the ligand to its respective receptor and reaction of the sulfonate.

The ligand can be any ligand that does not interfere with the binding of the subject compounds to the serine hydrolases, relatively small, less than about 1 kdal, frequently less than about 500 Dal, has an appropriate receptor and is synthetically accessible. There are a number of popular ligands, such as biotin, dethiobiotin, deiminobiotin, digoxin, 2,4-dinitrophenyl, and derivatives thereof, fluorescein, etc. These ligands have strongly binding natural receptors, such as strept/avidin for biotin and dethio- or deiminobiotin, and antibodies for the remaining listed ligands. In some instances it will be desirable to release the serine hydrolase bonded to the inhibitor of this invention from the receptor. A useful pair is dethiobiotin or deiminobiotin, which can be replaced by biotin.

The subject compounds can be prepared using an α,ω-(halo or pseudohalo)alkene, where the halo or pseudohalo group is displaced with a trialkylphosphite, followed by selective oxidation of the olefin to a carboxy or aldehyde. The activated carboxy, e.g. N-succinimidyl ester or carbodiimide anhydride, may be reacted with the ligand or detectable label bonded to a linking group terminating in an amino group to form an amide. The aldehyde may be bonded to an amine by forming an imine or Schiff's base or by reductive amination, forming an alkylated amine. Other than the ligand, the subject compounds will have fewer than 30 carbon atoms, usually fewer than 25 carbon atoms. There may be and preferably is 1 or more functionalities in the chain joining the ligand or detectable label to the alkylfluorolphosphoric acid group, generally neutral functionalities, such as amido, oxy, thio, urea, thiourea, etc.

When the subject compound is bound to the serine hydroxyl of a serine hydrolase, the resulting inhibited enzyme may have the following formula:

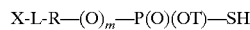

serine hydrolase bonded at the serine group of the active site to the phosphate.

Known serine hydrolases include fatty acid amide hydrolases (FAAH), kallikreins, acylpeptide hydrolases, prostate specific antigen, cholinesterases, trypsins, chymotrypsins, plasmin, thrombin, phospholipases, signal peptidases, amidase signature enzymes, plasminogen activators, prohormone convertases, granzymes, seprase, dipeptidyl and tripeptidyl peptidases, usually being derived from mammalian sources, particularly human, but may come from other sources, both prokaryotic and eukaryotic, including plants, birds, invertebrates, fungi, etc.

The subject inhibitors may be used in a variety of ways. One application is to determine the enzyme, e.g. serine hydrolase, activity of a physiological sample. The sample may be blood, cells, tissue, or other physiological sample of interest. In some situations, samples that are suspected of having one serine hydrolase may be monitored, as in the genetic engineering of serine hydrolase proteins, where the efficiency of synthesis would be of interest. In the case of tissue or cells, the cells may be lysed in accordance with conventional conditions, using a homogenizer, blender, pellets, centrifuge or other convenient device. The resulting lysed cellular composition may be centrifuged and the supernatant adjusted for protein content. Depending on the nature of the ligand, the supernatant fraction may be freed of naturally occurring ligand and/or receptor. The supernatant may be further treated, as appropriate, adding buffer, further dilution, fractionation by chromatography, etc. Where fractionated, individual fractions will be used in the assay.

Candidate compounds to be used as therapeutics associated with indications involving enzyme dysfunction, particularly for inhibiting specific or groups of related enzymes, may be monitored by preparing a reaction mixture with one or more related enzymes and monitoring the effect on the rate of inhibition. One would add one or more subject compounds and a candidate compound and then monitor the rate of inhibition, by isolating aliquots and analyzing the aliquot for enzyme activity or isolating bound enzymes and analyzing the bound serine hydrolases.

The sample will generally be adjusted to have between about 0.1 to 5 μg/ml, more usually 0.5 to 2 μg/ml of protein, larger amounts being unnecessary. The sample may be added in conventional buffers, such as Tris, HEPES, phosphate, etc. Most chemically and biologically inert buffers providing the desired pH may be used. The ABP for serine hydrolase will be a fluorophosphoric acid compound, which can be combined dry or preferably as a water-miscible polar organic solution that is chemically and biologically inert under the conditions of the assay. Ethanol, DMSO, DMF, etc. may be used. Usually, an excess of the ABP will be employed, generally at least about 2 fold excess, usually at least about 5 fold excess, based on actual enzyme concentration, if known, or estimated enzyme, based on total protein, to ensure that substantially all of the available target enzyme has reacted. The mixture will ordinarily be incubated for about 10 min or more, usually not more than about 1 h. The reaction may then be quenched with any convenient quenching agent, particularly elevated temperatures. The resulting denatured composition may then be analyzed, for example, using capillary electrophoresis (microfluidic device), gel electrophoresis, HPLC, mass spectrometry (MALDI), Western blotting, or the like, where the fractions may be observed by virtue of the ligand. Either the ligand provides a detectable signal, usually fluorescence, although electrochemical and chemiluminescence may also be employed, or the ligand may be reacted with a labeled receptor, and detected as the ligand-receptor complex. The receptor may be conjugated with an enzyme that produces a colored or fluorescent product. There are many enzymes known for this purpose. Illustrative enzymes include horse radish peroxidase, $\alpha$-galactosidase, G6PDH, MDH, alkaline phosphatase, lysozyme, etc. In many cases commercially available substrates can be used for detection.

As indicated, the proteins conjugated to the subject compounds may be separated by electrophoresis or other technique, which provides for independent fractions. One can do time courses, to see how the amount of the different fractions changes with time by quantitating the signal. One can also determine the specific member of the group of related enzymes by using antibodies specific for one or more epitopes of each of the enzyme members of interest. After separating the protein into distinct bands, the electrophoretic bands may be reacted with labeled antibodies, where the labels are different from the labels of the subject compounds, so as provide a distinguishable signal, e.g. fluorescence at a different wavelength, electrochemical detection as compared to fluorescence, chemiluminescence, etc.

Of particular interest is to perform kinetics of inhibition by candidate compounds of the rate of reaction of one or more probes with a proteome of target proteins, e.g. a family of proteins. One can select conditions, whereby at a selected time, the amount of conjugate formation is still changing, so that the amount of conjugate varies with the amount of candidate compound present. In this way one can obtain the binding affinity of the candidate compound, where the target proteins can be saturated with the candidate compound. One combines the candidate compound at a predetermined concentration with a fixed amount of the proteome and the probe(s) under conditions whereby the amount of conjugate formation is related to the amount of candidate compound present. The conditions selected may be as close to physiological as the determination may allow or other conditions may be selected, that provide broader differentiation between the reactions of the different target proteins with the conjugate in the presence of the candidate compound. Changes, such as temperature, pH, additives, etc., may be evaluated for their effect on the bioactivity of the candidate compound. One can select conditions that avoid indiscriminate binding of the candidate compound to the proteins present in the protein mixture. Conditions can be chosen where the reactivity of the candidate compound is minimized and then varying the appropriate parameter(s) to enhance activity of the candidate compound. By determining the rates of reaction of the probe at different concentrations of the candidate compound, the $K_1$ of the candidate compound for each of the target proteins can be determined.

One can follow the reaction with time by taking aliquots from the reaction mixture and quenching the aliquots, so that no further reaction occurs. Alternatively, one can select a specific time at which the entire reaction is quenched. Quenching can be by heat, reactive reagent that reacts with the probe, separation of the protein from the reagents, changing another condition that terminates the reaction, or the like. The amount of conjugate for each target protein is then determined. By using probes that provide a detectable signal and isolating the target proteins individually, e.g. using antisera or monoclonal antibodies specific for an individual target protein, one can determine the amount of conjugate for each of the target proteins at at least two different concentrations of the candidate compound. With a plurality of determinations at different concentrations of the candidate compound, one can graph the variation in conjugate formation for each of the target proteins with variation in concentration of the candidate compound. This provides a three dimensional analysis of the variation in inhibitory effect of the candidate compound on a plurality of proteins, particularly related proteins of a protein family. In this way one obtains with a few kinetic determinations a profile of the inhibitory activity of a candidate compound against a plurality of target proteins and conveniently in the presence of a complex proteome, such as a lysate. The analysis not only provides the inhibitory effect of the candidate compound, but the effect of other proteins on the inhibitory effect. In this way, for each concentration of candidate compound, one obtains a result for each of a plurality of target proteins in a complex environment. By having an antibody chip, with each of the antibodies for a target protein at a predetermined region, one contacts the quenched reaction mixture with the chip and can determine the amount of conjugate at each site by means of the detectable ligand.

The information concerning the nature of the protein target, the degree to which the probes bind at a given target and probe concentration under one or more different sets of conditions, the effect of agents on the binding profile and a comparison of the different structures that bind can all be given to a data processor to allow for analysis and comparison of the data. Thus, the subject system in evaluating changes in proteome profile with one or a group of probes or the effect of an agent on probe binding can be analyzed with a data processor and a data bank developed for comparison with known compounds having physiological activity and candidate compounds that have been screened in accordance with the subject methods. The results of the assays can serve as a basis for designing new compounds, modifying existing compounds and predicting the effects of drugs on the proteome profile of cells.

Depending upon the information desired, different data banks will be employed. A data bank concerned with the development of drugs will include the effect of candidate compounds on the ABP profile of the target protein, as well as the other related proteins. In addition, the data bank includes the effect of variation in structure and composition of different compounds on the ABP profile. Also included in the data bank is common cross-reactivity with non-related proteins for compounds that affect the binding to the target protein.

The information that is developed can be used in a variety of ways using data processing. The combinatorial library allows for designing drugs for binding to the active site of a target protein. By determining which variations in structure enhance or reduce the binding affinity of the ABPs, one can employ algorithms that define spatial forms of the active affinity groups and identify modifications that reduce the affinity. Introducing this information into a data processor will provide for the spatial conformation that fits the active site and can also be used to define the charge distribution on the surface. One or more optimized conformations and charge distributions may then be used as the affinity portion of a probe and the affinity determined. The optimized probes can be used individually or in competitive modes to determine their relative affinities for the active site. This information may then be analyzed by a data processor, whereby the desired structure may be further refined. In this way drugs may be rapidly designed for optimum binding affinity.

The information developed with the probes in analyzing proteomes can also be organized in relation to cellular status.

The distribution of active related enzymes is related to particular cellular status, so that one obtains a profile of the amount of each of the active proteins to which the ABPs bind. The information is useful in comparisons between cellular status and the protein profile, where the status is established by other means. A data bank then serves to relate the profile to a basis for treatment of a diseased state. Cancers are exemplary. There is great interest in knowing how aggressive a cancer is, what stage it is in becoming metastatic and how the cancer will respond to different treatments, e.g. hormone treatment, chemotherapy, radiotherapy, etc. Having a correlation between protein profiles and cellular status, even when the proteins have not been shown to be directly involved with the disease pathway permits a rapid determination of the cellular status by obtaining the protein profile. In addition, one may follow the course of the disease by monitoring changes in the protein profile. The information concerning the profile is introduced into a data processor having a data bank of protein profiles, status and outcomes. By comparing the profile with the existing bank of profiles, particularly comparing the changes in profile with time and treatment, the effectiveness of the treatment can be evaluated and a more certain evaluation of the outcome achieved.

In employing the system, the method described above for determining one or more profiles from different related groups of proteins is employed to obtain the initial results or raw data. Based on the conjugation of the ABP to the related group of proteins, one may obtain the amount of each individual target protein and, optionally, the total amount of protein in the related group bound to the target protein providing for relative abundance. If one gets the individual amount and the total amount, one can obtain a relative abundance for each target protein, which will diminish effects that are consistent with the entire group of related proteins and affect the observed value for an individual protein. This information is then processed in a programmed data processor, where the data processor can be programmed with information related to the purpose for the measurement. One employs a program that compares the absolute amount of a target protein and/or the relative abundance to results obtained in other experiments, where standards are devised. The standards may include the effect of known agents on the target protein and/or the relative abundance, the difference between two cell types, e.g. normal or neoplastic, differentiated and non-differentiated, two different differentiated cells, such as T-cells and B-cells, $Th_1$ and $Th_2$, myoblast and fibroblast, genetically modified cell and a wild-type cell, etc. Therefore, the standard may be the results from a single test or plurality of the same test on the same or analogous sample or may be a composite of compiled data related to the purpose of the determination.

Various methods and algorithms have been used for analyzing results and presenting the results in useful form for interpretation. Eisen, et al., Proc. Natl. Acad. Sci. USA (1998) 95, 14863–14868, (specifically incorporated herein by reference) describes using cluster analysis using standard statistical algorithms with graphic display of the results. By employing a dendrogram that assembles all elements into a single tree, where for any set of n genes, an upper diagonal similarity matrix is computed by using the described metric, which contains similarity scores for all pairs of genes. The matrix is scanned to identify the highest value (representing the most similar pair of genes). A node is created joining these two genes, and a gene expression profile is computed for the node by averaging observation for the joined elements (missing values are omitted and the two joined elements are weighted by the number of genes they contain). The similarity matrix is updated with this new node replacing the two joined elements, and the process is repeated n-1 times until only a single element remains. Software implementation of this algorithm can be obtained from the authors on the world wide web at [http://] rana.stanford.edu/clustering.

Ordering was based on weighting genes, such as average expression level, time of maximal induction, or chromosomal position with the element with the lower average weight placed earlier in the final ordering. The display is represented graphically with unchanged genes colored black and increasingly positive log ratios with reds of increasing intensity and increasingly negative log ratios with greens of increasing intensity.

See also, U.S. Pat. Nos. 6,114,114 and 6,132,969, for additional methods of analyzing results and reporting data. These techniques are readily adapted to the present systems in providing for comparisons of the levels of connugation with different ABPs, the variations in profiles of conjugate formation in the presence of candidate drugs or other reagents and the relationship between conjugate profile and disease indications.

The invention will now be described in greater detail by reference to the following non-limiting examples.

EXPERIMENTAL

EXAMPLES

The following examples provide an illustrative synthetic scheme for a fluorophosphonates-based ABP which includes a biotin label or tag. This "FP-biotin" ABP is in no way limiting and is merely illustrative. One of skill in the art can use standard methods to design other ABPs as described herein.

Example 1

Figure 8:
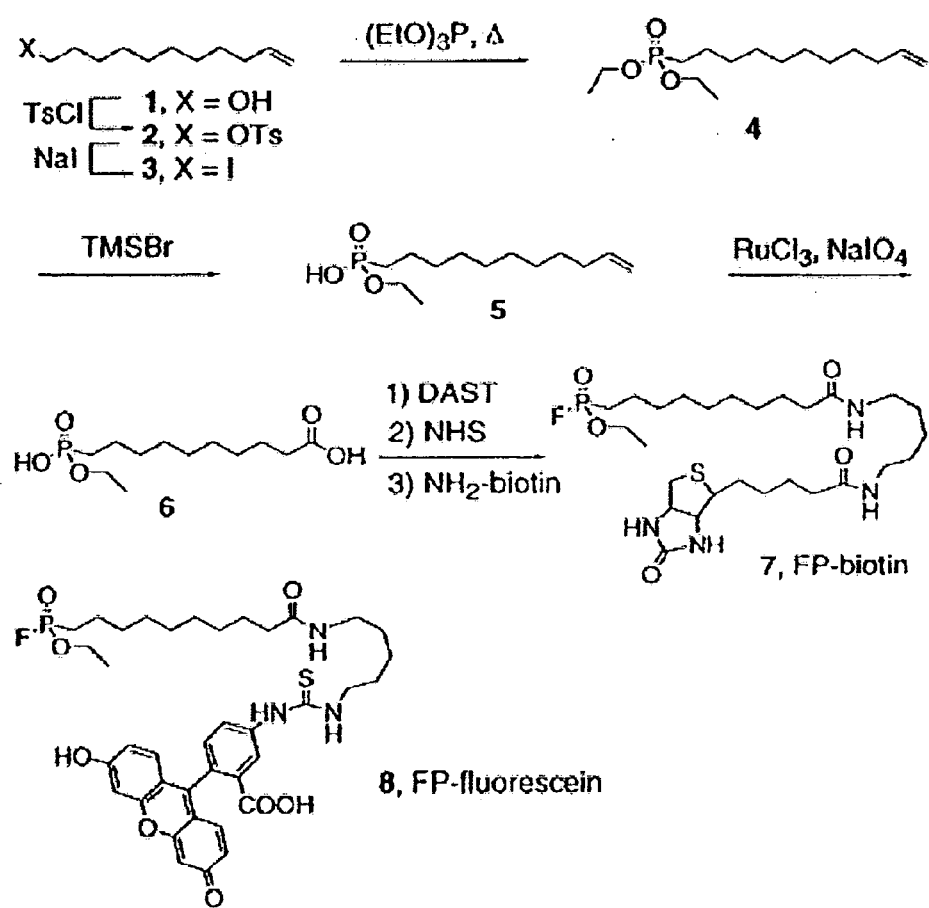
FIG. 8 is a flow diagram of the preparation of an activity-based probe using a polyethylene linker.

Compound 1 is the starting material tetraethyleneoxy (3,6,9-oxa-1,11-diolundecane) as depicted in the flow chart in FIG. 8.

Compound 2. A solution of 1 (3.9 g, 20.0 mmol, 3.0 equiv) in DMF (8.0 mL) was treated with TBDMSCl (1.0 g, 6.64 mmol, 1.0 equiv) and imidazole (0.9 g, 13.3 mmol, 2.0 equiv) and the reaction mixture was stirred for 12 h at room temperature. The reaction mixture was then quenched with saturated aqueous NaHCO3 and partitioned between ethyl acetate (200 mL) and water (200 mL). The organic layer was washed with dried (Na2SO4) and concentrated under reduced pressure. Chromatography (SiO2, 5×15 cm, 50–100% ethyl acetate-hexanes) afforded 2 (1.1 g, 2.0 g theoretical, 55%) as a colorless oil: 1H NMR (CDCl3, 400 MHz) δ 3.8–3.5 (m, 16H, CH2OR), 0.88 (s, 9H, CH3C), 0.0 (s, 6H, CH3Si).

Compound 3. A solution of 2 (0.61 g, 2.0 mmol, 1.0 equiv) in benzene (15 mL, 0.13 M) was treated sequentially with PPh3 (2.6 g, 10.0 mmol, 5 equiv), 12 (2.3 g, 9.0 mmol, 4.5 equiv), and imidazole (0.7 g, 10.3 mmol, 5.2 equiv) and the reaction mixture was stirred at room temperature for 30 min, producing a yellow-orange heterogeneous solution. The soluble portion of the reaction mixture was removed and the insoluble portion washed several times with ethyl acetate. The combined reaction and washes were then partitioned between ethyl acetate (200 mL) and saturated aqueous Na2S2O3 (200 mL). The organic layer was washed sequentially with H2O (100 mL) and saturated aqueous NaCl (100 mL), dried (Na2SO4), and concentrated under reduced pressure. Chromatography (SiO2, 5×15 cm, 5–25% ethyl acetate-hexanes) afforded 3 (0.54 g, 0.82 g theoretical, 66%) as a colorless oil: 1H NMR (CDCl3, 400 MHz) δ 3.85–3.60 (m, 12H, CH2OR), 3.54 (t, J=5.6, 2H, CH2OTBDMS), 3.23 (t, J=7.0 Hz, 2H, CH2I), 0.88 (s, 9H, CH3C), 0.0 (s, 6H, CH3Si).

Compound 4. Triethylphosphite (1.2 mL, 7.0 mmol, 5.4 equiv) was added to 3 (0.53 g, 1.29 mmol, 1.0 equiv) and the mixture was stirred at 150° C. for 1 h. The reaction mixture was cooled to room temperature and directly submitted to flash chromatography (SiO2, 5×15 cm, 100% ethyl acetate) to afford 4 (0.43 g, 0.54 g theoretical, 80%) as a colorless oil: 1H NMR (CDCl3, 400 MHz) δ 4.20–4.05 (m, 4H, CH3CH2OP), 3.80–3.55 (m, 14H, CH2OR), 2.15 (m, 2H, CH2P), 1.31 (t, J=6.0 Hz, 6H, CH3CH2OP), 0.88 (s, 9H, CH3C), 0.0 (s, 6H, CH3Si).

Compound 5. A solution of compound 4 (0.21 g, 0.5 mmol, 1.0 equiv) in CH2Cl2 (2.8 mL, 0.18 M) was treated with HF-pyridine (0.084 mL, ~0.84 mmol, ~1.7 equiv). The reaction was stirred at 25° C. for 30 min and then partitioned between ethyl acetate (100 mL) and water (100 mL). The organic layer was dried (Na2SO4) and concentrated under reduced pressure. Chromatography (SiO2, 2×8 cm, 3–10% CH3OH—CH2Cl2) afforded 5 (0.050 g, 0.28 g theoretical, 32.5%) as a clear oil: 1H NMR (CDCl3, 400 MHz) δ 4.20–4.05 (m, 4H, CH3CH2OP), 3.80–3.55 (m, 14H, CH2OR), 2.15 (m, 2H, CH2P), 1.31 (t, J=6.0 Hz, 6H, CH3CH2OP); MALDI-FTMS m/z 337.1377 (C12H27O7P+Na+ requires 337.1387).

Compound 6. A solution of 5 (0.030 g, 0.096 mmol, 1.0 equiv) in DMF (0.28 mL, 0.34 M) was treated sequentially with N,N-disuccinimidyl carbonate (0.058 g, 0.22 mmol, 2.2 equiv) and triethylamine (0.035 μL, 0.25 mmol., 2.5 equiv). The reaction mixture was stirred at room temperature for 12 h and then partitioned between CH2Cl2 (100 mL) and H2O (100 mL). The organic layer was washed with saturated aqueous NaCl (100 mL), dried (Na2SO4), and concentrated under reduced pressure. Chromatography (SiO2, 2×8 cm, 1–10% CH3OH—CH2Cl2) afforded 50.035 g, 0.043 g theoretical, 81%) as a clear oil: 1H NMR (CDCl3, 400 MHz) δ 4.45 (m, 2H, CH2OC(O)OR), 4.20–4.05 (m, 4H, CH3CH2OP), 3.80–3.55 (m, 12H, CH2OR), 2.84 (s, 4H, CH2C(O)N), 2.15 (m, 2H, CH2P), 1.31 (t, J=6.0 Hz, 6H, CH3CH2OP). MALDI-FTMS m/z 478.1456 (C17H30NO11P+Na+ requires 478.1449).

Compound 7. A solution of 6 (0.020 g, 0.044 mmol, 1.0 equiv) in CH2Cl2 (0.14 mL, 0.40 M) was cooled to 0° C. and treated with oxalyl chloride (0.082 mL, 2M in CH2Cl2, 0.164 mM 3.7 equiv). The reaction mixture was allowed to warm to room temperature and stirred for 18 h. The reaction mixture was then concentrated under a stream of gaseous nitrogen and the remaining residue treated with H2O (0.1 mL) for 5 min. The H2O was evaporated under a stream of gaseous nitrogen and the remaining residue dried by vacuum to provide 7 (0.015 mg, 0.019 mg theoretical, 80%) as a clear oil/film: 1H NMR (CDCl3, 400 MHz) δ 4.45 (m, 2H, CH2OC(O)OR), 4.10 (m, 2H, CH3CH2OP), 3.80–3.55 (m, 12H, CH2OR), 2.84 (s, 4H, CH2C(O)N), 2.15 (m, 2H, CH2P), 1.31 (t, J=6.0 Hz, 3H, CH3CH2OP).

Compound 8. A solution of 7 (0.007 g, 0.016 mmol, 1.0 equiv) in CH2Cl2 (0.22 mL, 0.075 M) at −78° C. was treated with (diethylamino)sulfur trifluoride (DAST, 0.007 mL, 0.048 mmol, 3.0 equiv) and the reaction mixture was stirred for 10 min. The reaction mixture was then partitioned between ethyl acetate (100 mL) and H2O (100 mL) and the organic layer was washed with saturated aqueous NaCl (100 mL), dried (Na2SO4), and concentrated under reduced pressure. Chromatography (SiO2, Pasteur pipette, 100% ethyl acetate) afforded 8 (0.003 g, 0.007 g theoretical, 42%) as a clear oil: 1H NMR (CDCl3, 400 MHz)δ 4.45 (m, 2H, CH2OC(O)OR), 4.27 (m, 2H, CH3CH2OP), 3.80–3.55 (m, 12H, CH2OR), 2.84 (s, 4H, CH2C(O)N), 2.32–2.26 (m, 2H, CH2P), 1.31 (t, J=6.0 Hz, 3H, CH3CH2OP). FP-peg-biotin (9). A solution of 8 (0.003 g, 0.007 mmol, 1.0 equiv) in DMF (0.1 mL, 0.07 M) was added to 5-(biotinamido)-pentylamine (Pierce, 0.0035 g, 0.011 mmol, 1.5 equiv) and the reaction mixture was stirred for 4 h. The solvent was evaporated under a stream of gaseous nitrogen and the remaining residue was washed sequentially with diethyl ether and ethyl acetate, solubilized in a minimal volume of chloroform, transferred to a clean glass vial, and the solvent evaporated. This process was repeated twice more to rid the desired biotinylated product of excess reagents and byproducts, affording 9 as a white film (0.0017 g, 0.0045 g theoretical, 38%): 1H NMR (CDCl3, 400 MHz) δ 6.04 (b s, 1H, NH), 5.77 (b s, 1H, NH), 5.24 (b s, 1H, NH), 5.09 (b s, 1H, NH), 4.51 (m, 1H), 4.40–4.21 (m, 5H, including, CH2OC(O)NR and CH3CH2OP), 3.90–3.55 (m, 12H, CH2OR), 3.30–3.11 (m, 5H, including CH2NHC(O)), 2.92 (dd, J=4.9 and 12.9 Hz, 1H), 2.74 (d, J=12.9 Hz, 1H), 2.35–2.18 (m, 4H, CH2CONHR and CH2P), 1.85–1.40 (m, 12H); 1.31 (t, J=6.0 Hz, 3H, CH3CH2OP); MALDI-FTMS m/z 665.2742 (C26FH48N4O9PS+Na+ requires 665.2756). 1-[(p-Toluenesulfonyl)oxy]-10-undecene (2). A solution of 1 (2.0 g, 11.8 mmol, 1.0 equiv) in pyridine (14.0 mL, 177 mmol, 15 equiv) was cooled to 0° C. and treated with pTsCl (4.5 g, 23.6 mmol, 2.0 equiv). The reaction mixture was kept at 0° C. for 10 h and then partitioned between ethyl acetate (200 mL) and water (200 mL). The organic layer was washed with 10% aqueous HCl (2×200 mL), saturated aqueous NaCl (200 mL), dried (Na2SO4), and concentrated under reduced pressure. Chromatography (SiO2, 5×15 cm, 2% ethyl acetate-hexanes) afforded 2 (3.6 g, 3.8 g theoretical, 94%) as a colorless oil: 1H NMR (CDCl3, 250 MHz) δ 7.76 (d, J=6.5 Hz, 2H, ArH), 7.32 (d, J=7.3 Hz, 2H, ArH), 5.95–5.75 (m, 1H, RCH=CH2), 5.03–4.90 (m, 2H, RCH=CH2), 3.98 (t, J=6.5 Hz, 2H, CH2OTs), 2.42 (s, 3H, ArCH3), 2.02 (m, 2H, CH2CH=CH2), 1.65 (p, J=6.9 Hz, 2H, CH2CH2OTs), 1.50–1.20 (m, 12H); MALDI-FTMS (DHB) m/z 347.1657 (C18H28O3S+Na+ requires 347.1658).

Example 2

Preparation of FP-biotin

FP-Biotin was prepared as described by Liu et al. (Proc. Natl. Acad. Sci. 96(26):14694, 1999) and in U.S. Ser. Nos. 60/195,954 and 60/212,891, herein incorporated by reference in their entirety. 1-Iodo-10-undecene (3). A solution of 2 (3.4 g, 10.5 mmol, 1.0 equiv) in acetone (21 mL, 0.5 M) was treated with NaI (3.2 g, 21 mmol, 2.0 equiv) and the reaction mixture was stirred at reflux for 2 h, producing a yellow-orange solution. The reaction mixture was then partitioned between ethyl acetate (200 mL) and water (200 mL). The organic layer was washed sequentially with saturated aqueous Na2S2O3 (100 mL) and saturated aqueous NaCl (100 mL), dried (Na2SO4), and concentrated under reduced pressure. Chromatography (SiO2, 5×15 cm, 1–2% ethyl acetate-hexanes) afforded 3 (2.3 g, 2.9 g theoretical, 78%) as a colorless oil: 1H NMR (CDCl3, 250 MHz) δ 5.95–5.75 (m, 1H, RCH=CH2), 5.03–4.90 (m, 2H, RCH=CH2), 3.16 (t, J=7.0 Hz, 2H, CH2I), 2.02 (m, 2H, CH2CH=CH2), 1.80 (p, J=6.9 Hz, 2H, CH2CH2I), 1.50–1.20 (m, 12H).

1-[Bis(ethoxy)phosphinyl]-10-undecene (4). Triethylphosphite (12.2 mL, 71 mmol, 10 equiv) was added to 3

(2.0 g, 7.1 mmol, 1.0 equiv) and the mixture was stirred at reflux for 15 h. The excess triethylphosphite was removed by distillation and the remaining residue submitted to flash chromatography (SiO2, 5×15 cm, 25–50% ethyl acetate-hexanes gradient elution) to afford 4 (1.30 g, 2.1 g theoretical, 62%) as a colorless oil: 1H NMR (CDCl3, 250 MHz) δ 5.95–5.75 (m, 1H, RCH═CH2), 5.03–4.90 (m, 2H, RCH═CH2), 4.05 (m, 4H, CH3CH2OP), 2.02 (m, 2H, CH2CH═CH2), 1.80–1.20 (m, 20H); MALDI-FTMS (DHB) m/z 291.2088 (C15H31O3P+H+ requires 291.2089).

1-(Ethoxyhydroxyphosphinyl)-10-undecene (5). A solution of compound 4 (0.31 g, 1.07 mmol, 1.0 equiv) in CH2Cl2 (4.0 mL, 0.3 M) was treated dropwise with trimethylsilyl bromide (TMSBr, 0.17 mL, 1.28 mmol, 1.2 equiv). The reaction was stirred at 25° C. for 1 h, quenched with 5 mL of 5% [w/v] KHSO4, and stirred vigorously for 5 minutes. The reaction mixture was then partitioned between ethyl acetate (100 mL) and water (100 mL), and the organic layer was washed with saturated aqueous NaCl (200 mL), dried (Na2SO4), and concentrated under reduced pressure. Chromatography (SiO2, 2×8 cm, 12–20% CH3OH—CHCl3 with 1% aqueous NH4OH) afforded 5 (0.10 g, 0.28 g theoretical, 36.2.%; most of the remaining mass was recovered as starting material) as a clear oil: 1H NMR (CDCl3, 250 MHz) δ 5.95–5.75 (m, 1H, RCH═CH2), 5.03–4.90 (m, 2H, RCH═CH2), 4.05 (m, 2H, CH3CH2OP), 2.02 (m, 2H, CH2CH═CH2), 1.80–1.20 (m, 20H). MALDI-FTMS (DHB) m/z 285.1589 (C13H27O3P+Na+ requires 285.1596).

10-(Ethoxyhydroxyphosphinyl)-decanoic acid (6). Compound 5 (0.10 g, 0.38 mmol, 1.0 equiv) in a biphasic solution composed of CCl4-CH3CN-H2O (1.0 mL-1.0 mL-1.5 mL; total volume of 3.5 mL, 0.11 M) was treated sequentially with sodium periodate (0.31 g, 1.56 mmol, 4.1 equiv) and ruthenium trichloride hydrate (0.002 g, 0.009 mmol, 0.022 equiv). The reaction mixture was stirred at 25° C. for 2 h and then partitioned between CH2Cl2 (50 mL) and 1 N aqueous HCl (50 mL). The organic layer was washed with saturated aqueous NaCl (25 mL), dried (Na2SO4), and concentrated under reduced pressure. The resulting residue was resuspended in 40 mL of diethyl ether, filtered through a Celite pad, and concentrated under reduced pressure to afford 6 (0.09 g, 0.11 g theoretical, 83%) as a colorless semisolid: 1H NMR (CDCl3, 250 MHz) δ 4.05 (m, 2H, CH3CH2OP), 2.32 (t, J=7.5 Hz, 2H, CH2COOH), 1.80–1.20 (m, 16H); FAB-HRMS (NBA-NaI) m/z 303.1340 (C12H25O5P+Na+ requires 303.1337).

FP-biotin, or 10-(fluoroethoxyphosphinyl)-N-(biotinamidopentyl)-decanamide (7). A solution of 6 (0.007 g, 0.025 mmol, 4.0 equiv) in CH2Cl2 (0.4 mL, 0.06 M) at −78° C. was treated dropwise with (diethylamino)sulfur trifluoride (DAST, 0.021 mL, 0.10 mmol, 4.0 equiv), brought to 25° C., and stirred for 5 min. The reaction mixture was then treated with one-half reaction volume of dimethyl formamide containing N-hydroxysuccinimide (0.05 g, 0.25 mmol, 10 equiv) and stirred for an additional 10 min at 25° C. The reaction mixture was then partitioned between ethyl acetate (50 mL) and water (50 mL), and the organic layer was washed with saturated aqueous NaCl (200 mL), dried (Na2SO4), and concentrated under reduced pressure to afford 10-(fluoroethoxyphosphinyl)-N-(hydroxysuccinyl)-decanamide (as judged by crude 1H NMR;). Without further purification, this compound was treated with 5-(biotinamido)-pentylamine (Pierce, 0.0021 g, 0.062 mmol, 1.0 equiv) in MeOH (0.02 mL) and stirred for 10 min. The solvent was evaporated under a stream of gaseous nitrogen and the remaining residue was washed sequentially with diethyl ether and ethyl acetate, solubilized in a minimal volume of chloroform, transferred to a clean glass vial, and the solvent evaporated. This process was repeated once more to rid the desired biotinylated product of excess reagents and byproducts, affording 7 (0.0011 g, 0.0038 g theoretical, 29%): 1H NMR (CDCl3, 400 MHz) δ 5.98 (b s, 1H, NH), 5.83 (b s, 1H, NH), 5.60 (b s, 1H, NH), 4.90 (b s, 1H, NH), 4.51 (m, 1H), 4.32 (m, 1H), 4.27 (m, 2H, CH3CH2OP), 3.22 (m, 4H, CH2NHCOR), 3.15 (m, 1H), 2.92 (dd, J=4.9 and 12.9 Hz, 1H), 2.72 (d, J=12.9 Hz, 1H), 2.20 (m, 4H, CH2CONHR), 1.85–1.24 (m, 31H); FAB-HRMS (NBA-NaI) m/z 593.3319 (C27FH5ON4O5PS+H+ requires 593.3302).

Preparation of Tissue Samples for Reaction with FP-Biotin. Rat tissues were Dounce-homogenized in Tris buffer (50 mM Tris-HCl buffer, pH 8.0, with 0.32 M sucrose). Tissue extracts were centrifuged sequentially at 1,100×g (5 min), 22,000×g (30 min), and 105,000×g (60 min). The final supernatant (cytosolic fraction) was adjusted to 1 mg protein/mL and then incubated for 30 min at 4° C. with one-tenth volume of avidin-agarose (Sigma) to deplete endogenous avidin-binding proteins. The resulting supernatant after a brief spin to pellet the avidin-beads (2 min at 10,000×g) was removed and treated with FP-biotin as describe below.

Reaction of Protein Samples with FP-Biotin. Unless otherwise indicated, reactions between protein samples and FP-biotin were conducted as follows: FP-biotin (0.4 nmol) in CHCl3 was added to a glass vial and the solvent evaporated under a stream of gaseous nitrogen. Ethanol (7.5 μL) was added to the vial, followed immediately by 192.5 μL of a 1 μg/μL protein stock in Tris buffer, and the reaction mixture was incubated at 25° C. for 30 min (final concentration of FP-biotin was 2 μM). The reaction mixture was quenched by adding one volume equivalent of standard 2× SDS-PAGE loading buffer (reducing) and heating the sample at 80° C. for 5 min. Reactions conducted for longer times (1 hr) or with higher concentrations of FP-biotin (20 μM) did not produce significant increases in the labeling intensity of most proteins, indicating that the majority of proteins had reacted to completion under the reported conditions. However, reactions with higher concentrations of FP-biotin did begin to show significant levels of nonspecific labeling (defined as the appearance of new protein bands that reacted with FP-biotin in both preheated and unheated samples).

Detection of FP-Biotin Reactive Proteins by SDS-PAGE-Western Blotting. Quenched FP-biotin reactions were run on SDS-PAGE (10 μg protein/gel lane) and transferred by electroblotting onto nitrocellulose membranes, which were blocked in TBS with 1% Tween (TBS-Tween) and 3% (w/v) nonfat dry milk for either 1 h at 25° C. or overnight at 4° C. Blots were then treated with an avidin-horseradish peroxidase (HRP) conjugate (BioRad, 1:2000 dilution) in TBS-Tween with 1% nonfat dry milk for 30 min at 25° C. The blot was washed with TBS-Tween three times (10 minutes/wash), treated with SuperSignal chemiluminescence reagents (Bio-Rad), and exposed to film for 0.1 to 8 minutes prior to development. For the comparison of STI-reated versus untreated Charotein samples, the relative amounts of FP-biotin labeling were estimated by film densitometry using an AlphaImager 2000 (AlphaInnotech).

Identification of target proteins by avidin affinity purification. After incubation of protein sample (0.5–2.5 mL, 0.5–1.0 mg/mL) with the ABPs, the sample is diluted to 2.5 mL in Tris or phosphate buffer and passed over a PD-10 size exclusion column to remove excess unreacted ABP. The protein is collected from the column in 3.5 mL of buffer, treated with SDS (final concentration of 0.5%), and heated for 10 min at 80° C. The sample is then diluted 2.5× and incubated with 100 microliters of avidin agarose beads (Sigma) for 1–4 hours at room temp. The beads are then washed with several volumes of buffer to remove unbound protein and the ABP-labeled proteins are eluted with 100 microliters of standard SDS-PAGE loading buffer by heating at 90° C. for 5 minutes. The eluted proteins are run on an SDS-PAGE gel and ABP-labeled proteins identified by staining and/or avidin blotting, excised from the gel, digested with trypsin, and the resulting peptide mixture characterized by MALDI and/or electrospray mass spectrometry. The mass spec information is used in database searches to identify the ABP-labeled proteins.

Example 3

Molecular Characterization of FP-biotin Reactive Proteins

Figure 5:
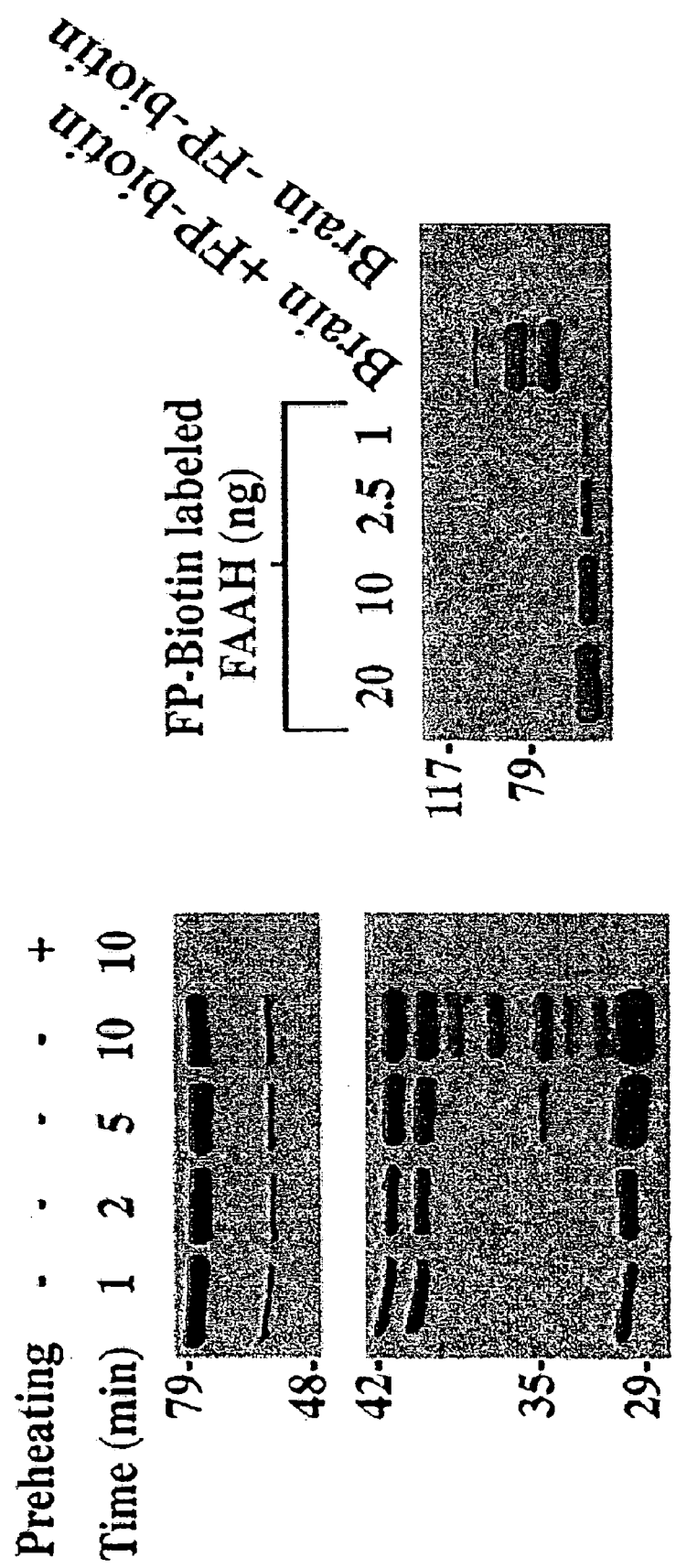
FIG. 5 shows identification of FP-biotin reactive proteins from rat brain. Intensity of labeling of FP-biotin as ABP was compared with that of serial dilution of a FAAH sample reacted to completion with the inhibitor.

Brain soluble extracts were run over a Q sepharose column using an ÄKTA FPLC (Amersham Pharmacia Biotech) and eluted with a linear gradient of 0–500 mM NaCl. Samples of the elution fractions (10×2.5 mL fractions) were labeled with FP-biotin as described above, and those fractions containing the 75 kDa and 85 kDa labeled proteins were pooled and passed over a Mono-Q sepharose column. Proteins were eluted from the Mono-Q column with a linear gradient of 200–500 mM NaCl and those elution fractions enriched in the two labeled proteins were then run on SDS-PAGE and transferred to polyvinylidine difluoride (PVDF) membranes by electroblotting. Regions of the PVDF membranes containing the 75 and 85 kDa FP-biotin reactive proteins were excised, digested with trypsin, and the resulting peptides analyzed by matrix-assisted laser desorption ionization (MALDI) and MALDI-post-source decay time-of-flight mass spectrometry (Chaurand, et al. (1999) J. Am. Soc. Mass. Spectrom. 10, 91–103) on a Kratos Kompact Seq Instrument equipped with a curved field reflectron. The MALDI peptide data were used in MS-Fit and MS-Tag searches of the ProteinProspector databases (found on the world wide web at [http://]falcon.ludwig.ucl.ac.uk/mshome3.2.htm), which identified the 75 kDa protein as the rat orthologue of a human protein sequence KIAA0436 and the 85 kDa protein as acylpeptide hydrolase (APH). (see FIG. 5).

Expression of Serine Hydrolases in HEK-293 Cells. The rat APH cDNA was cloned as follows. Primers were designed based on the enzyme's cDNA sequence (Kobayashi, et al. (1989) J. Biol. Chem. 264, 8892–8899) and used in polymerase chain reaction experiments to amplify a 1.4 kb partial cDNA clone from a rat liver 5' Stretch Plus cDNA library (Clontech). This amplified cDNA was used as a probe to isolate a full length APH cDNA from a liver library. The APH cDNA was subcloned into the eukaryotic expression vector, pcDNA3, and transiently transfected into HEK-293 cells as described previously. Transfected cells were harvested by trypsinization, washed with Hepes buffer (125 mM Hepes, pH 8.0, 100 mM NaCl) and Dounce-homogenized in Hepes buffer. Cytosolic and membrane fractions were isolated as described previously (Giang and Cravatt (1997) Proc. Natl. Acad. Sci. USA 94, 2238–2242) and labeled with FP-biotin as detailed above.

Design and Synthesis of a Biotinylated Fluorophosphonate, FP-Biotin. For the generation of a tagged, activity-based probe for the serine hydrolase family of enzymes, we considered several possible reactive groups and labeling strategies. Previous work by Glynn and colleagues had demonstrated that a saligenin phosphoramidate was a potent inhibitor of neuropathy target esterase (NTE) and could be synthesized with a biotin tag to identify this protein in tissue extracts (Glynn, et al. (1994) 301, 551–556). However, this inhibitor displayed remarkable specificity for NTE in these experiments, and thus appeared too selective to be useful as a general probe for serine hydrolases. Powers and colleagues had generated isocoumarin inhibitors coupled to biotin as serine hydrolase inhibitors (Kam, et al. (1993) Bioconjugate Chem. 4, 560–567; Winkler, et al. (1996) Mol. Immunol. 33, 516–623). While these isocoumarins reacted with a greater range of serine hydrolases than the aforementioned salgenin phosphoramidate, the requirement that these compounds alkylate a second functional group in the enzyme active site to achieve stable irreversible inhibition suggested that a significant number of serine hydrolases might remain insensitive to such reagents. In contrast, FP inhibitors seemed to satisfy the dual requirement of displaying 1) reactivity against the majority of serine hydrolases, and 2) selectivity for this enzyme family among the various classes of hydrolytic enzymes. While radiolabeled FPs were available commercially and through our own synthetic efforts (Patricelli, et al. (1999) Biochemistry 38, 9804–9812), the detection of such agents by fluorography requires several days to weeks (Patricelli, et al., supra; Keshavarz-Shokri, et al. (1999) Anal. Biochem. 267, 406–411), greatly limiting their general utility as rapid and high-sensitivity probes for profiling serine hydrolase expression and function.

10-undecen-1-ol (1)(numbering from Scheme 1) was converted to iodinated compound 3 through a tosylate intermediate (2). Reaction of 3 with excess triethylphosphite under reflux conditions afforded the diethoxy phosphonate 4, which was converted to the ethoxyhydroxy phosphonate 5 by treatment with trimethylsilylbromide (TMSBr). The double bond of 6 was oxidatively cleaved with ruthenium trichloride and sodium periodate (Carlsen, et al. (1981) J. Org. Chem. 46, 3k936–3938) to yield the terminal carboxylic acid product 6. Treatment of 6 with excess diethylaminosulfur trifluoride (DAST) and N-hydoxysuccinimide (NHS) afforded an N-succinyl fluorophosphonate intermediate which was reacted with 5-(biotinamido) pentylamine (NH2-biotin) to generate FP-biotin (7). This synthetic route also allowed for the facile coupling of 6 to other reporter groups, including fluorescein cadaverine, which generated a fluorescent fluorophosphonate, FP-fluorescein [8; MALDI-FTMS (DHB) m/z 778.2671 (C38H47FN3O8PS+Na+ requires 778.2703)].

Figure 4A:
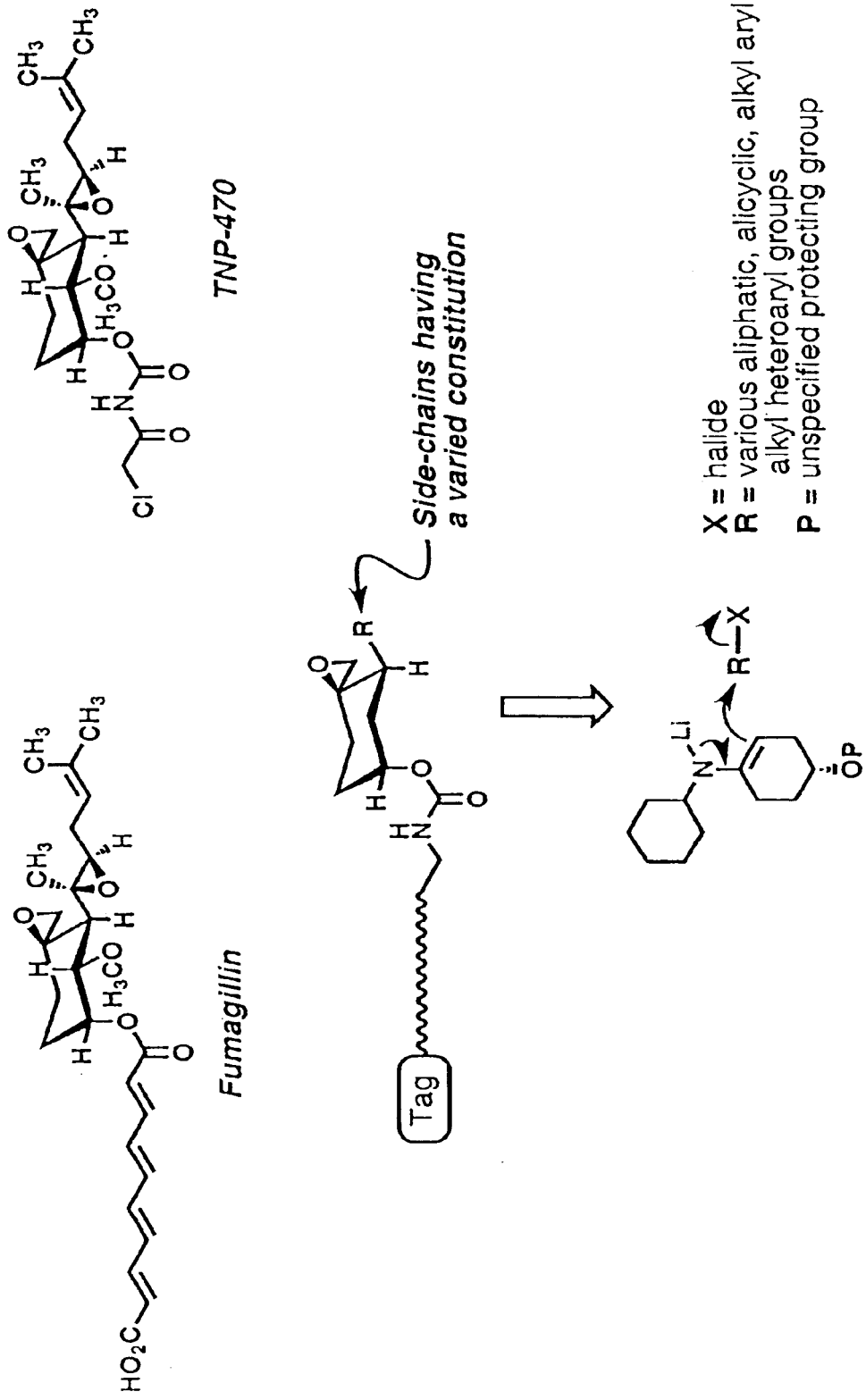
FIG. 4 shows an illustration of a strategy for synthesis of biotinylated sulfonate esters for use as ABPs and a strategy for stereocontrolled synthesis of conformationally well-defined spiroepoxides of type VI (see also, Sornensen, et al., Angew. Chem. Int. Ed., 1999, 38:971–974, herein incorporated by reference in its entirety).
Figure 4B:
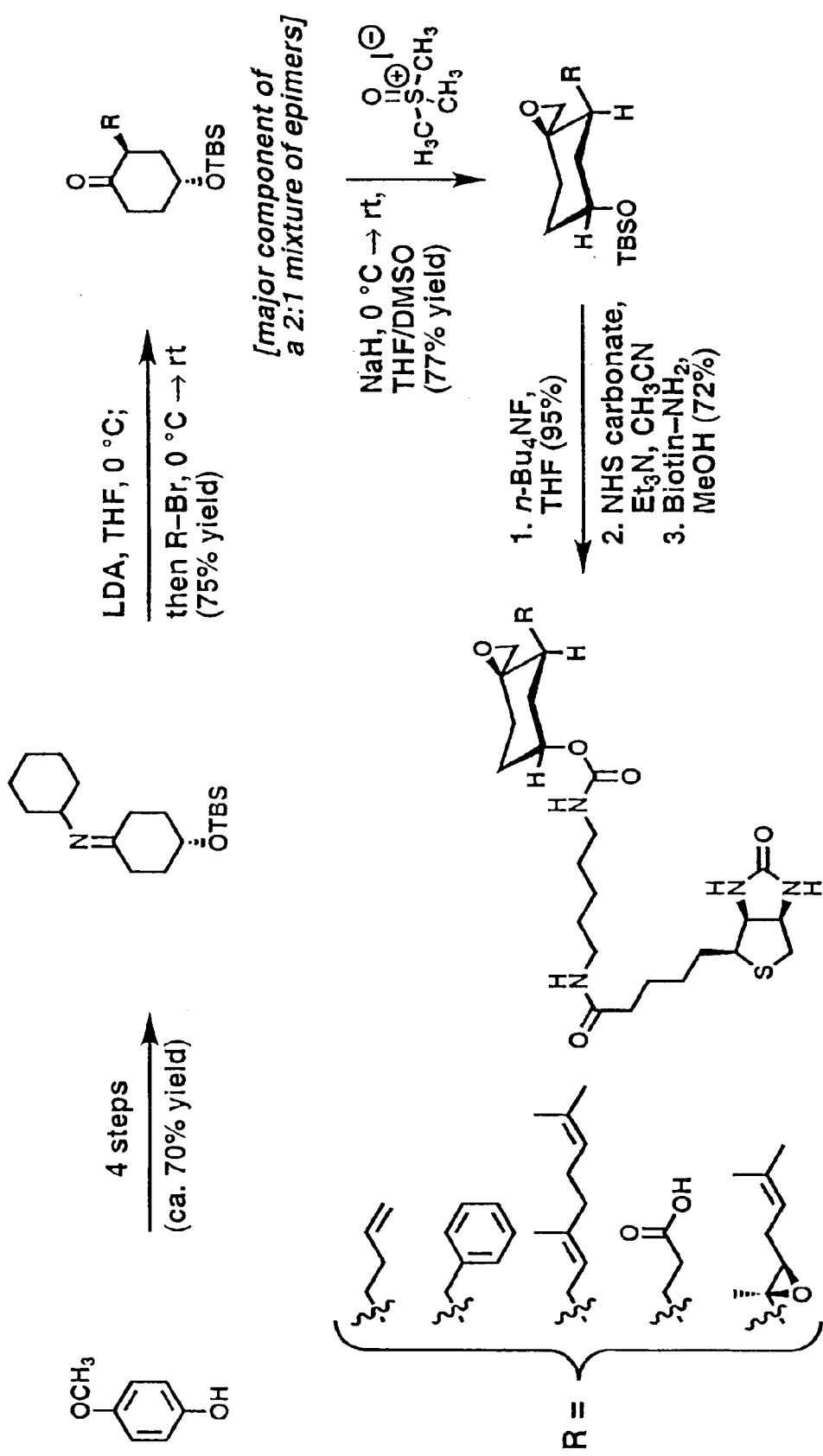

A similar scheme was utilized to synthesize biotinylated sulfonate esters for use as ABPs as shown in FIG. 4. Similarly, FIG. 4 shows a strategy for stereocontrolled synthesis of conformationally well-defined spiroepoxides of type VI (see also, Sornensen, et al., Angew. Chem. Int. Ed., 1999, 38:971–974, herein incorporated by reference in its entirety). Compounds of type VI are analogs of the metalloprotease (MetAp-2) inhibitor fumagillin and are used as ABPs herein.

Example 4

FP-biotin is an Activity-based Probe for Serine Hydrolases

To initially test FP-biotin's utility as an activity-based probe for serine hydrolases, we reacted this agent with the mammalian serine amidase, fatty acid amide hydrolase (FAAH) (Cravatt, et al., (1996) Nature (London) 384k, 83–87). FP-biotin behaved as a potent irreversible inhibitor of FAAH (data not shown), displaying properties similar to those of other FP inhibitors of the enzyme (Patricelli, et al., supra; Deutsch, et al. (1997) Biochem. Pharmacol. 53, 255–260). We have shown that serine residue 241 serves as FAAH's catalytic nucleophile and mutation of this residue to alanine (S241A) generates an inactive enzyme (Patricelli, et al., supra). Therefore, FP-biotin (2 µM) was reacted with both FAAH and the S241A mutant (80 nM) for 10 minutes, after which the proteins were subjected to standard SDS-PAGE-Western blotting procedures using either anti-FAAH antibodies or avidin as detection reagents (FIG. 1A). While anti-FAAH antibodies identified both FAAH and the S241A mutant, avidin detected only FAAH in the FP-biotin reactions, demonstrating that this inhibitor exclusively reacted with the active form of the enzyme.

To further explore FP-biotin's reactivity with serine hydrolases, we incubated soluble fractions of rat testis with this inhibitor. Consistent with the abundance of proteases found in this tissue (Monsees, et al. ((1997) Adv. Exp. Med. Biol. 424, 111–123), FP-biotin labeled more than ten testicular proteins. Phosphonylated proteins of a variety of molecular masses were observed, ranging from 20–100 kDa, with a high concentration of labeled proteins found between 25–40 kDa, possibly representing members of the kallikrein clan of serine proteases (MacDonald, et al. (1996) J. Biol. Chem. 271, 13864–13690). Importantly, boiling the protein sample prior to treatment with FP-biotin blocked nearly all protein labeling, further supporting that this tagged inhibitor reacts with serine hydrolases in an activity-dependent manner. Kinetic analyses revealed that the identified serine hydrolases displayed remarkably different rates of FP-biotin reactivity, with two of the larger proteins labeling to apparent completion within one minute and most of the smaller proteins reacting more slowly over the course of several minutes.

Considering that many serine proteases exist in vivo as inactive complexes with endogenous inhibitory proteins (Kato (1999) Hum Mutat. 13, 87–98; Declerck, et al. (1997) Adv. Exp. Med. Biol. 425, 89–97; Monsees, et al., supra), we compared the ability of FP-biotin to react with both free and inhibitor-bound proteases. While FP-biotin reacted strongly with free trypsin, the tagged inhibitor did not label a trypsin sample that was preincubated with the Kunitz-type serine protease inhibitor, soybean trypsin inhibitor (STI), despite the presence in the latter reaction of significantly greater amounts of trypsin. Soluble fractions of rat testis were also exposed to STI and then treated with FP-biotin. Consistent with the relatively broad specificity of this protease inhibitor, several, but not all FP-biotin reactive proteins showed significantly lower labeling intensities in the STI-treated sample.

Collectively, these results highlight that FP-biotin can detect differences in the functional state of a serine hydrolase, even in the special cases where enzyme activity varies without correlation to enzyme quantity. Such observations gain particular significance when one considers the complexity and diversity of serine proteases and inhibitors typically present in whole cell and tissue samples (Kato, supra; Declerck, supra; Deutsch, et al., supra). Without an activity-based probe like FP-biotin, standard genomics and/ or proteomics studies would have difficulty distinguishing free (active) from inhibitor-bound (inactive) proteases in these samples. Finally, the ability to monitor rates of FP-biotin labeling can greatly assist in the identification of even quite subtle changes in serine hydrolase activities.

Molecular Characterization of FP-Biotin Reactive Proteins. In order to verify that the proteins labeled by FP-biotin in crude tissue extracts were indeed serine hydrolases, two phosphonylated proteins were isolated from rat brain cytosol. The most strongly labeled brain proteins ranged from 75–85 kDa in size and eluted from a Q sepharose column between 300 and 450 mM NaCl. To estimate the abundance of these proteins in the Q elutions, the intensity of their labeling with FP-biotin was compared to that of a serial dilution of a FAAH sample reacted to completion with the inhibitor. Both the 75 and 85 kDa FP-biotin reactive proteins displayed labeling intensities similar to that of a 20 ng sample of FAAH (0.35 pmoles), setting a lower limit for the quantity of these proteins that was well within the range needed to obtain protein sequence information. The 85 and 75 kDa proteins were identified by standard protein chemistry techniques as acylpeptide hydrolase (APH) (Kobayashi, et al. (1989) J. Biol. Chem. 264, 8892–8899), a serine peptidase that has been shown to react with DIFP (Scaloni, et al. (1992) J. Biol. Chem. 267, 3811–3818), and the rat orthologue of a human protein sequence KIAA0436 (Ishikawa, et al. (1997) DNA Res. 4, 307–313). Interestingly, a homology search revealed that the KIAA0436 protein shares 30% identity with the prokaryotic enzyme Protease II, also an established serine hydrolase that reacts with DIFP (Yoshimoto, et al. (1995) J. Biochem. 117, 654–660). The Ser-His-Asp catalytic triad residues of Protease II were conserved in the KIAA0436 protein, supporting that this mammalian protein is a novel member of the protease II family of serine proteases. Finally, FP-biotin also labeled a 100 kDa brain protein that appeared to be expressed at much lower levels (equivalent to 15 fmoles, or ~1 ng, of FAAH), demonstrating that this tagged inhibitor can readily detect subnanomolar concentrations of serine hydrolases (15 fmol/20 µL per gel lane). (see FIG. 5).

To test whether FP-biotin could record changes in the expression level of serine hydrolases in crude cellular extracts, we transfected cDNAs for both APH and FAAH into HEK-293 cells. Treatment of the cytosolic and membrane fractions of these cells with FP-biotin identified a strongly phosphonylated 85 kDa protein in the APH-transfected cells, but not in control cells transfected with either empty vector or the FAAH cDNA. In contrast to this labeling pattern, an abundant 65 kDa phosphonylated protein was identified exclusively in the membrane fraction of FAAH-transfected cells, consistent with previous characterizations of this serine hydrolase as an integral membrane protein (Giang and Cravatt, supra, Patricelli, et al. (1998) Biochemistry 37, 15177–15187). Longer exposures of the cytosol blot identified in the mock and FAAH-transfected HEK cells a weak 85 kDa signal that may represent endogenous levels of APH in this cell type.

In summary, the data presented demonstrate that FP-biotin can: 1) react with numerous serine hydrolases in crude cell and tissue samples, 2) detect subnanomolar concentrations of serine hydrolases, and 3) record differences in both the functional state and expression level of these enzymes. It is also important to highlight that the identification of FP-biotin labeled proteins using standard avidin-HRP chemiluminescence assays is extremely rapid (requiring exposure times of only seconds to minutes), making this chemical agent particularly well suited for high throughput proteomics investigations. Additionally, the covalent attachment of a biotin molecule to phosphonylated serine hydrolases should assist in the subsequent biochemical characterization of these enzymes. For example, Schriemer and colleagues have recently developed a method that combines immobilized avidin beads with MALDI mass spectrometry to facilitate the chemical analysis of biotinylated proteins and peptides (Schreimer, et al. (1998) Anal. Chem. 70, 1569–1575). If integrated with FP-biotin, this technique allows for the molecular identification of serine hydrolases (as well as their respective catalytic nucleophiles) directly from whole cell and tissue samples.

Example 5

Profiling Serine Hydrolases in Rat Tissues with FP-biotin

To test FP-biotin's ability to resolve complex patterns of serine hydrolase expression, we compared the profiles of phosphonylated proteins from soluble extracts of rat brain, liver, testis, and prostate. In the lower molecular mass range, clear tissue-specific and tissue-restricted FP-biotin reactive proteins were identified. Interestingly, a strongly labeled 33 kDa protein was identified exclusively in prostate (III). While the molecular size of this phosophonylated protein is consistent in mass with human prostate specific antigen (PSA) (Bei, et al. (1995) J. Clin. Lab. Anal. 9, 261–268), a serine protease expressed primarily in this tissue, orthologues of PSA are not thought to exist in rodents based on previous molecular (Southern blots) and cell biological (immunocytochemistry) studies (Karr, et al. (1995) Cancer Res. 55, 2455–2462). The identification of an FP-biotin reactive protein abundantly and selectively expressed in rat prostate suggests that this organism may indeed possess functional (but not necessarily high sequence-related) homologues of human PSA, an observation that merits further investigation considering PSA's status as a principal marker for prostate cancer (Polascik, et al. (1999) J. Urol. 162, 293–306). Several other FP-biotin reactive proteins also displayed tissue-restricted patterns of expression, including a testis-specific 42 kDa protein (I) and two 38 kDa proteins, one of which was found in brain and testis, and the other in brain and liver (II). In the larger molecular mass range, most of the FP-biotin reactive proteins appeared to display broad tissue distributions. However, a labeled 65 kDa protein was found in highest relative abundance in liver, at lower levels in testis and prostate, and was not detected in brain (I). Similarly, a phosphonylated 70 kDa protein was found exclusively in liver (II).

The subject invention provides reagents that can be used for identifying enzyme activity for a class, sub-class or individual members of the class in an enzyme sample. The reagent(s) comprise a functionality reactive with an amino acid at the active site, a linker that, depending on the purpose of the determination, will bind to all or most members of the class, a sub-group of the class or individual members of the class, and a ligand for sequestering the reagent-conjugated-enzyme. In this way tissue or cells can be assayed for enzyme activity of the different groups indicated above, to determine the response to external stimuli, such as drugs, heat, infection, surgical intervention, neoplasia, etc. In addition, changes in the nature of a cell may be determined with aging, transformation, gene therapy, etc. The reagents specific for a member of a class are prepared using combinatorial synthesis of the linker and screening for compounds with high affinity for a specific enzyme. The ligand allows for isolation and identification of the enzyme with which the reagent has reacted, so as to identify the enzyme for which the reagent is specific. Once identified, the linker may be further modified for optimization.

Example 6

Comparison of Serine Hydrolase Profile of FP-biotin and FP-peg-biotin

Results

Synthesis of FP-Peg-Biotin (9). A first generation FP probe, FP-biotin, possessed a linear decamethylene chain connecting its FP reactive group to 5-(biotinamido)-pentylamine through an amide bond (15). A variant of FP-biotin in which the agent's decamethylene chain was replaced by a more hydrophilic tetraethylene glycol linker was synthesized. Briefly, tetraethyleneglycol (1) was monosilyated to provide compound 2, which following conversion to alkyl iodide 3, was reacted with triethylphosphite to give phosphonate 4. Desilyation of 4 with HF-pyridine, followed by treatment with N,N-disuccinimidyl carbonate, provided NHS-carbonate 6. Compound 6 was converted to monoethoxy phosphonate acid 7 by treatment with oxalyl chloride followed by hydrolytic workup. Compound 7 was treated with DAST to give fluorophosphonate 8, which was then coupled to 5-(biotinamido)pentylamine (Pierce) to provide FP-peg-biotin (9).

Figure 16:
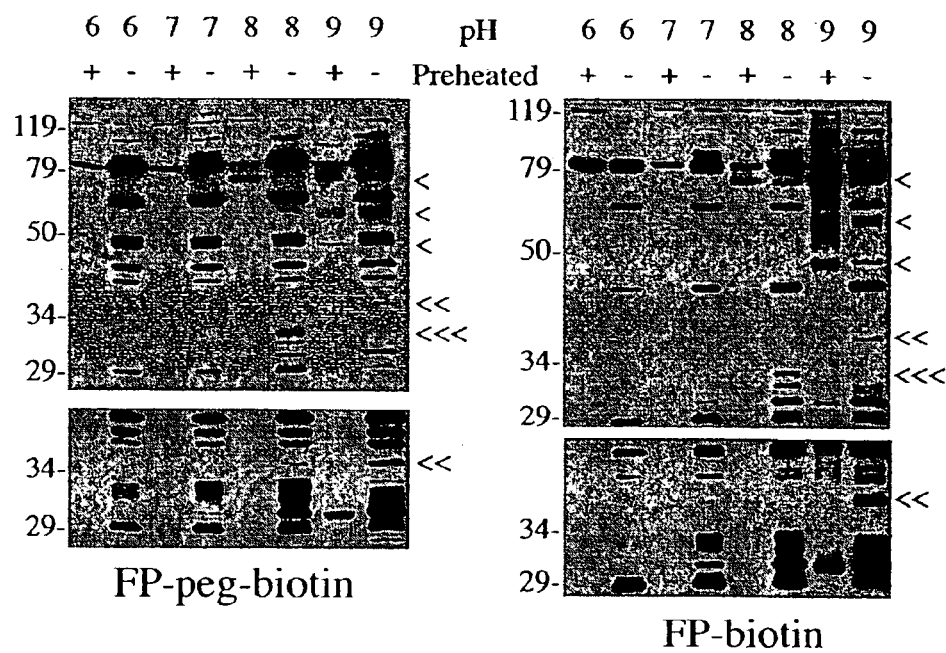
FIG. 16: FP-peg-biotin labels serine proteases but not their respective zymogens. Samples of each protein (100 nM) were treated with FP-peg-biotin (4 $\mu$M) for 1 hour (50 mM Tris, pH 7.2), quenched with 2× SDS-PAGE loading buffer (reducing), and analyzed by SDS-PAGE and blotting with avidin (45 ng protein/lane, bottom two panels). 50× protein stocks were also run on an SDS-PAGE gel and stained with Coomassie blue (2.2 $\mu$g/lane, top panels). Note that the weak avidin signal seen in the chymotrypsinogen sample upon longer exposures may represent FP-peg-biotin reactivity with trace amounts of contaminating chymotrypsin, which is reported to compose up to 2% of the purchased proenzyme.

FP-Peg-Biotin Reacts with Serine Proteases in an Activity-Dependent Manner. To demonstrate that biotinylated FPs could distinguish active proteases from their inactive zymogens, FP-peg-biotin was incubated with equal amounts of trypsin, trypsinogen, chymotrypsin, and chymotrypsinogen. The products of each reaction were then compared by SDS-PAGE and blotting with avidin (FIG. 16). FP-peg-biotin strongly labeled both trypsin and chymotrypsin, but exhibited little or no reactivity with their respective zymogens. Protein staining revealed that a significant fraction of the chymotrypsin sample had been degraded during the course of setting up the reaction. Nonetheless, FP-peg-biotin still showed a much stronger labeling intensity with the chymotrypsin sample than with its chymotrysinogen counterpart, despite the substantially lower quantity of protein present in the former reaction. Indeed, the low level of FP-peg-biotin labeling observed in the chymotrypsinogen sample (seen only in the 5× exposure panel) may have actually represented reactivity with trace amounts of chymotrypsin rather than with the zymogen itself, as the purchased proenzyme is reported to possess up to 2% active protease.

Comparing the Serine Hydrolase Activity Profiles Generated with FP-Biotin and FP-peg-Biotin. Soluble fractions of rat testis (1 $\mu g/\mu L$) were treated with either FP-biotin or FP-peg-biotin (4 $\mu M$) for 1 h at room temperature (50 mM Tris, pH 7.2, 150 mM NaCl) and the labeled serine hydrolase activities detected by SDS-PAGE and blotting with avidin. Control reactions in which the proteome was heat-denatured prior to treatment with biotinylated FPs were also analyzed to distinguish specific (heat-sensitive) from nonspecific (heat-insensitive) protein reactivity. The serine hydrolase activity profiles produced by each biotinylated FP were strikingly similar to one another with a single notable exception (FIG. 17A). A pair of 50 kDa serine hydrolase activities were strongly labeled by FP-peg-biotin, but displayed very low reactivity with FP-biotin (arrowhead). FP-proteome reactions conducted for longer times (2 hours to overnight) increased the labeling intensity of some serine hydrolases, but did not result in the detection of any new heat-sensitive protein reactivities. Therefore, one hour FP-proteome reactions provided profiles that were considered to represent "maximal coverage" of serine hydrolase activities, and unless otherwise noted, subsequently described reactions were conducted for this length of time.

The Probe Concentration Dependence of FP-Proteome Reactions. Samples of the rat testis proteome were treated for one hour with either FP-biotin or FP-peg-biotin over a probe concentration range of 0.5–8.0 μM (FIG. 17B and C). Most FP-biotin-labeled proteins displayed enhanced signal intensities with increasing amounts of probe, indicating that their reactivities were not saturated at low micromolar FP-biotin concentrations. In contrast, several of the FP-peg-biotin-labeled proteins showed no detectable change in their signal intensities with increasing concentrations of probe (FIG. 17C, arrowheads). These enzymes had either reacted to completion, or were saturated in their rates of labeling at all of the FP-peg-biotin concentrations tested. Kinetic experiments supported the former explanation, as clear concentration-dependent labeling for all of these proteins could be observed in reactions conducted for a shorter time (1 min; FIG. 17D, arrowheads).

Notably, in reactions conducted for one hour with concentrations of 4–8 μM FP-peg-biotin, at least 18 distinct serine hydrolase activities could be resolved on a single lane of a one-dimensional SDS-PAGE gel (FIG. 17C). An even higher concentration of FP-peg-biotin (16 μM) produced a qualitatively similar serine hydrolase activity profile to that observed with 4 and 8 μM probe (i.e., no new heat-sensitive protein reactivities were detected at 16 μM), but also generated a high level of nonspecific protein reactivity. Therefore, it was concluded that biotinylated FPs displayed maximum ratios of specific to nonspecific proteome reactivity at concentrations ranging from 4 to 8 μM.

Figure 18:
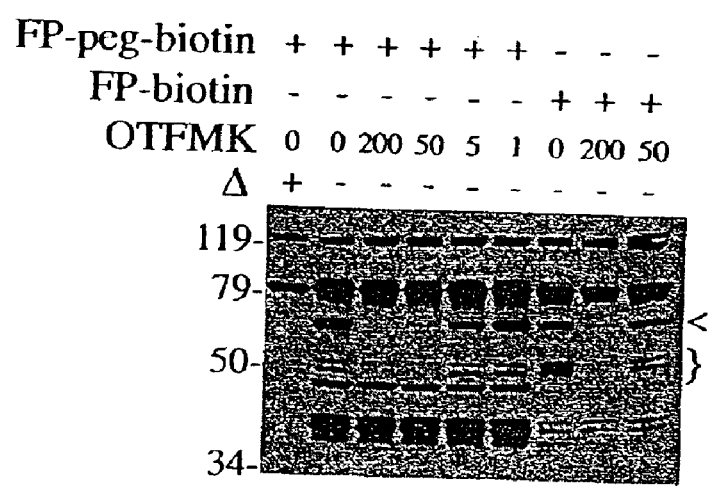
FIG. 18: pH-dependence of FP-proteome reactions. Protein samples were treated with either FP-biotin (left panel) or FP-peg-biotin (right panel) for 1 hour (50 mM Tris o50 mM CAPSo50 mM sodium citrate) at pH 6.0, 7.0, 8.0, or 9.0 and analyzed by SDS-PAGE and blotting with avidin. Serine hydrolases displaying pH optima of 8 and 9 are highlighted by triple and double arrowheads, respectively. Proteins exhibiting heat-insensitive FP-reactivity at pH 9 are highlighted by single arrowheads.

The pH-Dependence of FP-Proteome Reactions. A single mixed buffer assay was used to evaluate the pH-dependence of FP-proteome reactions over a pH range of 6.0–9.0 (conditions: 1 μg/μL soluble testis protein, 4 μM biotinylated FP, 50 mM Bis-Tris Propane, 50 mM CAPS, 50 mM citrate, 150 mM NaCl; one hour reaction). Several types of pH-dependence were observed among the FP-labeled proteins, with some serine hydrolases exhibiting an optimal FP reactivity at pH 8.0 (FIG. 18, triple arrowheads) and others showing an FP reactivity that continued to increase in intensity as the pH was raised to 9.0 (double arrowheads). Although multiple serine hydrolases appeared to show "pH-independent" FP reactivities, kinetic analyses indicated that most of these enzymes had labeled to completion during the time course of the reactions (see above). Thus, these enzymes likely react with FPs in a pH-dependent manner that might be visualized by modifying the parameters of the reaction to slow their rates of labeling (e.g., lowering the probe concentration and/or reducing the incubation time). Finally, background FP reactivity increased significantly at pH 9.0, with several labeled proteins appearing in the preheated control lane (single arrowheads). Coomassie blue staining revealed that these labeled proteins were all high abundance constituents of the testis proteome, indicating that heat-insensitive labeling represents a nonspecific form of FP reactivity. Considering further that the majority of serine hydrolases displayed similar (or greater) FP reactivities at pH 8.0 relative to pH 9.0, the former pH appears better suited for the functional analysis of this enzyme family in complex proteomes.

Kinetic Analysis of FP-Proteome Reactions. Although single time point measurements offer a simple and rapid means to obtain a general profile of the active serine hydrolases present in complex proteomes, kinetic analyses are required to decipher more intricate changes in enzyme activity. For example, alterations in serine hydrolase activity that take place in the absence of changes in enzyme abundance may remain undetected with biotinylated FPs unless rates of reactivity are measured. To explore the kinetics of FP-proteome reactions, rat brain membrane fractions were treated with biotinylated FPs and the time course of protein labeling followed by SDS-PAGE and blotting with avidin The goal of these studies was two-fold: 1) to confirm that membrane-associated serine hydrolases could be profiled with biotinylated FPs, and 2) to test whether individual serine hydrolases showed significant differences in their respective rates of reactivity with FP-biotin and FP-peg-biotin.

Figure 19:
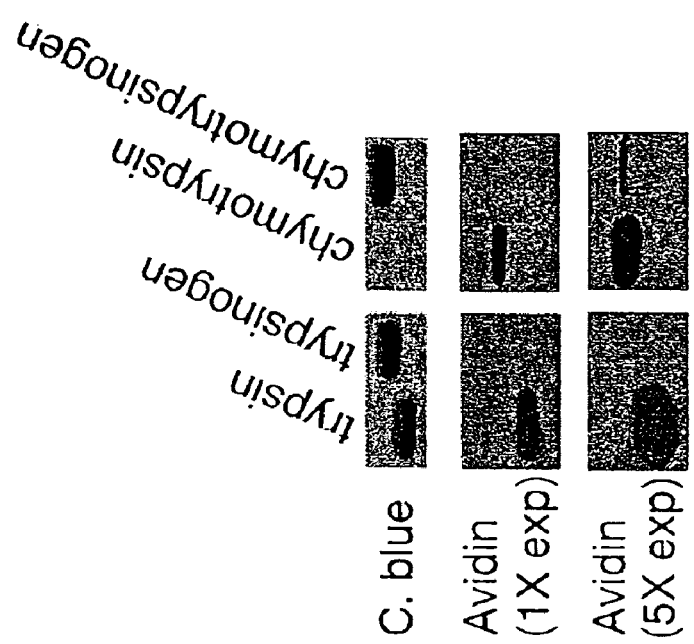
FIG. 19: The serine hydrolase activity profile of Triton-solubilized brain membranes is similar to that of unsolubilized brain membranes (reaction conditions: 1 $\mu$g/$\mu$L protein, 2 $\mu$M FP-biotin, 30 min reaction, 50 mM Tris, pH 8.0, with or without 0.2% Triton X-100).
Figure 20:
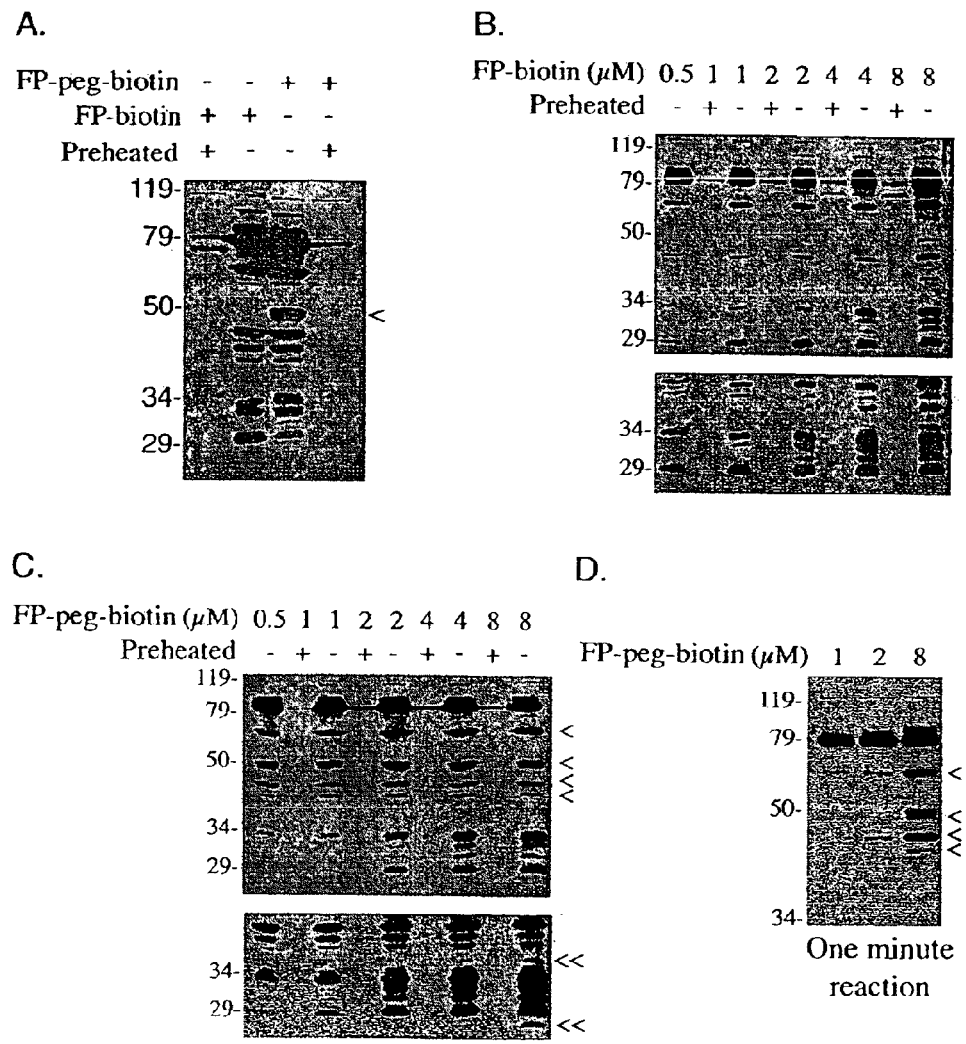
FIG. 20: (A) Kinetic analysis of FP-proteome reactions. Triton-solubilized brain membranes(1 $\mu$g protein/$\mu$L) was treated with 4 $\mu$M of either FP-biotin (left panel) or FP-peg-biotin (right panel) for the indicated reaction times, after which the assays were quenched with 2× SDS-PAGE loading buffer and analyzed by SDS-PAGE-avidin blotting. Serine hydrolase activities that reacted at a faster rate with FP-biotin or FP-peg-biotin are highlighted (single and double arrowheads, respectively). The top and bottom panels represent 1 and 5 minute film exposures, respectively. (B) Multiplexing of biotinylated FPs enhances coverage of active serine hydrolases in complex proteomes. Solubilized brain membrane proteins were treated with the indicated concentrations of biotinylated FPs (30 min reaction). Highlighted are three serine hydrolases that are collectively visualized more clearly in an FP-proteome reaction containing a mixture of FP-biotin and FP-peg-biotin than in reactions conducted with each probe alone (bracket).

Initially, brain membrane proteins were treated with FP-biotin both prior to and after solubilization with Triton X-100 to examine the effects of detergent on the FP-membrane proteome reaction. Similar serine hydrolase activity profiles were observed with membrane-associated and Triton-solubilized brain protein samples (FIG. 19), indicating that detergent solubilization maintained most of the membrane-bound serine hydrolases in a catalytically active state. Therefore, subsequent labeling experiments were conducted with Triton-solubilized brain membrane proteins. Most brain membrane serine hydrolases exhibited rates of FP reactivity that could be monitored over a time course of 1–60 minutes under the following set of reaction conditions: 4 μM biotinylated FP, 1 μg/μL protein, 50 mM Tris buffer, pH 8.0, with 0.2% Triton X-100. Interestingly, examples were observed for each of the three potential types of serine hydrolase reactivity profiles: 1) enzymes that labeled with FP-biotin at faster rates than FP-peg-biotin (FIG. 20A, single arrowhead), 2) enzymes that labeled with FP-peg-biotin at faster rates than FP-biotin (double arrowheads), and 3) enzymes that labeled with FP-biotin and FP-peg-biotin at similar rates (triple arrowheads). In particular, a 65 kDa SH activity was apparently labeled to completion with FP-biotin within one minute (FIG. 20A, left panel), but reacted at a much slower rate with FP-peg-biotin (its signal intensity still increasing from 30 to 60 minutes; FIG. 20A, right panel). We suspected that To demonstrate that this serine hydrolase represents fatty acid amide hydrolase (FAAH), a brain integral membrane enzyme that displays a strong preference for long aliphatic amide substrates, we treated brain membrane proteins with each biotinylated FP and measured FAAH catalytic activity at two time points during the reaction. No FAAH activity could be detected in the FP-biotin treated samples after incubations for either 10 or 60 minutes. In contrast, significant FAAH activity was observed in the FP-peg-biotin treated samples at both time points, with the 10 and 60 minute incubations displaying 60% and 30% FAAH activity, respectively (relative to an untreated control sample). Thus, FAAH was inactivated at a much faster rate by FP-biotin than FP-peg-biotin, consistent with this enzyme's substrate selectivity.

Considering that several brain membrane serine hydrolases reacted preferentially with one biotinylated FP over the other, we showed that by treating a single proteome with a mixture of both probes, a more complete serine hydrolase activity profile is obtained. Treating brain membrane proteins with 2 μM each of FP-biotin and FP-peg-biotin provided a serine hydrolase activity profile that resembled closely the predicted merger of profiles generated with each FP individually (FIG. 20B). These data indicate that adding multiple activity-based probes to a single proteome ("multiplexing") can enhance the coverage of active enzymes present in that sample.

Figure 21:
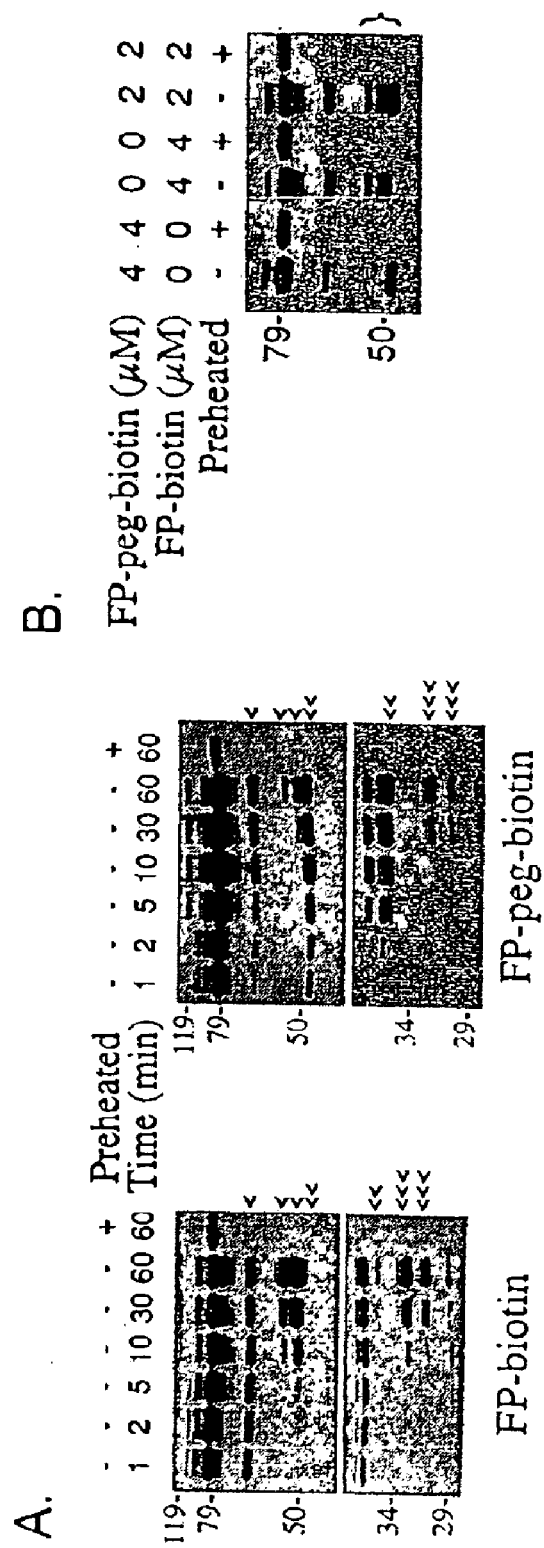
FIG. 21. A comparison of membrane-associated serine hydrolase activities expressed in a panel of rat tissues. Protein samples (1 $\mu$g/$\mu$L) were treated with FP-biotin (4 $\mu$M) for 1 hour (50 mM Tris, pH 8.0, 0.2% Triton), quenched with 2× SDS-PAGE loading buffer, and analyzed by SDS-PAGE/avidin blotting on either a 10% (left panels) or 8% (right panels) polyacrylamide gel. Highlighted are brain-enriched (single arrowheads), heart-enriched (double arrowhead), and testis-enriched (triple arrowhead) serine hydrolase activities.

Comparing the Membrane-Associated Serine Hydrolase Activity Profiles from Different Rat Tissues. Having observed the large number of serine hydrolases associated with brain membranes, we compared the serine hydrolase activity profiles of membrane fractions from a panel of rat tissues. Each membrane fraction was first washed with 1 M NaCl prior to solubilzation of its protein content with Triton X-100. This protocol was selected to enrich for integral membrane proteins, a class of proteins notoriously resistant to analysis by standard proteomics methods. Interestingly, each of the tissues examined possessed a unique and complex profile of membrane-associated serine hydrolase activities (FIG. 21). Notably, a set of three 48–52 kDa serine hydrolase activities were enriched in brain membranes (single arrowhead). Likewise, heart-enriched and testis-enriched serine hydrolase activities were also observed (double and triple arrowheads, respectively).

Figure 22:
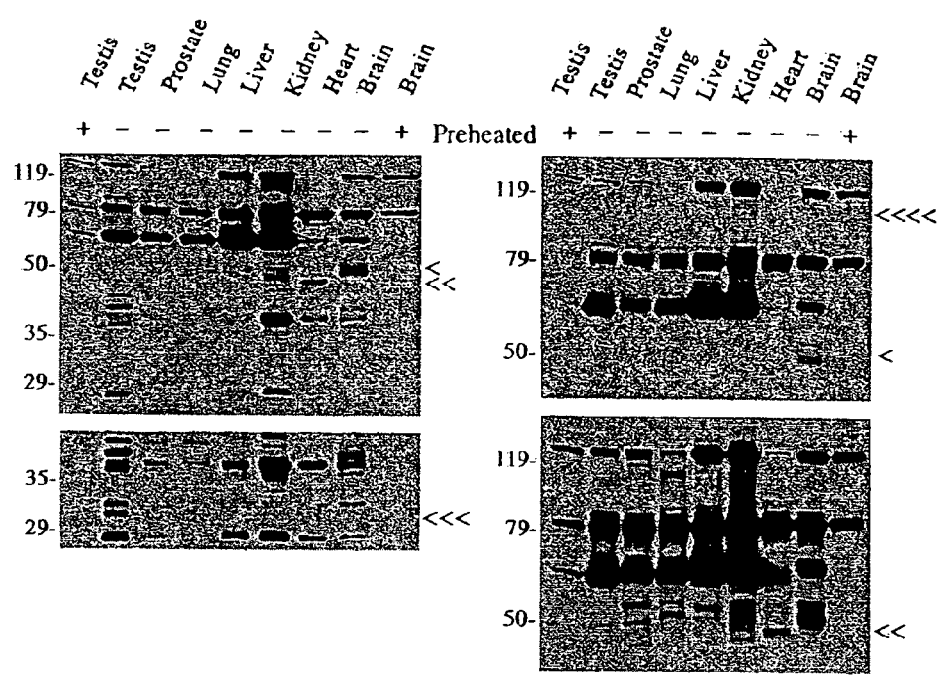
FIG. 22. Evaluating the target selectivity of a noncovalent serine hydrolase inhibitor in complex proteomes. Competition reactions between varying concentrations of oleoyl trifluoromethyl ketone (OTFMK) and biotinylated FPs identifies several brain membrane serine hydrolases targeted by OTFMK. The arrowhead highlights the brain enzyme fatty acid amide hydrolase (FAAH), a known OTFMK target, and the bracket highlights two additional brain membrane serine hydrolases sensitive to OTFMK.

Evaluating the Target Selectivity of Noncovalent Serine Hydrolase Inhibitors. Biotinylated FPs not only distinguish active serine hydrolases from zymogens (FIG. 16), but also from inhibitor-bound enzymes. To demonstrate the target selectivity of serine hydrolase inhibitors directly in complex proteomes, each biotinylated FP was added to a brain membrane proteome treated with varying concentrations of oleoyl trifluoromethyl ketone (OTFMK), a previously described noncovalent FAAH inhibitor. After a 30 minute incubation, the reactions were quenched and analyzed by SDS-PAGE and blotting with avidin. Several serine hydrolases displayed reduced FP-reactivity in the presence of increasing concentrations of OTFMK (FIG. 22) indicating that this electrophilic ketone was not only an effective inhibitor of FAAH, but of other brain membrane serine hydrolases as well. Film densitometry was used to estimate OTFMK's potency as an inhibitor of each of its serine hydrolase targets. A pair of 50 kDa serine hydrolases displayed approximately 40 and 80% reductions in both their FP-biotin and FP-peg-biotin reactivities in the presence of 50 and 200 μM OTFMK, respectively (bracket). In contrast, FAAH's FP-peg-biotin reactivity was reduced by approximately 30, 90, and 95% in the presence of 5, 50, and 200 μM OTFMK, respectively (arrowhead). These data reveal that OTFMK displays a relatively modest (approximately one order of magnitude) selectivity for FAAH among other brain membrane serine hydrolases. Although both 50 and 200 μM concentrations of OTFMK blocked greater than 90% of FAAH's FP-peg-biotin reactivity, this enzyme's FP-biotin reactivity was only weakly affected (~20% reduction) and partially affected (~70% reduction) by 50 μM and 200 μM OTFMK, respectively. These apparently conflicting data can be rationalized as follows. Of the three observed OTFMK-sensitive serine hydrolases, exclusively FAAH reacted with FP-biotin at a rate that was too fast to monitor under the reaction conditions employed (FIG. 19A, left panel). In such a case, the binding of a reversible inhibitor will only be detected if the inhibitor reduces its protein target's rate of FP reactivity to the extent that the protein no longer labels to completion during the time course of the reaction. Thus, FAAH's sensitivity to OTFMK was likely underestimated in the 30 minute FP-biotin competition assay. On the other hand, FP-peg-biotin labeled FAAH at a rate slow enough to be followed over a 60 minute time course (FIG. 19A, right panel), and therefore reactions conducted with this probe provided a more accurate assessment of the sensitivity of FAAH to competitive active site-directed agents. Collectively, these results demonstrate that biotinylated FPs can, in cases where they display discernible labeling kinetics, identify the serine hydrolase targets of noncovalent inhibitors directly in complex proteomes.

Figure 23:
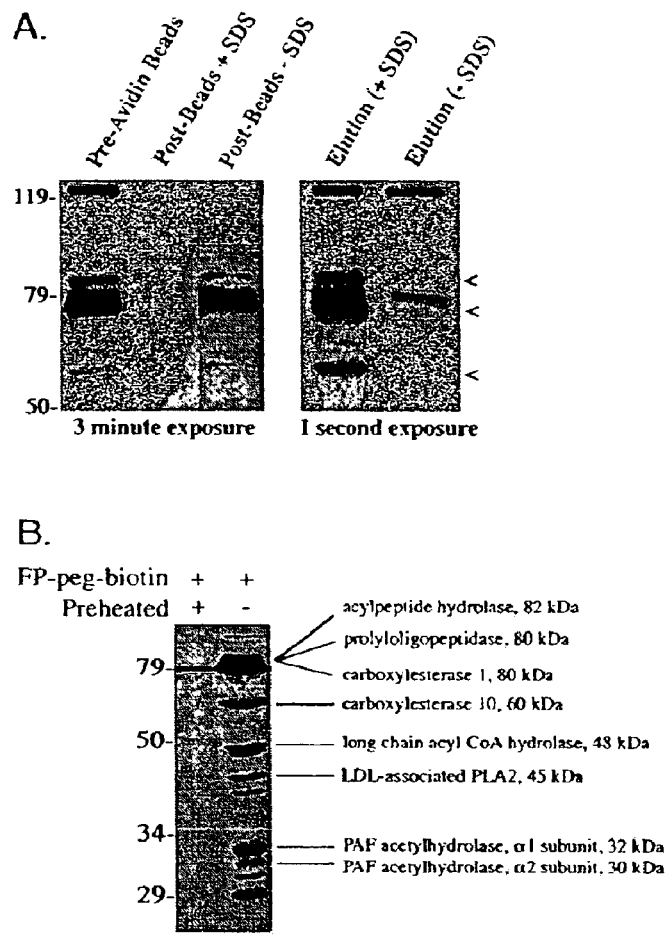
FIG. 23. Affinity isolation and molecular characterization of FP-labeled serine hydrolase activities. (A) Avidin-agarose beads effectively bind denatured, but not native FP-labeled proteins. A sample of FP-biotin-labeled proteins (Pre-Avidin Beads) was mixed with avidin agarose beads with or without a predenaturation step (heating in 1% SDS for 10 at 85° C.) for 1 hour at room temperature. Visualization of the supernatants by SDS-PAGE/avidin blotting (Post-Beads) identified several proteins (arrowheads) that only bound the avidin beads in the SDS-treated sample (+SDS) and were strongly enriched in the corresponding elution fraction (Elution) relative to a control sample (−SDS). Note that the left panel represents a 3 min. exposure, while the right panel represents a 1 sec. exposure. The different exposure times reflect the high degree of concentration of FP-biotin-labeled proteins achieved by this method. (B) Molecular identification FP-biotin-labeled proteins. Eight of the avidin-enriched FP-labeled proteins were excised from an SDS-PAGE gel, digested with trypsin, and the resulting peptides analyzed by MALDI and/or electrospray mass spectrometry. Mass information identified all of these proteins as serine hydrolases (see text for GenBank accession numbers).

Affinity Isolation and Molecular Characterization of FP-Labeled Serine Hyrdrolases. For activity-based probes like the biotinylated FPs to be of lasting use to proteomics research, these reagents must not only serve as tools for protein detection, but also for protein isolation and identification. In the course of attempting to affinity purify FP-biotinylated proteins by avidin agarose chromatography, we noted that several labeled proteins failed to bind the avidin matrix in their native state (FIG. 23A, arrowheads). However, if protein samples were denatured prior to treatment with avidin beads, efficient depletion of all of the biotinylated proteins was achieved. Subsequent washing of the beads and elution with SDS-PAGE loading buffer provided a sample greatly enriched for biotinylated proteins (FIG. 8A, right panel). The elution sample was run on an SDS-PAGE gel and the biotinylated proteins excised from the gel, digested with trypsin, and the resulting peptide mixtures analyzed by MALDI mass spectrometry. This one-step isolation method identified seven of the labeled serine hydrolases present in a soluble rat testis proteome as: acylpeptide hydrolase (82 kDa, accession #CAA33040), prolyl oligopeptidase (80 kDa, BAA25544), carboxylesterase 1 (80 kDa, accession #JX0054), carboxylesterase 10 (60 kDa, accession #P16303), long chain acyl CoA hydrolase (48 kDa, accession #088267), platelet-activating factor (PAF) acetylhydrolase al subunit (32 kDa, accession #NP_032802), and PAF acetylhydrolase a2 subunit (30 kDa, accession #035264) (FIG. 8B). An additional 45 kDa serine hydrolase activity provided a MALDI tryptic peptide map that did not match those of any proteins in the public databases. Analysis of the electrospray MS fragmentation pattern of one of the tryptic peptides from this protein (M+H+=1099 Da) provided the following sequence information: GFVVAAIEHR. BLAST database searches with this peptide sequence identified 80 and 90% identical sequences in the human and dog versions, respectively, of a 45 kDa serine hydrolase referred to as plasma PAF acetylhydrolase or LDL-associated phospholipase A2 (human protein accession #AAB04170.1). Thus, the isolated 45 kDa FP-biotin-reactive testis protein was likely a novel rodent member of this family of secreted serine hydrolases.

Example 7

Sulfonate Ester Combinatorial Library as ABPS

Materials and Methods

Synthesis Alkyl and Aryl Sulfonate Esters.

All reactions were carried out under an atmosphere of argon unless specified. Methylene chloride ($CH_2Cl_2$) was dried by passing through activated alumina columns. Commercial reagents of high purity were purchased and used without further purification unless otherwise noted. NMR spectra were obtained on a Bruker AMX-400 instrument and calibrated to the residual solvent peak. The multiplicities are abbreviated as follows: s=singlet, d=doublet, t=triplet, q=quartet, p=pentet, m=multiplet).

The synthesis of 10-((2-pyridylsulfonyl)oxo)-N-biotinamidopentyldecanamide (1) is provided as a representative synthesis of the eleven biotinylated alkyl and aryl sulfonates (1–11).

((2-Pyridylsulfonyl)oxo)-10-undecene (13): A solution of α-undecylenyl alcohol (12)(0.50 g, 2.91 mmol, 1.0 equivalents (equiv.)) in pyridine (4 mL) was cooled to 0° C. and treated with 2-pyridylsulfonyl chloride (1.04 g, 5.87 mmol, 2.0 equiv.), prepared according to the procedure of Corey and colleagues [Corey, et al. (1989). J. Org. Chem. 54, 389–93]. The reaction mixture was kept at 0° C. for 6 hours, then partitioned between ethyl acetate (50 mL) and water (25 mL). The organic layer was washed with 10% aqueous HCl (2×50 mL) and saturated aqueous NaCl (50 mL), dried ($MgSO_4$), and concentrated under reduced pressure. Column chromatography (2% EtOAc/Hex) afforded 13 as a colorless oil (98%): $^1$H NMR (CDCl$_3$, 400 MHz) δ 8.61 (m, 1H, ArH), 7.89 (m, 2H, ArH), 7.47 (m, 1H, ArH), 5.67–5.60 (m, 1H, RCH=CH$_2$), 4.84–4.74 (m, 2H, RCH=CH$_2$), 4.21 (t, J=6.4 Hz, 2H, CH$_2$OSO$_2$Pyr), 1.88 (m, 2H CH$_2$CH=CH$_2$), 1.55 (p, 2H, J=6.8 Hz, 2H, CH$_2$CH$_2$OSO$_2$Pyr), 1.20–1.08 (m, 12H); matrix-assisted laser desorption ionization (MALDI)-FTMS 334.1433 (C$_{16}$H$_{25}$NO$_3$S+Na$^+$ requires 334.1447).

10-((2-Pyridylsulfonyl)oxo)-decanoic acid (14): Compound 13 (0.90 g, 2.88 mmol, 1 equiv.) in a biphasic solution composed of CCl$_4$-CH$_3$CN-H$_2$O (10 mL-10 mL-15 mL) with a total volume of 35 mL was treated sequentially with sodium periodate (2.53 g, 11.80 mmol, 4.1 equiv.) and ruthenium trichloride hydrate (0.005 g, 0.02 mmol, 0.03 equiv.). The reaction was stirred at 25° C. overnight then partitioned between CH$_2$Cl$_2$ (100 mL) and 1N aqueous HCl (2×100 mL). The organic layer was washed with saturated aqueous NaCl (100 mL), dried (MgSO$_4$) and concentrated under reduced pressure. Column chromatography (40% EtOAc/Hex) afforded 14 (80%): $^1$H NMR (CDCl$_3$, 400 MHz) δ 8.84 (d, J=4.0 Hz, 1H, ArH), 8.11 (d, J=5.9 Hz, 1H, ArH), 8.05 (t, J=6.0 Hz, 1H, ArH), 7.65 (t, J=3.3 Hz, 1H, ArH), 4.37 (t, J=6.6 Hz, 2H, CH$_2$OSO$_2$Pyr), 2.34 (t, J=7.4 Hz, 2H, CH$_2$COOH), 1.70 (p, J=8.0 Hz, 2H, CH$_2$CH$_2$COOH), 1.61 (p, J=7.3 Hz, 2H, CH$_2$CH$_2$OSO$_2$Pyr), 1.25 (m, 10H): MALDI-FTMS (DHB) m/z 352.1202 (C$_{15}$H$_{23}$NO$_5$S+Na$^+$ requires 352.1189).

10-((2-Pyridylsulfonyl)oxo)-N-biotinamidopentyldecanamide (1): A solution of 14 (0.030 g, 0.09 mmol, 10 equiv.) in CH$_2$Cl$_2$ (1.5 mL) at −78° C. was treated dropwise with (diethylamino)sulfur trifluoride (0.027 mL, 0.21 mmol, 22 equiv.), brought to 25° C., and stirred for 10 minutes. The reaction was then treated with one-half reaction volume of dimethylformamide containing N-hydroxysuccinimide (0.05 g, 0.04 mmol, 40 equiv.) and stirred for an additional 15 min at 25° C. The reaction mixture was partitioned between ethyl acetate (50 mL) and water (50 mL). The organic layer was washed with saturated aqueous NaCl (200 mL), dried (Na$_2$SO$_4$), and concentrated under reduced pressure to afford 10-((2-pyridylsulfonyl)oxo)-N-(hydroxysuccinyl)decanamide (as judged by crude $^1$H NMR; data not shown). Without further purification, the intermediate was treated with 5-(biotinamido)-pentylamine (Pierce, 0.003 g, 0.009 mmol, 1.0 equiv.) in MeOH (0.04 mL) and stirred for 30 min. The solvent was evaporated under a stream of nitrogen, and the remaining residue was washed with ethyl acetate (2×2.5 mL), solubilized in a minimal volume of chloroform, transferred to a clean glass vial, and the solvent evaporated. This process was repeated to rid the desired biotinylated product of excess reagents and byproducts, affording 4 as a white film (0.004 g, 46%): $^1$H NMR (CDCl$_3$, 400 MHz) δ 8.79 (d, J=7.0 Hz, 1H, ArH), 8.06 (m, 2H, ArH), 7.61 (t, J=7.3 Hz, 1H, ArH), 6.05 (b s, 1H, NH), 5.91 (b s, 1H, NH), 5.60 (b s, 1H, NH), 4.77 (b s, 1H, NH), 4.54 (m, 1H), 4.39 (m, 1H+2H CH$_2$OSO$_2$R), 3.22 (m, 4H, CH$_2$NHCOR), 3.11 (m, 1H), 2.92 (dd, J=4.0 and 12.9 Hz, 1H), 2.76 (d, J=13.3 Hz, 1H), 2.18 (m, 4H, CH$_2$CONHR), 1.67–1.28 (m, 26H); MALDI-FTMS (DHB) m/z 640.3209 (C$_{30}$H$_{49}$N$_5$O$_6$S$_2$+H$^+$ requires 640.3202).

10-((Benzenesulfonyl)oxo)-N-biotinamidopentyldecanamide (2): $^1$H NMR (CDCl$_3$, 400 MHz) δ 7.93 (d, J=7.0 Hz, 2H, ArH), 7.67 (t, J=7.4 Hz, 1H, ArH), 7.59 (t, J=7.3 Hz, 2H, ArH), 6.06 (b s, 1H, NH), 5.87 (b s, 1H, NH), 5.63 (b s, 1H, NH), 4.79 (b s, 1H, NH), 4.53 (m, 1H), 4.37 (m, 1H), 4.07 (t, J=6.4 Hz, 2H, CH$_2$OSO$_2$R), 3.26 (m, 4H, CH$_2$HNCOR), 3.09 (m, 1H), 2.93 (dd, J=5.0 and 7.9 Hz, 1H), 2.76 (d, J=13.0 Hz, 1H), 2.19 (m, 4H, CH$_2$CONHR), 1.62–1.26 (m, 26H); MALDI-FTMS (DHB) m/z 639.3244 (C$_{31}$H$_{50}$N$_4$O$_6$S$_2$+H$^+$ requires 639.3245).

10-((p-Toluenesulfonyl)oxo)-N-biotinamidopentyldecanamide (3): $^1$H NMR (CDCl$_3$, 400 MHz) δ 7.78 (d, J=8.5 Hz, 2H, ArH), 7.37 (d, J=7.9 Hz, 2H, ArH), 5.91 (b s, 1H, NH), 5.84 (b s, 1H, NH), 5.49 (b s, 1H, NH), 4.76 (b s, 1H, NH), 4.53 (m, 1H), 4.35 (m, 1H), 4.02 (t, J=6.4 Hz, 2H, CH$_2$SO$_2$R), 3.25 (m, 4H, CH$_2$NHCOR), 3.18 (m, 1H), 2.93 (dd, J=5.0 and 7.9 Hz, 1H), 2.76 (d, J=12.9 Hz, 1H), 2.46 (s, 3H, CH$_3$Ar), 2.19 (m, 4H, CH$_2$CONHR), 1.70–1.50 (m, 26H); MALDI-FTMS (DHB) m/z 653.3381 (C$_{32}$H$_{52}$N$_4$O$_6$S$_2$+H$^+$ requires 653.3401).

10-((4-Methoxybenzenesulfonyl)oxo)-N-biotinamidopentyldecanamide (4): $^1$H NMR (CDCl$_3$, 400 MHz) δ 7.86 (d, J=8.8 Hz, 2H, ArH), 7.03 (d, J=8.8 Hz, 2H, ArH), 5.96 (b s, 1H, NH), 5.85 (b s, 1H, NH), 5.57 (b s, 1H, NH), 4.84 (b s, 1H, NH), 4.53 (m, 1H), 4.37 (m, 1H), 4.01 (t, J=6.5 Hz, 2H, CH$_2$OSO$_2$R), 3.90 (s, 3H, CH$_3$OAr), 3.25 (m, 4H, CH$_2$NHCOR), 3.17 (m, 1H), 2.95 (dd, J=4.7 and 7.7 Hz, 1H), 2.73 (d, J=12.9 Hz, 1H), 2.25 (m, 4H, CH$_2$CONHR), 1.63–1.26 (m, 26H); MALDI-FTMS (DHB) m/z 669.3381 (C$_{32}$H$_{52}$N$_4$O$_7$S$_2$+H$^+$ requires 669.335).

10-((Methylsulfonyl)oxo)-N-biotinamidopentyldecanamide (5): $^1$H NMR (CDCl$_3$, 400 MHz), δ 6.00 (b s, 1H, NH), 5.85 (b s, 1H, NH), 5.60 (b s, 1H, NH), 4.81 (b s, 1H, NH), 4.53 (m, 1H), 4.37 (m, 1H), 4.35 (t, J=6.2 Hz, 2H, CH$_2$OSO$_2$R), 3.26 (m, 4H, CH$_2$HNCOR), 3.18 (m, 1H), 2.93 (dd, J=5.0 and 7.9 Hz, 1H), 2.76 (d, J=12.9 Hz, 1H), 2.21 (m, 4H, CH$_2$CONHR), 2.05 (s, 3H, H$_3$CSO$_3$R), 1.75–1.27 (m, 26H); MALDI-FTMS m/z 577.3105 (C$_{26}$H$_{48}$N$_4$O$_6$S$_2$+H$^+$ requires 577.3088).

10-((Butylsulfonyl)oxo)-N-biotinamidopentyldecanamide (6): $^1$H NMR (CDCl$_3$, 400 MHz) δ 5.93 (b s, 1H, NH), 5.84 (b s, 1H, NH), 5.53 (b s, 1H, NH), 4.82 (b s, 1H, NH), 4.54 (m, 1H), 4.37 (m, 1H), 4.21 (t, J=6.2 Hz, 2H, CH$_2$OSO$_2$R), 3.26 (m, 4H, CH$_2$NHCOR), 3.19 (m, 1H), 3.09 (t, J=4.1 Hz, 2H, CH$_2$SO$_3$R), 2.93 (dd, J=4.6 and 7.4 Hz, 1H), 2.76 (d, J=9.1 Hz, 1H), 2.21 (m, 4H, CH$_2$CONHR), 2.16–1.31 (m, 30H), 0.97 (t, J=7.3 Hz, 3H); MALDI-FTMS (DHB) m/z 619.3530 (C$_{29}$H$_{54}$N$_4$O$_6$S$_2$+H$^+$ requires 619.3530).

10-((Octylsulfonyl)oxo)-N-biotinamidopentyldecanamide (7): $^1$H NMR (CDCl$_3$, 400 MHz) δ 6.05 (b s, 1H, NH), 5.87 (b s, 1H, NH), 5.81 (b s, 1H, NH), 5.00 (b s, 1H, NH), 4.53 (m, 1H), 4.35 (m, 1H), 4.21 (t, J=6.2 Hz, 2H, CH$_2$OSO$_2$R), 3.25 (m, 4H, CH$_2$NHCOR), 3.17 (m, 1H), 3.09 (t, J=8.5 Hz, 2H, CH$_2$SO$_3$R), 2.93 (dd, J=4.7 and 7.9 Hz, 1H), 2.76 (d, J=12.9 Hz, 1H), 2.19 (m, 4H, CH$_2$CONHR), 1.86 (p, J=7.9 Hz, 2H, CH$_2$CH$_2$SO$_3$R), 1.76–1.31 (m, 36H), 0.89 (t, J=6.4 Hz, 3H); MALDI-FTMS (DHB) m/z 675.4173 (C$_{33}$H$_{62}$N$_4$O$_6$S$_2$+H$^+$ requires 675.4184).

10-((4-Nitrobenzenesulfonyl)oxo)-N-biotinamidopentyldecanamide (8): $^1$H NMR (CDCl$_3$, 400 MHz), δ 8.44 (d, J=9.1 Hz, 2H, ArH), 8.14 (d, J=9.1 Hz, 2H, ArH), 5.90 (b s, 1H, NH), 5.82 (b s, 1H, NH), 5.50 (b s, 1H, NH), 4.86 (b s, 1H, NH), 4.54 (m, 1H), 4.37 (m, 1H), 4.14 (t, J=6.5 Hz, 2H, CH$_2$OSO$_2$R), 3.25 (m, 4H, CH$_2$NHCOR), 3.18 (m, 1H), 2.96 (dd, J=5.0 and 7.9Hz, 1H), 2.76 (d, J=15.0 Hz, 1H), 2.21 (m, 4H, CH$_2$CONHR), 1.72–1.26 (m, 26H); MALDI-FTMS (DHB) m/z 684.3069 (C$_{31}$H$_{49}$N$_5$O$_8$S$_2$+H$^+$ requires 684.3095).

10-((8-Quinolinesulfonyl)oxo)-N-biotinamidopentyldecanamide (9): $^1$H NMR (CDCl$_3$, 400 MHz) δ 9.17 (m, 1H, ArH), 8.53 (d, J=5.8 Hz, 1H, ArH), 8.50 (d, J=6.4 Hz, 1H, ArH), 8.16 (d, J=6.7 Hz, 1H, ArH), 7.70 (t, J=7.6 Hz, 1H, ArH), 7.61 (q, J=3.9 Hz, 1H, ArH), 6.06 (b s, 1H, NH), 5.93 (b s, 1H, NH), 5.73 (b s, 1H, NH), 5.08 (b s, 1H, NH), 4.54 (m, 1H), 4.35 (m, 1H), 4.30 (t, J=6.5 Hz, 2H, $CH_2OSO_2R$), 3.27 (m, 4H, $CH_2NHCOR$), 3.18 (m, 1H), 2.96 (dd, J=5.0 and 7.9 Hz, 1H), 2.77 (d, J=15 Hz, 1H), 2.21 (m, 4H, $CH_2CONHR$), 1.68–1.18 (m, 26H); MALDI-FTMS 712.3189 ($C_{34}H_{51}N_5O_6S_2$+$Na^+$ requires 712.3173).

10-((2-Naphthalenesulfonyl)oxo)-N-biotinamidopentyl-decanamide (10): $^1H$ NMR ($CDCl_3$, 400 MHz) δ 8.49 (s, 1H, ArH), 7.98 (t, J=8.2 Hz, 2H, ArH), 7.93 (d, J=7.9 Hz, 1H, ArH), 7.87 (d, J=8.8 Hz, 1H, ArH), 7.65 (p, J=7.0 Hz, 2H, ArH), 6.05 (b s, 1H, NH), 5.91 (b s, 1H, NH), 5.60 (b s, 1H, NH), 4.77 (b s, 1H, NH), 4.53 (m, 1H), 4.37 (m, 1H), 4.06 (t, J=6.4 Hz, 2H, $CH_2OSO_2R$), 3.25 (m, 4H, $CH_2CONHR$), 3.17 (m, 1H), 2.95 (dd, J=5.0 and 7.6 Hz, 1H), 2.77 (d, J=14.0 Hz), 2.17 (m, 4H, $CH_2CONHR$), 1.71–1.20 (m, 26H); MALDI-FTMS (DHB) m/z 689.3379 ($C_{35}H_{52}N_4O_6S_2$+$H^+$ requires 689.3401).

10-((2-Thiophenesulfony)oxo)-N-biotinamidopentyl) decanamide (11): $^1H$ NMR ($CDCl_3$, 400 MHz) δ 7.74 (t, J=5.0 Hz, 2H, ArH), 7.16 (t, J=3.8 Hz, 1H, ArH), 5.90 (b s, 1H, NH), 5.84 (b s, 1H, NH), 5.47 (b s, 1H, NH), 4.75 (b s, 1H, NH), 4.53 (m, 1H), 4.35 (m, 1H), 4.12 (t, J=6.4 Hz, 2H, $CH_2OSO_2R$), 3.26 (m, 4H, $CH_2NHCOR$), 3.19 (m, 1H), 2.95 (dd, J=5.3 and 7.6 Hz, 1H), 2.76 (d, J=12.9 Hz, 1H), 2.17 (m, 4H, $CH_2CONHR$), 1.67–1.26 (m, 26H); MALDI-FTMS (DHB) m/z 645.2817 ($C_{29}H_{48}N_4O_6S_3$+$H^+$ requires 645.2809).

1-(2-Pyridylsulfonyl)oxo-octane (15): To 3.0 mL of anhydrous triethylamine (23.04 mmol, 30 equiv.) at 0° C. was added 1-octanol (0.10 g 0.77 mmol, 1 equiv.) followed by the addition of 2-pyridylsulfonyl chloride in one portion. The mixture was kept at 0° C. for 3 hours followed by the addition of water (5 mL). The resulting mixture was extracted with diethyl ether (3×50 mL), then the organic extracts were combined and washed with aqueous $NaHCO_3$ solution (50 mL), dried ($MgSO_4$), and concentrated under reduced pressure. Column chromatography (2% EtOAc/Hex) afforded 15 (99%): $^1H$ NMR ($CDCl_3$, 400 MHz) δ 8.68 (d, J=7.0 Hz, 1H, ArH), 7.94 (p, J=8.8 Hz, 2H, ArH), 7.54 (t, J=6.4 Hz, 1H, ArH), 4.26 (t, J=6.7 Hz, 2H, $CH_2OSO_2R$), 1.61 (p, J=7.9 Hz, 2H), 1.13 (m, 10H), 0.76 (t, J=7.0 Hz, 3H); MALDI-FTMS 294.1130 ($C_{13}H_{21}NO_3S$+$Na^+$ requires 294.1134).

1-(2-Pyridylsulfonyl)oxo-ethane (16): To a solution of triethylamine (0.86 g, 8.51 mmol, 2.2 equiv.) in dichloromethane (3 mL) at 0° C. was added ethanol (0.18 g, 3.87 mmol, 1 equiv.) followed by the addition of 2-pyridylsulfonyl chloride (0.83 g, 4.65 mmol, 1.2 equiv.). After stirring for 4 hours at 0° C., the solution was concentrated under reduced pressure. The concentrate was dissolved in aqueous $NaHCO_3$ solution (50 mL) and extracted with diethyl ether (3×50 mL). The ether extracts were combined and washed with aqueous NaCl (50 mL), dried ($MgSO_4$), and concentrated under reduced pressure. Column chromatography (5% EtOAc/Hex) afforded 16 (95%): 1H NMR ($CDCl_3$, 400 MHz) δ 8.70 (d, J=4.7 Hz, 1H, ArH), 7.95 (p, J=6.4 Hz, 2H, ArH), 7.56 (t, J=5.3 Hz, 1H, ArH), 4.37 (q, J=7.0 Hz, 2H, $CH_2OSO_2R$), 1.29 (t, J=7.0 Hz, 3H); MALDI-FTMS 188.0000 ($C_6H_9NOS$+$H^{30}$ requires 188.0376).

1-(Methanesulfonyl)oxo-octane (17): To a solution of triethylamine (0.12 g, 1.15 mmol, 1.5 equiv.) in dichloromethane (3 mL) was added octanol (0.10 g, 0.77 mmol, 1.0 equiv.) at 0° C. followed by the addition of methanesulfonyl chloride (0.10 g, 0.85 mmol, 1.1 equiv.), over a period of 5 minutes. After 30 minutes at 0° C., the reaction mixture was diluted in dichloromethane (50 mL) and extracted with ice cold water (50 mL), ice cold 10% aqueous HCl (50 mL), saturated aqueous $NaHCO_3$ (50 mL), and with saturated aqueous NaCl (50 mL). The organic layer was dried ($MgSO_4$) and concentrated under reduced pressure to afford 17 (97%): $^1H$ NMR ($CDCl_3$, 400 MHz) δ 4.21 (t, J=6.5 Hz, 2H, $CH_2OSO_2Me$), 2.99 (s, 3H, $CH_3SO_3$), 1.77 (p, J=6.7 Hz, 2H), 1.35 (m, 10H), 0.87 (t, J=6.1 Hz, 3H).

Proteome Sample Preparation, Labeling, and Detection.

Rat tissues were Dounce-homogenized in Tris buffer (50 mM Tris-HCl buffer, pH 8.0, 0.32 M sucrose). Tissue extracts were centrifuged sequentially at 1,100×g (10 min), 22,000×g (30 min), and 105,000×g (60 min). The final supernatant (soluble fraction) was adjusted to 0.5 mg protein/mL with Tris buffer (without sucrose) and kept at 0° C. until utilized. Unless otherwise indicated, reactions between protein samples and biotinylated reagents were conducted as follows: all biotinylated reagents were stored as stock solutions in DMSO at 20° C. and then added directly to reactions with protein extracts, keeping the DMSO concentration constant at 1% of the total reaction volume. The reaction mixture was incubated at 25° C. for 30 min (final concentration of the probe was 5 μM), then quenched by the addition of 1 vol. equiv. of standard 2× SDS-PAGE loading buffer (reducing). Quenched reactions were run on SDS-PAGE (7.5 μg protein/gel lane) and transferred by electroblotting onto nitrocellulose membranes, which were blocked in Tris-buffered saline (TBS) with 1% Tween (TBS-Tween) and 3% (wt/vol) nonfat dry milk for either 1 h at 25° C. or overnight at 4° C. Blots were then treated with an avidin-horseradish peroxidase conjugate (Bio-Rad, 1:1,500 dilution) in TBS-Tween for 2 hr at 25° C. The blot was washed with TBS-Tween three times (5 min/wash), treated with SuperSignal chemiluminescence reagents (Bio-Rad), and exposed to film for 0.1 to 20 min before development. For the pH-dependence studies, the following reaction buffers were used; pH 6–8: 50 mM Tris.HCl; pH 8–10: 50 mM Tris.HCl, 50 mM CAPS.

Enrichment and molecular characterization of a 55 kDa sulfonate-reactive protein. Rat liver soluble fractions were run over a Q Sepharose column by using an AKTA FPLC (Amersham Pharmacia Biotech) and eluted with a linear gradient of 0–500 mM NaCl. Aliquots of the elution fractions (10×2.5 mL fractions) as well as the flow through (3×2.5 mL fractions) were labeled with 1 as described above to identify the fractions containing the labeled proteins. The flow-through fractions, which contained the 55 kDa protein, were concentrated to a volume of 1 mg protein/mL vol. followed by labeling 2.5 mL of the sample with 1 utilizing the standard conditions. After incubating the reaction for thirty minutes, it was applied to a PD-10 size exclusion column and eluted with 3.5 ml of pH 8, 50 mM Tris-HCl buffer. Sodium dodecyl sulfate (SDS) (0.5% wt/vol) was added and the labeled samples heated to 90° C. for 10 mn in order to denature the proteins allowing for a more accessible biotin moiety. The sample was then diluted 2.5 fold (0.2% SDS) and incubated with 50–100 μL of avidin beads on a rotator for 1 hour at 25° C. The eluant was then removed followed by washing with 5 ml of 0.2% SDS and three washes with pH 8, 50 mM Tris-HCl buffer. Standard 2× SDS-PAGE loading buffer was added followed by heating the sample to 90° C. in order to elute the proteins labeled with 1 from the avidin beads. The eluant was run on an 8% Novex Tris-Glycine gel and stained with Coomasie blue stain followed by destaining in a 30% methanol-water solution. The desired 55 kDa 1-reactive-protein was excised from the gel and digested with trypsin. The resulting peptides were analyzed by matrix assisted laser desorption time-of-flight (MALDI-TOF) mass spectrometry. The MALDI peptide data was utilized in both the MS-Fit search of the Protein Prospector databases (falcon.ludwig.ucl.ac.uk/mskome3.2.htm) and the ProFound search of the Proteometrics databases (found on the world wide web at [www.]proteornetrics.com/prowl cgi/ProFound.exe), which identified the protein as cytosolic 2 class I rat aldehyde dehydrogenase (cALDH-I).

Recombinant Expression and Purification of cALDH-I.

Primers were designed based on cALDH-I's cDNA sequence and used to amplify the enzyme's cDNA from a liver cDNA library (Clontech). The cALDH-I cDNA was subcloned into the prokaryotic expression vector, TrcHisA, followed by transformation and expression in E. coli BL-21 cells. Expression was induced with 1 mM isopropyl α-D thiogalactoside (IPTG) when cultures grew to an $OD_{600}$ of 0.6. After 4 h, the cells were pelleted and the supernatant removed. The cell pellet was resuspended in Tris buffer (20 mM Tris-HCl buffer, pH 8.0, 100 mM NaCl), lysed by treatment with lysozyme (1 mg/ml) for 30 min and then sonication. The soluble fraction was isolated by centrifugation 39,800×g (25 min). The His-tagged cALDH-I was purified from the soluble fraction by rotating with Talon cobalt beads for 30 minutes at 4° C. followed by centrifugation and removal of the lysate. After washing, the beads were eluted with 80 mM imidazole buffer and the eluted protein concentrated to 10 mg protein/mL. The concentrated protein solution was subjected to gel filtration chromatography (Superose 6 column, AKTA FPLC, Amersham Pharmacia Biotech). Gel filtration samples containing purified cALDH-I were combined, concentrated, and stored at −78° C. in Tris buffer containing 1 mM DTT (final cALDH-I protein concentration, 1.5 mg/mL).

Expression of cALDH-I in Eukaryotic Cells.

The cALDH-I cDNA was subcloned into the eukaryotic expression vector pcDNA3 and transiently transfected into COS-7 cells and MCF-7 cells by using methods described previously [Liu, et al. (1999) Proc. Natl. Acad. Sci. USA 96, 14694–99]. Transfected cells were harvested by scraping, resuspended in Tris buffer and their protein concentrations determined ($D_0$ protein assay kit, Bio-Rad). Whole cell suspensions were labeled with 1 as described above.

cALDH-I Enzyme Assay and Inhibition Studies.

cALDH-I activity was determined at 25° C. in Tris buffer (20 mM Tris-HCl, pH 8, 100 mM NaCl). Purified cALDH-I (0.2 μM) was preincubated with 15 (2.5 μM–15 μM) in DMSO (30 μL, 3% total incubation vol) in a volume of 950 μL for 5 to 45 min. After preincubation of the enzyme with inhibitor, remaining catalytic activity was measured by adding $NAD^+$ (500 μM final concentration) and propionaldehyde (1 mM final concentration) in 50 μL of buffer. Production of NADH from the oxidation of propionaldehyde was monitored by measuring the change in absorbance at 340 nm for 2 min. In substrate competition assays, purified cALDH-I (0.2 μM) was preincubated with either $NAD^+$ (50 μM) or propionaldehyde (25 μM) and 10 μM of 15 for 10 minutes at 25° C. in a volume of 950 μL. Remaining catalytic activity was monitored as described above.

Results

Figure 9:
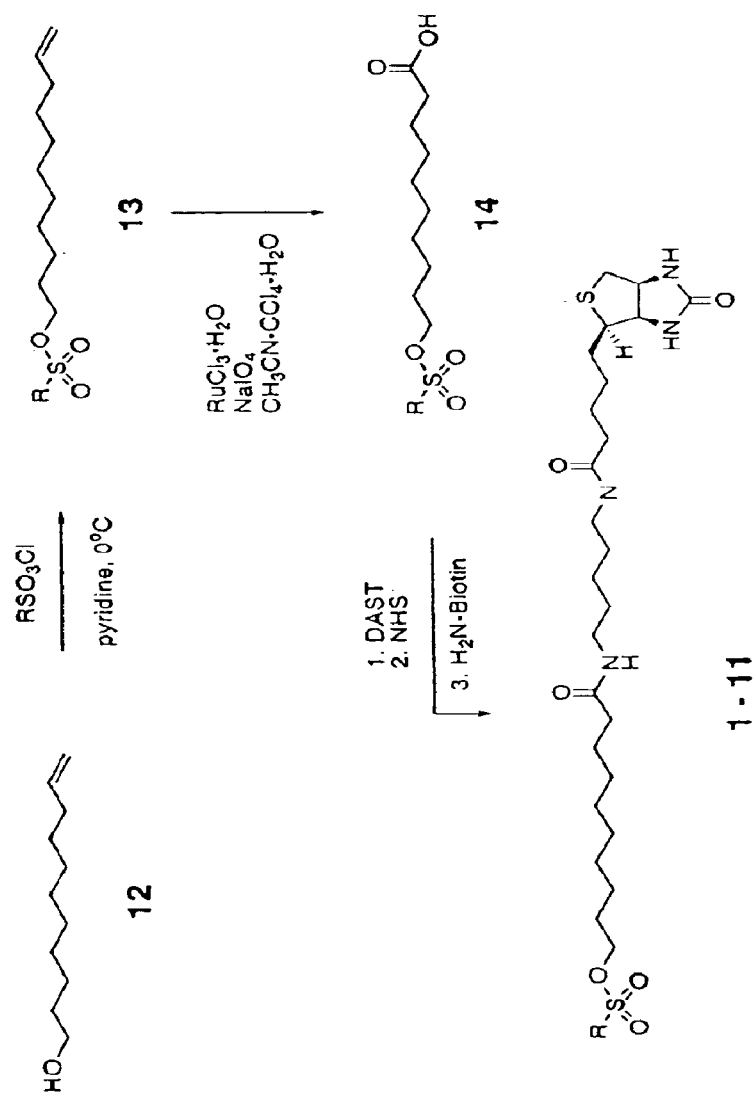
FIG. 9 is an exemplary synthetic route for the generation of biotinylated sulfonate esters.

Selection and synthesis of biotinylated sulfonate esters as candidate ABPs A library of candidate ABPs was synthesized based on the general scaffold outlined in FIG. 9. The structure of an ABP was conceptually divided into four pieces: a binding group (BG), a reactive group (RG), a linker (L), and a tag (T). The library's reactive group was selected as a sulfonate ester, based on the following criteria.

Figure 10:
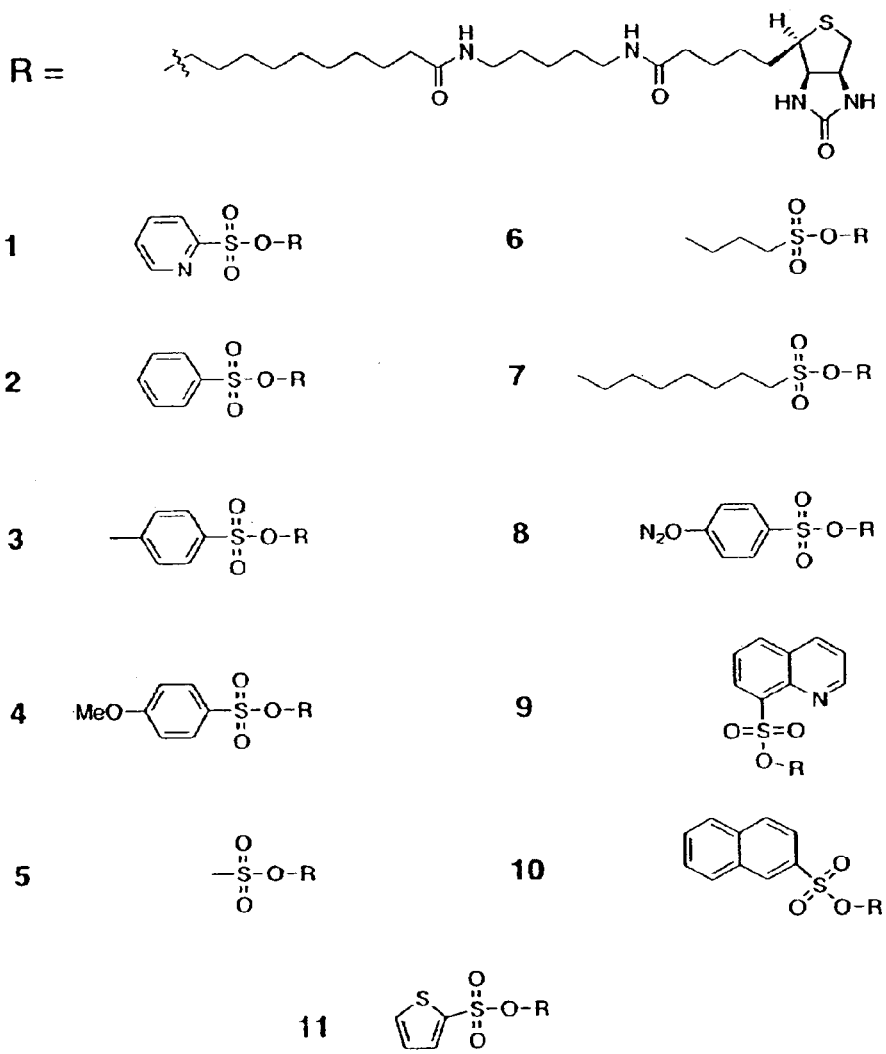
FIG. 10, A, General structure of an activity-based probe (ABP), highlighting the probe's four main components: a binding group (BG), a reactive group (RG), a linker (L), and a tag (T). B, Structures of members of an ABP library, where the BG is varied, the RG is a sulfonate ester, the L is an extended alkyl chain, and the T is biotin.

A series of biotinylated sulfonates (1–11; FIG. 10) was synthesized according to the three step sequence outlined in Scheme 1. The corresponding aryl or alkylsulfonyl chloride was added slowly to a solution of undecene-1-ol (12) dissolved in pyridine at 0° C. to form the sulfonate (13). The procedure of Sharpless and colleagues was utilized to oxidatively cleave the terminal olefin, resulting in formation of the corresponding carboxylic acid (14) [Carlsen, et al (1981) J. Org. Chem. 46, 3936–38]. Treatment of 14 with diethylaminosulfur trifluoride (DAST) followed by the addition of N-hydroxysuccinimide afforded the N-hydroxysuccinimidyl ester intermediate. The latter compound was reacted with commercially available 5-(biotinamido)pentylamine ($NH_2$-biotin, Pierce) in methanol to form the desired biotinylated sulfonate ester.

Figure 11:
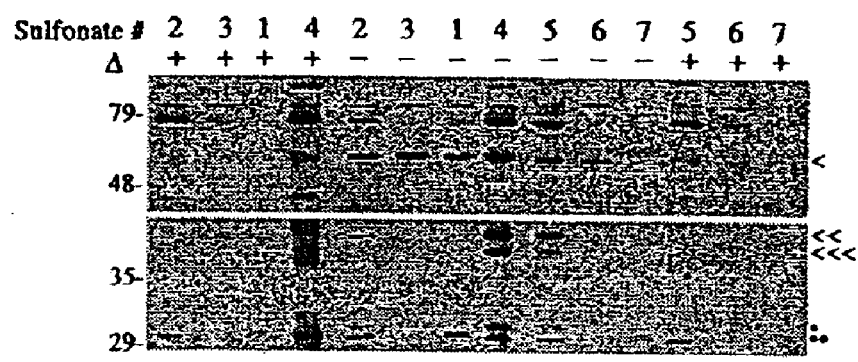
FIG. 11 shows specific and nonspecific proteome reactivities of sulfonates 1–7 (A) and 8–11 (B). For A and B, each sulfonate's reactivity with both a heated and unheated version of a rat testis proteome is shown (standard reaction conditions: 5 μM sulfonate, 0.5 μg/μL testis protein, 50 mM Tris.HCl, pH 8.0, 100 mM NaCl; 30 min reaction, 25° C.). Sulfonate-labeled proteins were detected by SDS-PAGE (7.5 μg protein/lane) and avidin blotting. Highlighted with arrowheads and dots are proteins that reacted with sulfonates in a heat-sensitive manner. The proteins labeled in the lanes containing preheated proteomes (D) were all considered "nonspecific" sulfonate reactivities, except an 80 kDa protein which represented an endogenous avidin-reactive protein (i.e., also observed in proteomes not treated with sulfonates; see FIG. 13B). Different film exposure times are presented for the high (45–100 kDa, 1× time exposure) and low (27–45 kDa, 4× time exposure) molecular mass proteins to permit the signals of labeled proteins to be shown prior to film saturation.
Figure 11:
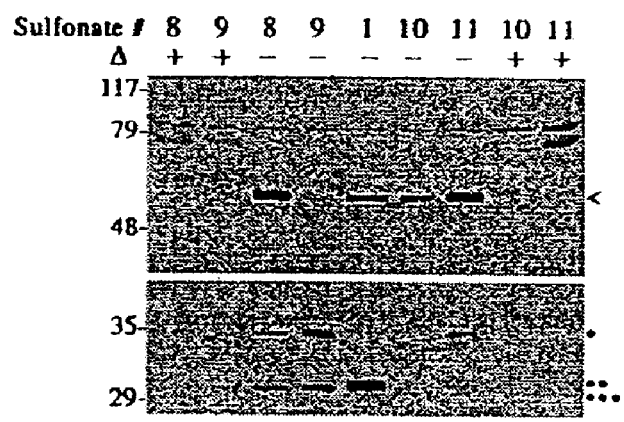
Figure 12:
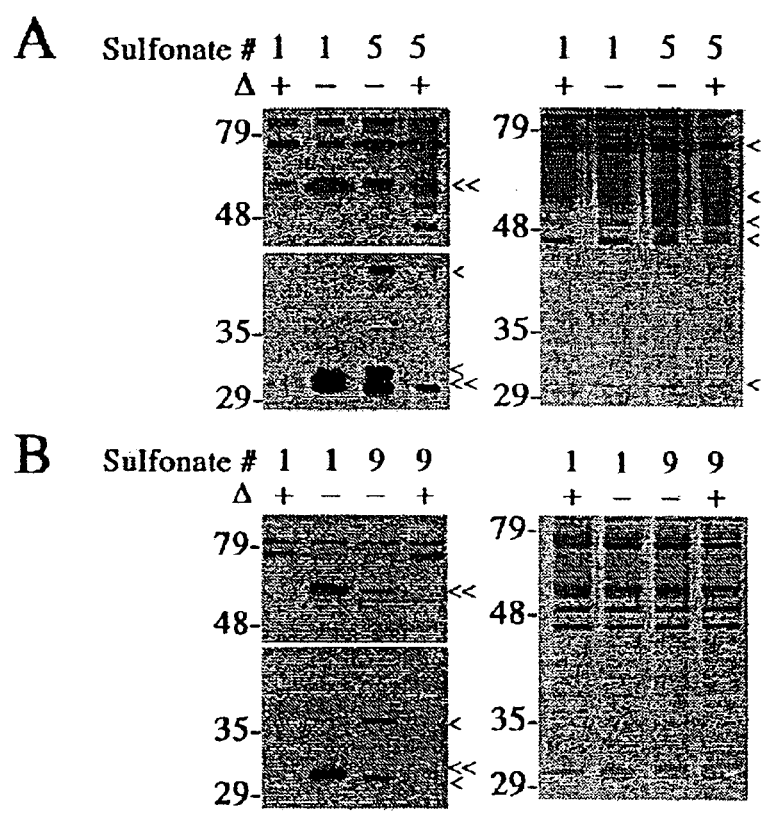
FIG. 12 shows side-by-side comparisons of the proteome reactivities of sulfonates 1, 5, and 9. A Left panel, proteome reactivities of sulfonates 1 and 5. Heat-sensitive protein reactivities selective for 1 and 5 are highlighted (double and single arrowheads, respectively). Right panel, Coomassie blue stained protein gel of samples treated with 1 and 5. Arrowheads highlight abundant proteins correlating in molecular mass with proteins labeled by 5 in the preheated proteome. B, Left panel, proteome reactivities of sulfonates 1 and 9. Heat-sensitive protein reactivities selective for 1 and 9 are highlighted (double and single arrowheads, respectively). Right panel, Coomassie blue stained protein gel of samples treated with 1 and 9. For A and B, different film exposure times are presented for the high (45–100 kDa, 1× time exposure) and low (27–45 kDa, 4× time exposure) molecular mass proteins to permit the signals of labeled proteins to be shown prior to film saturation.

Evaluating the specific proteome reactivity of biotinylated sulfonates To determine whether members of the sulfonate library specifically targeted proteins in the proteome, a method was developed to rapidly distinguish a probe's specific and nonspecific proteome reactivity. Each sulfonate (5 μM) was reacted with two versions of a rat testis proteome: a native proteome and a denatured proteome (generated by preheating the protein sample for 5 min at 80° C.). After 30 minutes at 25° C., the sulfonate-proteome reactions were quenched by adding one reaction volume of standard SDS-PAGE loading buffer and analyzed by SDS-PAGE and avidin blotting. A sulfonate's specific and non-specific proteome reactivity were defined as those protein targets that displayed heat-sensitive and heat-insensitive labeling, respectively. All sulfonates except the octylsulfonate 7 labeled at least one member of the testis proteome in a heat-sensitive manner (FIG. 11A, 11B). Interestingly, four general patterns of specific proteome reactivity were observed among the sulfonates. Thep-toluenesulfonate 3, butylsulfonate 6, and naphthylsulfonate 10 each specifically labeled one 55 kDa protein (FIG. 11A, B; single arrowhead). Thep-methoxybenzenesulfonate 4 and methylsulfonate 5 labeled four members of the proteome in a heat-sensitive manner [FIG. 11A; 55 kDa (single arrowhead), 42 kDa (double arrowhead), 40 kDa (triple arrowhead), and 32 kDa (single dot)], but also showed significant additional reactivity with the preheated proteome. The benzenesulfonate 2 reacted with three of the four proteins labeled by 4 and 5, failing to specifically label only the 40 kDa protein. The p-nitrobenzenesulfonate 8, quinolinesulfonate 9, and thiophenesulfonate 11 each reacted specifically with a 55 kDa protein, as well as two additional proteins poorly labeled by the other reagents [FIG. 11B; 36 kDa (single dot) and 30 kDa (triple dot)]. Finally, the pyridylsulfonate 1 labeled a 55 kDa protein and a 31 kDa protein (FIG. 11A and B, single arrowhead and double dot, respectively), the latter protein appearing uniquely reactive with 1 among the sulfonates that were surveyed. Importantly, most of the sulfonate probes with the exception of 2, 4, and 5 showed low or negligible reactivity with the preheated proteome. Although several sulfonate probes showed overlapping patterns of specific proteome reactivity, their relative reactivities with individual proteins differed considerably. For example, a 36 kDa protein reacted more strongly with quinolinesulfonate 9 than with pyridylsulfonate 1, p-nitrobenzenesulfonate 8 or thiophenesulfonate 11, while a 55 kDa protein displayed the opposite probe selectivity (FIG. 11B). To further examine the different proteome reactivities exhibited by individual sulfonates, the labeling pattern of pyridylsulfonate 1 was compared to that of methylsulfonate 5 and quinolinesulfonate 9 in side-by-side analyses (FIGS. 12A and 3B, respectively). Each sulfonate labeled a unique set of proteins. The patterns of specific reactivity of 1 and 5 appeared nearly orthogonal to one another, with 1 most strongly labeling 55 and 31 kDa proteins (FIG. 12A, left panel, double arrowheads) and 5 most strongly labeling 42 and 32 kDa proteins (FIG. 12A, left panel, single arrowheads). A comparison of the proteome reactivities of 1 and 9 identified two proteins that showed preferred reactivity with 1 (FIG. 12B, left panel, 55 kDa and 31 kDa; double arrowheads) and two proteins that showed enhanced reactivity with 9 (FIG. 12B, left panel, 36 kDa and 30 kDa; single arrowheads). The greater nonspecific reactivity of 5 was also evident in these side-by-side comparisons, as this agent labeled several proteins in a heat-insensitive manner that were unreactive towards 1 and 9. Notably, a Coomassie blue stained protein gel revealed that the proteins labeled by 5 in the preheated proteome represented very abundant proteins (FIG. 12A, right panel, single arrowheads), consistent with the notion that heat-insensitive labeling reflects a nonspecific form of sulfonate reactivity. In contrast, the sulfonate library's heat-sensitive proteome reactivity showed no such bias towards abundant proteins.

Figure 13:
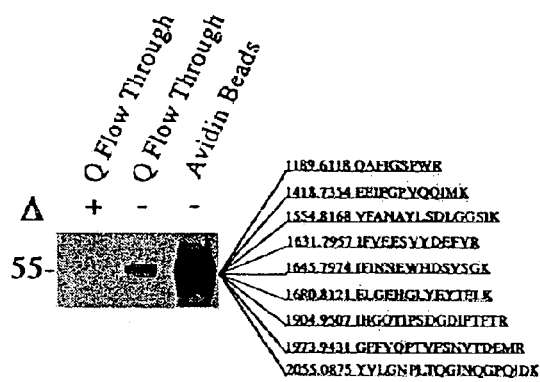
FIG. 13 shows the identification of a 55 kDa specifically-labeled sulfonate target as cytosolic class I aldehyde dehydrogenase (cALDH-I). A, Avidin-based affinity isolation of the 55 kDa 1-labeled protein. Shown is an avidin blot of samples containing the partially purified 55 kDa protein (Q Flow Through) and the affinity-isolated 55 kDa protein (Avidin Beads). Also shown are the tryptic peptides from this protein that identified it as cALDH-I. B, Sulfonate 1 labels recombinant cALDH-I in eukaroytic expression systems. Protein samples from COS-7 (left panel) and MCF-7 (right panel) cells transfected with the cALDH-I cDNA or empty vector (mock) were reacted with 1 and resolved by SDS-PAGE and avidin blotting. A strongly labeled 55 kDa protein was identified only in the cALDH-I-tranfected cells. C, Sulfonate 1 labels recombinant cALDH-I in prokaryotic expression systems. A protein sample of *E. coli* BL-21 cells transformed with a His-tagged version of cALDH-I was reacted with 1 and resolved by SDS-PAGE and avidin blotting. A strongly labeled 60 kDa protein was identified, corresponding to the predicted molecular mass of cALDH-I with an appended N-terminal histidine tag.
Figure 13:
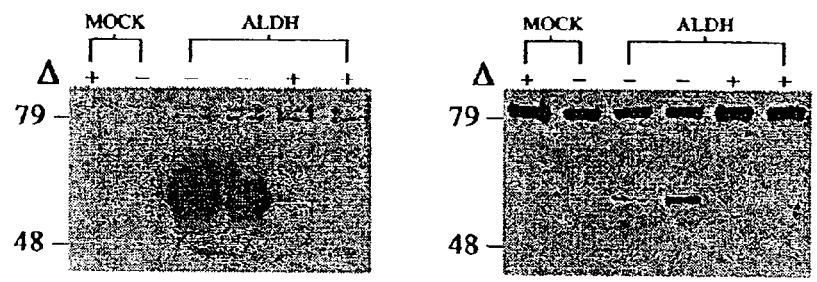
Figure 13:
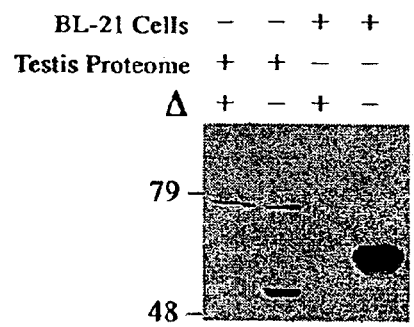
Figure 13:
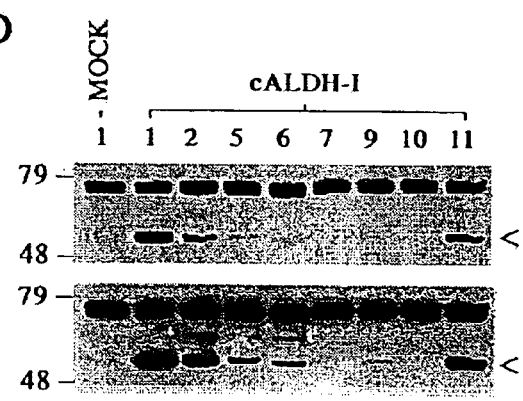

Parameters that influence a sulfonate's specific proteome reactivity The following features of the sulfonate-proteome reaction were varied in order to test their influence on the observed specific and nonspecific protein labeling patterns: time, sulfonate concentration, pH, and the presence/absence of scavenging nucleophiles. For these studies, the reactivity of pyridylsulfonate 1 with the testis proteome was examined. The two testis proteins specifically targeted by 1 were labeled at similar rates, with their signal intensities increasing from 5–40 minutes and then plateauing from 40–120 minutes (FIG. 13A). The absence of additional reactivity from 40–120 minutes could signify that the proteins had labeled to completion by 40 minutes, or less likely, that the concentration of 1 in the reaction was significantly depleted by these later time.

Sulfonate 1's specific and nonspecific proteome reactivities were evaluated over a range of probe concentrations (1–50 $\mu$M). From 1–10 $\mu$M, sulfonate 1 showed specific reactivity with the 31 and 55 kDa proteins that increased in intensity with increasing concentrations of reagent (FIG. 13B). Over this concentration range, sulfonate 1 displayed very low levels of heat-insensitive reactivity with the proteome. From 10 to 50 $\mu$M of 1, the signal intensity of the 31 kDa protein continued to increase, while the intensity of the 55 kDa protein remained relatively constant. Over this concentration range, sulfonate 1's nonspecific labeling increased dramatically, especially in the higher molecular mass range where most of the abundant testis proteins reside. Importantly, however, no new specifically labeled protein targets were identified over this concentration range. Thus, a concentration range of 5–10 $\mu$M appeared optimal for maximizing sulfonate 1's specific versus nonspecific proteome reactivity.

The nonspecific and specific proteome reactivities of sulfonate 1 showed different pH-dependencies, with the former appearing as an inverted bell-shape curve (higher background labeling at pH 6 and 9 than at pH 7 and 8) and the latter increasing in intensity from pH 6 to 8 and plateauing from pH 8 to 10 (FIG. 13C, D). Thus, reactions conducted at pH 7 and 8 produced the highest level of specific reactivity, while at the same time resulting in the lowest degree of nonspecific reactivity.

Sulfonate 1's intrinsic reactivity with nucleophiles was examined by conducting proteome reactions in the presence of millimolar concentrations of free thiols (glutathione, α-mercaptoethanol, or dithiothreitol). If this sulfonate displayed a high reactivity with generic nucleophiles, then the probe's effective concentration in thiol-treated proteome reactions should be greatly reduced, resulting in a significant decrease in the signal intensity of specifically labeled proteins. However, none of the tested thiols affected the labeling intensity of the 55 kDa protein, indicating that sulfonate 1's intrinsic reactivity with nucleophiles is low (FIG. 13D). In contrast, a moderate decrease in the labeling intensity of the 31 kDa protein was detected in the presence of free thiols.

Molecular identification of a protein labeled by biotinylated sulfonates The screening method described above was enacted to rapidly identify protein targets specifically labeled by members of the sulfonate library. By defining these "specific protein targets" as ones that displayed heat-sensitive reactivity with sulfonates the focus was restricted to proteins whose activities would be affected by sulfonate labeling. The assumption inherent to this strategy was that heat-sensitive labeling was reflective of an event taking place within a structured portion of a protein suitable for small-molecule binding. Such structures were anticipated to often represent either ligand binding pockets of receptors or active sites of enzymes. As such, if a sulfonate reacted specifically with one of these sites on a receptor or an enzyme, its reaction would be expected to affect the activity of this protein. Accordingly, the molecular identification of the 55 kDa protein specifically labeled by several members of the sulfonate library was investigated.

Figure 14:
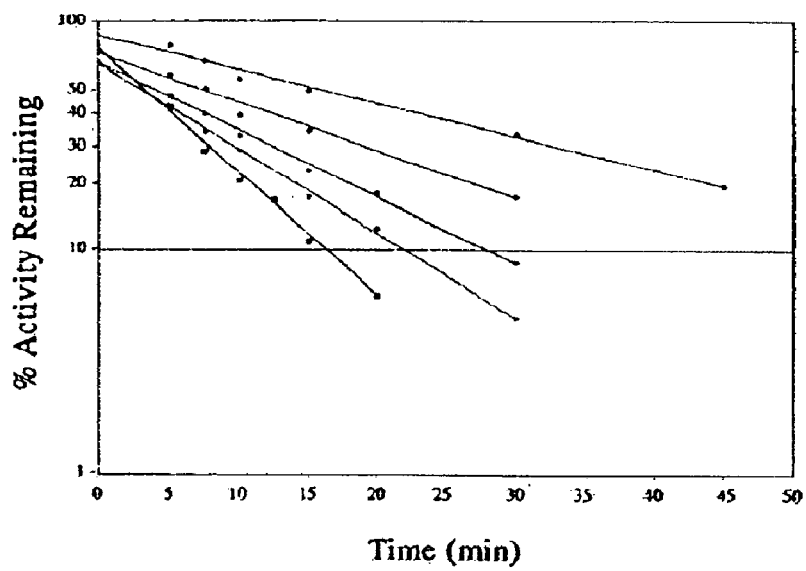
FIG. 14 demonstrates that pyridylsulfonates are time-dependent inhibitors of cALDH-I. A, Time-dependent inactivation of cALDH-I as a function of sulfonate 15 concentration. Recombinant, purified cALDH-I was incubated with different concentrations of 15 and at the time points shown, aliquots of the reaction were removed and assayed for enzyme activity using 1 mM propionaldehyde and 0.5 mM $NAD^+$ as substrate and cofactor, respectively. Concentrations of 15 were: solid diamonds, 2.5 $\mu$M; hollow diamonds, 5 $\mu$M; solid circles, 7.5 $\mu$M; hollow circles, 10 $\mu$M; solid squares, 15 $\mu$M. B, Structure-activity relationship for sulfonate 15-cALDH-I reaction. Sulfonate 15 effectively blocked the labeling of cALDH-I by 1 in the testis proteome. Analogs of 15 in which this sulfonate's pyridyl and octyl groups were replaced with methyl and ethyl groups, respectively (16 and 17, respectively) did not block the labeling of cALDH-I by 1.
Figure 14:
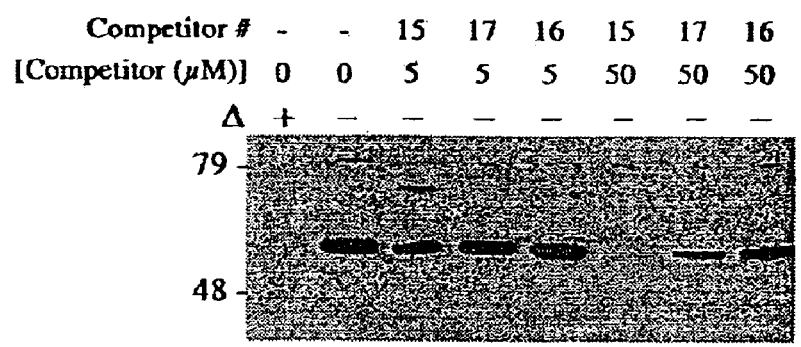

A tissue blot with sulfonate 1 revealed that the labeled 55 kDa protein was most abundant in soluble fractions of rat liver, and therefore the protein was purified from this source. The 55 kDa protein was partially purified by Q-Sepharose anion exchange chromatography. Aliquots of the flow-through and elution fractions of this column were labeled with 1, and the 55 kDa protein was identified in the flow-through fractions. These fractions were combined, labeled with 5 $\mu$M 1 for 30 min, and the protein separated from excess sulfonate by size exclusion chromatography. The protein sample was then treated with avidin agarose beads to isolate the 1-labeled 55 kDa protein. Elution of the avidin-bound proteins was achieved by adding one volume of standard SDS-PAGE loading buffer and heating (90° C., 5 min). This avidin-based affinity purification procedure provided a highly concentrated sample of the 55 kDa protein that was separated by SDS-PAGE and either blotted with avidin (FIG. 14A) or stained with Coomassie blue. The 55 kDa protein was excised from the stained gel, treated with trypsin, and the resulting peptide mixture analyzed by MALDI-TOF mass spectrometry. MS-FIT and Profound searches of protein databases identified the protein as cytosolic 2 class I aldehyde dehydrogenase (cALDH-I; nine tryptic peptides ranging from 1189 to 2055 Da matched this enzyme, 50% total sequence coverage; FIG. 14A), a member of a superfamily of $NAD^+$-dependent enzymes responsible for the oxidation of endogenous and exogenous aldehydes to carboxylic acids [Wang, et al. (1996) J. Biol. Chem. 271, 16288–93; Yoshida, et al. (1998) Eur. J. Biochem. 251, 549–57].

Recombinant Expression of cALDH-I

Figure 15:
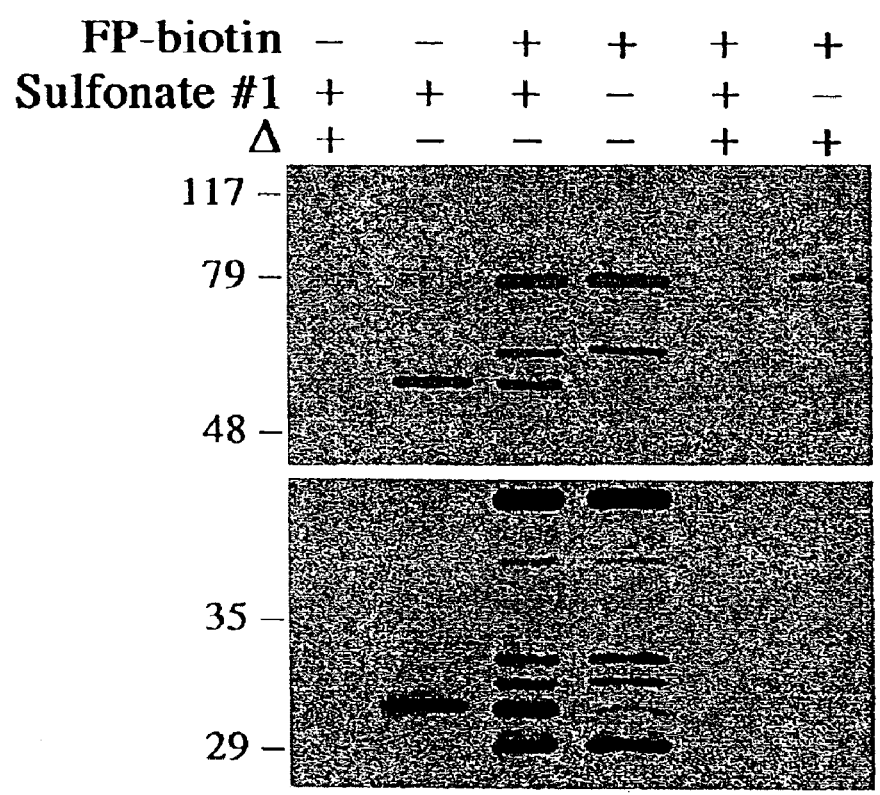
FIG. 15 shows that multiplexing ABPs increases the number of protein activities detected in a single proteome. Shown is a comparison of the heat-sensitive labeling patterns of a testis proteome treated with pyridylsulfonate 1 (2.5 $\mu$M), FP-biotin (4 $\mu$M), or a mixture of pyridylsulfonate 1 (2.5 $\mu$M) and FP-biotin (4 $\mu$M). The mixture-treated proteome exhibited a labeling profile similar to that predicted from merging the profiles of the proteome treated with each ABP alone.

In order to confirm the specific reactivity of cALDH-I with sulfonate 1, this protein was recombinantly expressed in both eukaryotic and prokaryotic systems. The cALDH-I cDNA was subcloned into the pcDNA3 mammalian expression vector and then transfected into COS-7 and MCF-7 cells. cALDH-I-transfected COS-7 and MCF-7 cells both expressed a 55-kDa protein that labeled strongly with sulfonate 1 (FIG. 14B). In contrast, this sulfonate-reactive protein was not detected in mock-transfected versions of each cell type. cALDH-I was also recombinantly expressed in E. coli using the pTrcHis system. Lysates from cALDH-I-transformed E. coli were treated with sulfonate 1 and found to express a single reactive protein of the predicted size for the cALDH-I enzyme bearing an N-terminal histidine tag (60 kDa; FIG. 14C). The His-tagged cALDH-I was purified from E. coli lysates by sequential metal affinity and gel filtration chromatography. This prokaryotic expression system routinely provided 15 mg/L culture volume of purified cALDH-I enzyme. Pyridylsulfonates are time-dependent inhibitors of cALDH-I catalytic activity cALDH-I-catalyzed oxidation of propionaldehyde to propionic acid was measured by observing the reduction of $NAD^+$ to NADH at 340 nm. The observed Michealis constant for propionaldehyde (Km=4.2 μM) displayed by the His-tagged recombinant cALDH-I was comparable to the reported literature value for this enzyme (Km=6.5 μM) [Penzes, et al. (1997) Biochim. Biophys. Acta 1342, 175–81]. To examine the effect of sulfonates on cALDH-I's catalytic activity, the enzyme was treated with varying concentrations of 2-pyridylsulfonyl octanoate (15), a variant of 1 lacking the probe's biotin tag. Sulfonate 15 inhibited cALDH-I's catalytic activity in a time-dependent manner that increased in rate from 2.5 to 15 μM inhibitor (FIG. 15A). Concentrations of 15 greater than 15 μM inactivated cALDH-I at a rate that was too fast to measure under the assay conditions employed. The average $K_{obs}/[I]$ value calculated from reactions conducted at 2.5, 5.0, 7.5, 10, and 15 μM 15 was $(9.7+1.8)\times10^3$ $M^{-1}min^{-1}$. Although the inactivation of cALDH-I at each concentration of 15 could be fit to psuedo-first order kinetics, extrapolation of these reactions back to time zero did not predict 100% enzyme activity. Considering that cALDH-I is a homotetrameric protein, one possible explanation for this data was that individual cALDH-I subunits exhibited different rates of reactivity with 15. In general support of this notion, the kinetics of reactions conducted at lower concentrations of 15 appeared biphasic in nature, with time points preceding 50% enzyme inhibition predicting a slightly faster rate of cALDH-I inactivation than time points at which greater than 50% cALDH-I activity was inhibited. Finally, incubating 15 in the reaction buffer (20 mM Tris.HCl, pH 8.0, 100 mM NaCl, 1 mM DTT) for 60 min prior to the addition of cALDH-I did not affect the inhibitor's potency, indicating that this sulfonate was stable to the assay conditions employed (including the presence of excess freel thiols).

To probe the nature of 15's interaction with cALDH-I, competition studies were performed with both propionaldehyde and $NAD^+$. Recombinant cALDH-I was treated with 10 μM 15 for 10 minutes either in the presence or absence of 25 μM propionaldehyde or 50 mM $NAD^+$ and the percentage of enzyme activity remaining was determined (Table 1). Propionaldehyde had no detectable effect on 15's inactivation kinetics. In contrast, 50 μM $NAD^+$ significantly reduced 15's inhibition of cALDH-I, and higher concentrations of $NAD^+$ completely protected the enzyme from inactivation.

TABLE 1

Competition studies for 15 with propionaldehyde and $NAD^+$ in cALDH

| Substrate | Sulfonate 15 | % Activity Remaining |
|---|---|---|
| — | — | 100 |
| — | 5 μM | 15 |
| 50 μM $NAD^+$ | 5 μM | 61 |
| 25 μM Propionaldehyde | 5 μM | 14 |

Features of 15 Responsible for cALDH-I Inactivation

Analogs of 15 were synthesized in which the agent's octyl and pyridyl substituents were replaced with ethyl (16) and methyl (17) groups, respectively. cALDH-I was incubated for 60 minutes with 50 μM of either 15, 16, or 17, and the percentage of cALDH-I activity remaining was determined (Table 2). While 15 completely inactivated cALDH-I under these conditions, 16 and 17 produced weak and no inhibition, respectively. A $K_{obs}/[I]$ value of 0.25 $M^{-1}min^{-1}$ was calculated for 16, representing a second order inhibition rate constant 40000 times lower than that determined for 15. 15–17 were also tested for their ability to block sulfonate 1's reactivity with cALDH-I in the soluble testis proteome. The testis proteome was preincubated for 30 min with each nonbiotinylated sulfonate at concentrations of 5 or 50 μM. The proteome samples were then treated with 5 μM 1 and the reaction mixtures incubated for 30 minutes prior to analysis by SDS-PAGE and avidin blotting. Consistent with the inhibition kinetics described above, only 15 blocked the labeling of cALDH-I by 1 in the testis proteome (FIG. 15B). Thus, the structure-activity relationship (SAR) determined for sulfonate inactivation of purified cALDH-I correlated well with the SAR observed for sulfonate labeling of this enzyme in complex proteomes. Collectively, these data highlight that the interaction of 15 (and by extrapolation 1) with cALDH-I depends on both the aryl and alkyl chain groups of the inhibitor's structure.

TABLE 2

Structure-activity relationship for sulfonate inactivation of purified cALDH

| Inhibitor | % Activity Remaining |
|---|---|
| None | 100 |
| 15 | 2 |
| 16 | 42 |
| 17 | 100 |

Multiplexing ABPs Increases Proteome Coverage

Figure 17:
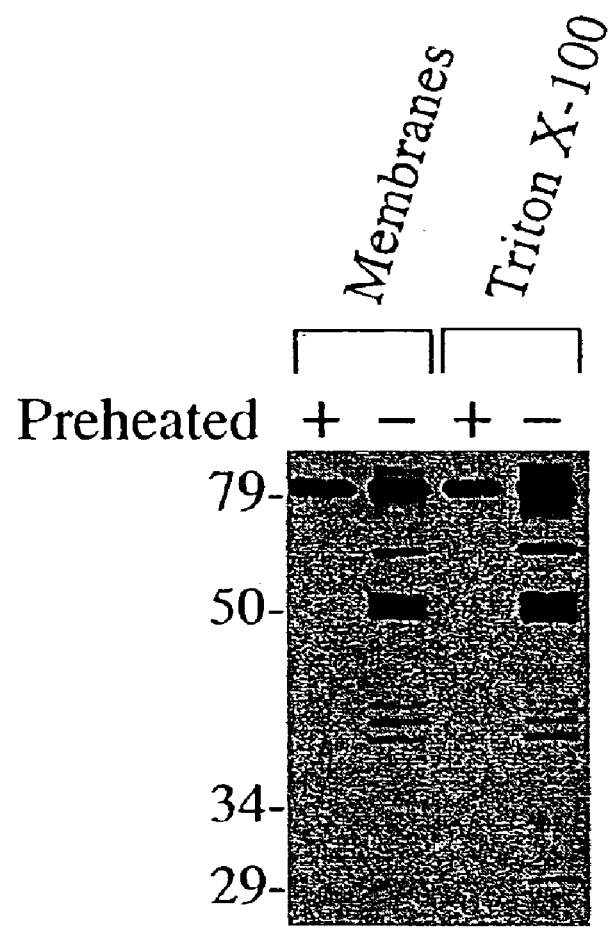
FIG. 17: Comparing the proteome reactivities of FP-biotin and FP-peg-biotin. For all of the experiments depicted in this figure, protein samples represent soluble fractions of rat testis (1 $\mu$g protein/$\mu$L). (A) Protein samples were treated with 4 $\mu$M of either FP-biotin or FP-peg-biotin for 1 hour (50 mM Tris, pH 7.2) and analyzed by SDS-PAGE and blotting with avidin. A pair of 48 kDa serine hydrolases that were robustly labeled by FP-peg-biotin, but not FP-biotin are highlighted (arrowhead). (B–D) Concentration dependence of FP—proteome reactions. Protein samples were treated with 0.5, 1, 2, 4, or 8 $\mu$M of either FP-biotin (B) or FP-peg-biotin (C) for 1 hour (50 mM Tris, pH 7.2) and analyzed by SDS-PAGE and blotting with avidin. The upper and lower panels represent 1 and 10 minute film exposures respectively. Several serine hydrolases appearing to show no FP-peg-biotin concentration dependence in a one hour reaction (C, arrowheads), exhibited strong probe concentration dependence in a one minute reaction (D, arrowheads).

The rat testis proteome was treated with either 2.5 μM sulfonate 1, 5 μM FP-biotin, or a mixture of 2.5 μM 1 and 5 μM FP-biotin [Liu, et al. Proc. Natl. Acad. Sci USA 96, 14694–99], and the resulting heat-sensitive labeling profiles were visualized by SDS-PAGE and avidin blotting. As can be seen in FIG. 17, applying a mixture of sulfonate 1 and FP-biotin to the testis proteome effectively detected in a single sample the proteins labeled by both probes individually. Notably, a preheated sample treated with the same probe mixture displayed a very low level of labeling that was comparable to the nonspecific reactivity observed when each probe was tested alone. These data support that by multiplexing ABPs, one can significantly increase the coverage of specific protein reactivities detectable in a single proteome assay.

Example 8

To generate chemical probes for the active sites of other enzymes like metallo-hydrolases and NT-dependent enzymes, we will develop chemical probes are developed that can profile metallo-hydrolases and NT-dependent enzymes in an activity-dependent manner. Experiments for this Specific Aim will include: i) the design and synthesis of tagged active site-directed inhibitors of metallo-hydrolases and NT-dependent enzymes, and ii) the testing of candidate inhibitors for selective and activity-based reactivity with metallo-hydrolases and NT-dependent enzymes in whole cell and tissue samples.

As with serine hydrolases, metallo-hydrolases and NT-dependent enzymes are often regulated posttranslationally by either endogenous inhibitory proteins or cis-acting autoinhibitory sequences. Collectively, these posttranslational regultory mechanisms make traditional genomics/proteomics approaches inappropriate for recording dynamics in metallohydrolase and/or kinase function. The goals of this specific aim are to design, synthesize, and test candidate activity-based chemical probes that target metallohydrolases and NT-dependent enzymes.

The design and synthesis of active site-directed chemical probes that target metallo-hydrolases and NT-dependent enzymes. For metallo-hydrolase-directed agents, we will create hydroxamic acid inhibitors coupled to biotin, with the hope that these agents will bind tightly [either reversibly or irreversibly] to metallo-hydrolase active sites. The attached biotintag will allow for the rapid detection and isolation of reactive proteins. We will synthesize modest-sized combinatorial libraries of tagged hydroxamates diversified at the R1 and R2 positions and select those inhibitors that exhibit both 1) broad spectrum reactivity with defined classes of metallo-hydrolases, and 2) low crossreactivity with unrelated proteins. Several additional candidate activity-based probes of metallo-hydrolases will also be synthesized, founded on the principle that these molecules should possess a group whose latent reactivity is unveiled on coordination to a Lewis acidic, active site-bound metal ion. These reagents include: pyridyl sulfonates and metal-induced vinylnitrosonium and aziridinium ions. Activity-based probes that are target NT-dependent enzymes will consist of biotin-tagged, reactive or non-hydrolyzable chemical analogs of the appropriate NT. These molecules should take advantage of the fact that many NT-dependent enzymes do not bind NTs in their autoinhibited states.

Once each candidate probe is generated, it will be screened against both commerically available enzymes and whole cell/tissue samples. An initial assessment of the activity-based nature of the observed interactions will be determined by comparing the reactivity of heated versus unheated protein samples. Those metallo-hydrolase-directed reagents that show selective and heat-sensitive reactivity with MMPs will be further studied for their ability to distinguish free MMPs (active) from those bound by TIMPs (inactive). Those reagents directed against NT-dependent enzymes that show selective and heat-sensitive reactivity will be further studied for their ability to distinguish active versus inactive (e.g., autoinhibited) enzymes. Finally, it is important to stress a major advantage of our experimental strategy: because each chemical reagent that we synthesize will be coupled to biotin, we have an opportunity to rapidly define its specific sites of action in a complex proteome. Thus, even if a reagent fails to react with the proposed target (e.g., metallo-hydrolases),we will still be able to assess whether it shows specific reactivity with other enzyme families. In this manner, the work proposed may not only identify class-selective reagents for metallo-hydrolases and NT-dependent enzymes, but simultaneously reactive chemical groups that target other enzyme families as well. This form of reverse drug discovery, in which a postulated chemical inhibitor is mixed with whole cell/tissue extracts and its target selectivity revealed by tag recognition should prove quite powerful for the identification of novel small molecule-enzyme interactions that can in turn be exploited for activity-based proteomics investigations.

The subject inhibitors may be used in a variety of ways. One application is to determine the serine hydrolase activity of a physiological sample. The sample may be blood, cells, tissue, or other physiological sample of interest. In some situations, samples that are suspected of having one or have serine hydrolases may be monitored, as in the genetic engineering of serine hydrolase proteins, where the efficiency of synthesis would be of interest. In the case of tissue or cells, the cells may be lysed in accordance with conventional conditions, using a homogenizer, blender, pellets, centrifuge or other convenient device. The resulting lysed cellular composition may be centrifuged and the supernatant adjusted for protein content. Depending on the nature of the ligand, the supernatant fraction may be freed of naturally occurring ligand and/or receptor. The supernatant may be further treated, as appropriate, adding buffer, further dilution, fractionation by chromatography, etc. Where fractionated, individual fractions will be used in the assay.

Candidate compounds to be used as therapeutics associated with indications involving serine hydrolase dysfunction, particularly for inhibiting specific or groups of serine hydrolases, may be monitored by preparing a reaction mixture with one or more hydrolases and monitoring the effect on the rate of inhibition. One would add one or more subject compounds and a candidate compound and then monitor the rate of inhibition, by isolating aliquots and analyzing the aliquot for serine hydrolase activity or isolating bound serine hydrolases and analyzing the bound serine hydrolases.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

While the invention has been described in detail with reference to certain preferred embodiments thereof, it will be understood that modifications and variations are within the spirit and scope of that which is described and claimed.

What is claimed is:

1. A method for screening for the bioactivity of a candidate compound toward a group of related target proteins in a proteomic mixture of proteins from a cell, employing at least one probe, each probe comprising a reactive functionality group specific for said group of target proteins and a ligand, each probe of the formula:

R(F-L)—X wherein:
X is a ligand for binding to a reciprocal receptor and/or providing a detectable signal;
L is an alkylene, oxyalkylene or polyoxyalkylene linking group, wherein said oxyalkylenes are of from 2 to 3 carbon atoms;
F is a phosphonate or sulfonyl functional group reactive at an active site of a target enzyme; and
R is bonded to F and a moiety of less than 1 kDal providing specific affinity for said enzymes, and when F is phosponate, R is fluorine and when F is sulfonyl, R is an aryl or heteroaryl group; said method comprising:

separating the proteomic mixture into two portions,
treating one of the two portions with the candidate compound to obtain an inactivated portion, wherein the candidate compound is a non-covalent agent,
combining at least one probe with the untreated portion of said mixture under conditions for reaction with said target proteins to obtain a first specimen,
combining at least one probe with the inactivated portion under conditions for reaction with said target proteins to obtain a second specimen;
sequestering proteins conjugated with said at least one probe from each of said specimens;
determining the proteins that are sequestered; and
comparing the amount of each of the proteins sequestered from the first specimen and the second specimen as indicative of the bioactivity of said candidate compound with said target proteins.

2. A method according to claim 1, wherein said probe is a fluorophosphonyl and said enzymes are serine hydrolases.

3. A method according to claim 1, wherein said probe is a sulfonate, R is a heteroaryl and said enzymes are aldehyde dehydrogenases.

4. A method according to claim 3, wherein said heteroaryl is pyridyl.

5. A method according to claim 1, wherein X is biotin.

* * * * *